(12) United States Patent
Remiszewski et al.

(10) Patent No.: US 10,723,708 B2
(45) Date of Patent: Jul. 28, 2020

(54) ANTI-HCMV COMPOSITIONS AND METHODS

(71) Applicant: FORGE Life Science, LLC, Doylestown, PA (US)

(72) Inventors: Stacy Remiszewski, Doylestown, PA (US); Emre Koyuncu, Doylestown, PA (US); Qun Sun, Princeton, PA (US); Lillian Chiang, Princeton, PA (US)

(73) Assignee: Evrys Bio, LLC, Doylestown, PA (US)

( * ) Notice: Subject to any disclaimer, the term of this patent is extended or adjusted under 35 U.S.C. 154(b) by 0 days.

(21) Appl. No.: 15/525,401

(22) PCT Filed: Nov. 9, 2015

(86) PCT No.: PCT/US2015/059763
§ 371 (c)(1),
(2) Date: May 9, 2017

(87) PCT Pub. No.: WO2016/077240
PCT Pub. Date: May 19, 2016

(65) Prior Publication Data
US 2018/0170884 A1   Jun. 21, 2018

Related U.S. Application Data

(60) Provisional application No. 62/077,787, filed on Nov. 10, 2014.

(51) Int. Cl.
| | | |
|---|---|---|
| C07D 215/40 | (2006.01) |
| C07C 217/62 | (2006.01) |
| A61K 31/47 | (2006.01) |
| A61P 31/12 | (2006.01) |
| A61P 31/20 | (2006.01) |
| C07D 241/44 | (2006.01) |
| C07C 235/38 | (2006.01) |
| C07D 209/04 | (2006.01) |
| A61K 31/522 | (2006.01) |
| A61K 31/4035 | (2006.01) |
| C07D 209/08 | (2006.01) |

(52) U.S. Cl.
CPC ........ *C07D 241/44* (2013.01); *A61K 31/4035* (2013.01); *A61K 31/47* (2013.01); *A61K 31/522* (2013.01); *A61P 31/12* (2018.01); *A61P 31/20* (2018.01); *C07C 217/62* (2013.01); *C07C 235/38* (2013.01); *C07D 209/04* (2013.01); *C07D 209/08* (2013.01); *C07D 215/40* (2013.01)

(58) Field of Classification Search
None
See application file for complete search history.

(56) References Cited

U.S. PATENT DOCUMENTS

| | | |
|---|---|---|
| 5,135,947 A | 8/1992 | Robertson |
| 5,292,962 A | 3/1994 | Alt |
| 2008/0300236 A1* | 12/2008 | Codd ................... C07D 215/38 514/217.07 |

OTHER PUBLICATIONS

PubChem SID 123649111 (available date Jun. 21, 2011).*
Pan et al. (Organic Letters, 15(18): 4758-4761, 2013).*
STN Registry Record (RN# 1405145-36-9, Entry date: Nov. 23, 2012).*
PubChem SID 145363134 (available date: Oct. 18, 2012).*
Yu Wei et al: "Pd(II)-Catalyzed Intermolecular Arylation of Unactivated C(sp 3 )-H Bonds with Aryl Bromides Enabled by 8-Aminoquinoline Auxiliary" Organic Letters, Mar. 2014, 16(8): 2248-2251.

* cited by examiner

*Primary Examiner* — Bong-Sook Baek
(74) *Attorney, Agent, or Firm* — F. Aaron Dubberley

(57) ABSTRACT

This document relates to compounds useful as agents for preventing or treating human cytomegalovirus (HCMV) infections.

14 Claims, No Drawings

ANTI-HCMV COMPOSITIONS AND METHODS

STATEMENT OF FEDERALLY FUNDED RESEARCH

This invention was made with government support under grant number R43 AI114079 awarded by the National Institutes of Health. The government has certain rights to the invention.

TECHNICAL FIELD

This document relates to compounds useful for preventing, treating or ameliorating human cytomegalovirus infection.

BACKGROUND

Human cytomegalovirus (HCMV) is a major cause of birth defects and opportunistic infections in immunosuppressed individuals, and a possible cofactor in certain cancers. Organ transplant patients under immunosuppressive therapy are at high risk for viral infections; activation of a latent virus as well as donor or community acquired primary infections can cause significant complications including graft rejection, morbidity, and mortality. Herpesviruses (e.g. HCMV, HSV-1), polyomaviruses (e.g. BKV and JCV), hepatitis viruses (HBV and HCV) and respiratory viruses (e.g. influenza A, adenovirus) are the 4 major viral classes infecting these patients. Cytomegalovirus (HCMV) is the most prevalent post-transplant pathogen; HCMV can infect most organs, and despite the availability of HCMV antivirals such as ganciclovir, nephrotoxic side effects and increasing rates of drug-resistance significantly reduce graft and patient survival. In addition, HCMV-mediated immune modulation can reactivate distinct latent viruses carried by most adults.

SUMMARY

The instant invention provides a method for treating or preventing an HCMV infection in a subject by administering a therapeutically effective amount of a compound having the structure of Formula I:

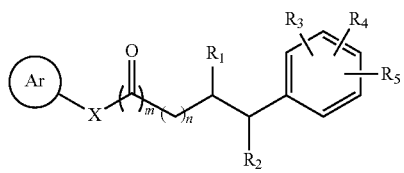

Formula I wherein:
  X is NH or O, provided that when m is 1, X is NH;
  $R_1$ and $R_2$ are independently selected from H, halo, lower straight chain alkyl, lower branched alkyl, and $OR_6$;
  $R_3$, $R_4$, and $R_5$ are independently selected from H, halo, —CN, lower straight chain alkyl, lower branched alkyl, and $OR_6$;
  each $R_6$ is independently selected from H, lower straight chain alkyl, and lower branched alkyl;
  m is 0 or 1;
  n is 0, 1, 2 or 3, provided that when m is 1, n is not 3; and
  Ar is a bicyclic aryl group having between 8 and 12 ring atoms, wherein 0, 1 or 2 ring atoms are heteroatoms independently selected from N, O, S and the bicyclic aryl group is substituted with 0, 1 or 2 groups independently selected from halo, —CN, lower straight chain alkyl and lower branched alkyl;
  or a pharmaceutically acceptable salt thereof.

The invention also provides compounds having, and pharmaceutically acceptable salts of compounds having, the structure of Formula I:

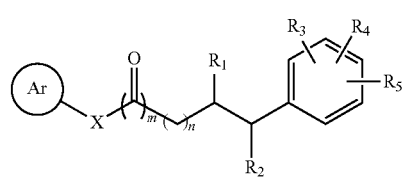

Formula I wherein:
  X is NH or O, provided that when m is 1, X is NH;
  $R_1$ and $R_2$ are independently selected from H, halo, lower straight chain alkyl, lower branched alkyl, and $OR_6$;
  $R_3$, $R_4$, and $R_5$ are independently selected from H, halo, —CN, lower straight chain alkyl, lower branched alkyl, and $OR_6$;
  each $R_6$ is independently selected from H, lower straight chain alkyl, and lower branched alkyl;
  m is 0 or 1;
  n is 0, 1, 2 or 3, provided that when m is 1, n is not 3; and
  Ar is selected from the group consisting of:

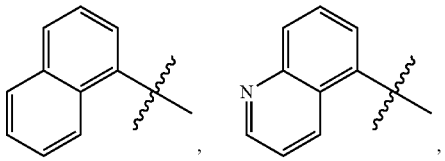

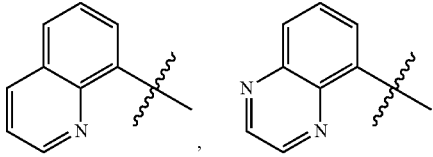

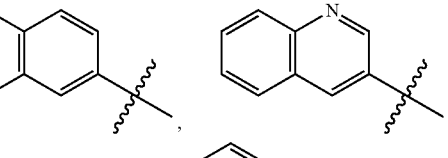

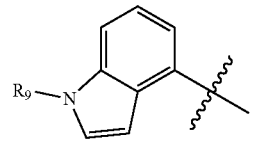

or substituted with 0, 1 or 2 groups independently selected from halo, —CN, lower straight chain or branched alkyl and wherein:
  $R_9$ is selected from H, lower straight chain or branched alkyl, —C(O)$R_{10}$ or —SO—$_2R_{10}$ and $R_{10}$ is selected from, lower straight chain or branched alkyl.

The compounds of the invention are useful for treating and/or preventing HCMV infections.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Provided herein are compounds useful in the treatment and/or prevention of HCMV infections.

Provided herein are methods for treating or preventing an HCMV infection in a subject. In some embodiments, the methods include administering a therapeutically effective amount of one or more of the compounds provided herein. In some embodiments, the compounds provided herein can inhibit HCMV production in a cell infected with the virus. In such embodiments, the cell is contacted with a virus production inhibiting amount of one or more compounds provided herein.

Provided herein is a method for treating or preventing an HCMV infection in a subject by administering a therapeutically effective amount of a compound having the structure of Formula I:

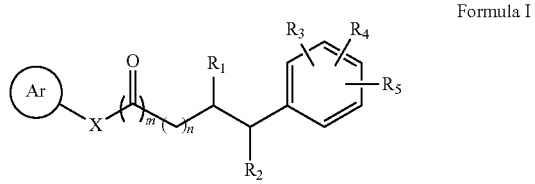

Formula I wherein:

X is NH or O, provided that when m is 1, X is NH;

$R_1$ and $R_2$ are independently selected from H, halo, lower straight chain alkyl, lower branched alkyl, and $OR_6$;

$R_3$, $R_4$, and $R_5$ are independently selected from H, halo, —CN, lower straight chain alkyl, lower branched alkyl, and $OR_6$;

each $R_6$ is independently selected from H, lower straight chain alkyl, and lower branched alkyl;

m is 0 or 1;

n is 0, 1, 2 or 3, provided that when m is 1, n is not 3; and

Ar is a bicyclic aryl group having between 8 and 12 ring atoms, wherein 0, 1 or 2 ring atoms are heteroatoms independently selected from N, O, S and the bicyclic aryl group is substituted with 0, 1 or 2 groups independently selected from halo, —CN, lower straight chain alkyl and lower branched alkyl;

or a pharmaceutically acceptable salt thereof, with the proviso that the compound is not

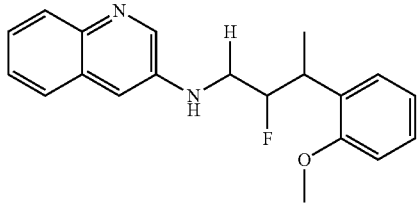 [SMILES: COc1ccccc1C(C)C(F)CNc1cnc2ccccc2c1]

or a pharmaceutically acceptable salt thereof.

Some embodiments of the method for treating or preventing an HCMV infection in a subject provided herein can include administering a therapeutically effective amount of a compound having the structure of Formula I, wherein Ar is selected from the group consisting of:

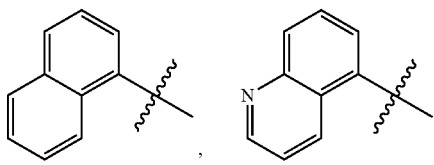

,

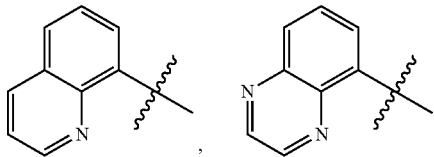

,

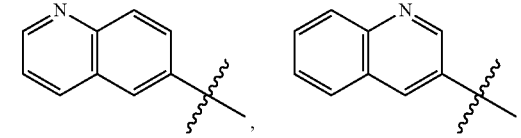

, or

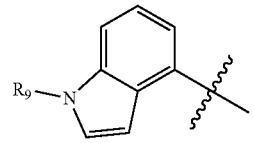

substituted with 0, 1 or 2 groups independently selected from halo, —CN, lower straight chain or branched alkyl and wherein:

$R_9$ is selected from H, lower straight chain or branched alkyl, —C(O)$R_{10}$ or —SO—$_2R_{10}$ and $R_{10}$ is selected from lower straight chain or branched alkyl.

Some embodiments of the method for treating or preventing an HCMV infection in a subject provided herein can include administering a therapeutically effective amount of a compound having the structure of Formula I, wherein Ar is selected from the group consisting of:

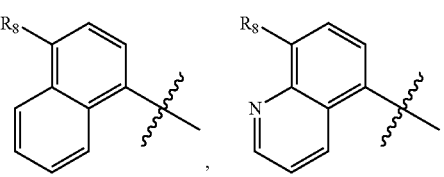

,

-continued

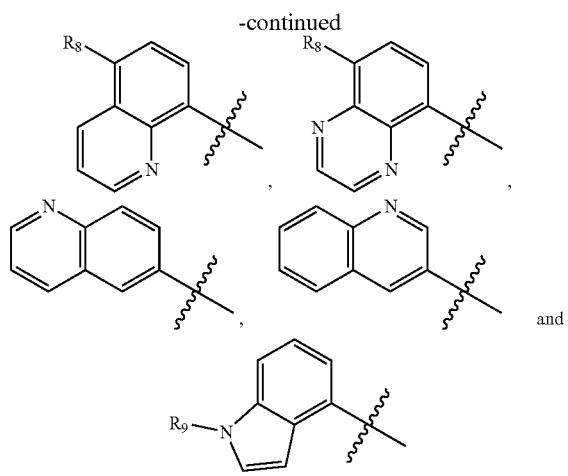

wherein:

$R_8$ is selected from H, halo and —CN;

$R_9$ is selected from H, lower straight chain or branched alkyl, —C(O)$R_{10}$ or —SO$_2R_{10}$ and $R_{10}$ is selected from H, lower straight chain or branched alkyl.

Some embodiments of the method for treating or preventing an HCMV infection in a subject provided herein can include administering a therapeutically effective amount of a compound having the structure of Formula I, wherein at least one of $R_3$, $R_4$, or $R_5$ is in the ortho position and selected from the group consisting of halo, —CN, a straight chain or branched alkyl of 1 to 4 carbon atoms, and a straight or branched alkoxy of 1 to 4 carbon atoms.

Some embodiments of the method for treating or preventing an HCMV infection in a subject provided herein can include administering a therapeutically effective amount of a compound having the structure of Formula I, wherein at least one of $R_3$, $R_4$, or $R_5$ is in the ortho position and selected from the group consisting of halo, —CN, and a straight or branched alkoxy of 1 to 4 carbon atoms.

Some embodiments of the method for treating or preventing an HCMV infection in a subject provided herein can include administering a therapeutically effective amount of a compound having the structure of Formula I, wherein at least one of $R_3$, $R_4$, or $R_5$ is in the ortho position and selected from the group consisting of halo, —CN, a straight chain or branched alkyl of 1 to 4 carbon atoms, and a straight or branched alkoxy of 1 to 4 carbon atoms, and $R_2$ is selected from halo, lower straight chain or branched alkyl, and OR$_6$.

Some embodiments of the method for treating or preventing an HCMV infection in a subject provided herein can include administering a therapeutically effective amount of a compound having the structure of Formula I, wherein at least one of $R_3$, $R_4$, or $R_5$ is in the ortho position and selected from the group consisting of chloro, methyl and methoxy.

Some embodiments of the method for treating or preventing an HCMV infection in a subject provided herein can include administering a therapeutically effective amount of a compound having the structure of Formula I, wherein at least one of $R_3$, $R_4$, or $R_5$ is in the ortho position and selected from the group consisting of chloro, bromo and methoxy.

Some embodiments of the method for treating or preventing an HCMV infection in a subject provided herein can include administering a therapeutically effective amount of a compound having the structure of Formula I, wherein at least one of $R_3$, $R_4$, or $R_5$ is in the ortho position and selected from the group consisting of chloro, methyl and methoxy, and $R_2$ is selected from halo, lower straight chain or branched alkyl, and OR$_6$.

Some embodiments of the method for treating or preventing an HCMV infection in a subject provided herein can include administering a therapeutically effective amount of a compound having the structure of Formula I, wherein at least two of $R_3$, $R_4$, or $R_5$ are in the ortho position and selected from the group consisting of halo, —CN, a straight chain or branched alkyl of 1 to 4 carbon atoms, and a straight or branched alkoxy of 1 to 4 carbon atoms.

Some embodiments of the method for treating or preventing an HCMV infection in a subject provided herein can include administering a therapeutically effective amount of a compound having the structure of Formula I, wherein at least two of $R_3$, $R_4$, or $R_5$ are in the ortho position and selected from the group consisting of halo, —CN, a straight chain or branched alkyl of 1 to 4 carbon atoms, and a straight or branched alkoxy of 1 to 4 carbon atoms, and $R_2$ is selected from halo, lower straight chain or branched alkyl, and OR$_6$.

Some embodiments of the method for treating or preventing an HCMV infection in a subject provided herein can include administering a therapeutically effective amount of a compound having the structure of Formula I, wherein two of $R_3$, $R_4$, or $R_5$ are chloro in the ortho position.

Some embodiments of the method for treating or preventing an HCMV infection in a subject provided herein can include administering a therapeutically effective amount of a compound having the structure of Formula I, wherein two of $R_3$, $R_4$, or $R_5$ are chloro in the ortho position and $R_2$ is selected from halo, lower straight chain or branched alkyl, and OR$_6$.

Some embodiments of the method for treating or preventing an HCMV infection in a subject provided herein can include administering a therapeutically effective amount of a compound having the structure of Formula I, wherein $R_2$ is selected from halo, lower straight chain or branched alkyl, and OR$_6$.

Some embodiments of the method for treating or preventing an HCMV infection in a subject provided herein can include administering a therapeutically effective amount of a compound having the structure of Formula I, wherein when m is 0, n is not 0.

Some embodiments of the method for treating or preventing an HCMV infection in a subject provided herein can include administering a therapeutically effective amount of a compound selected from the group consisting of:

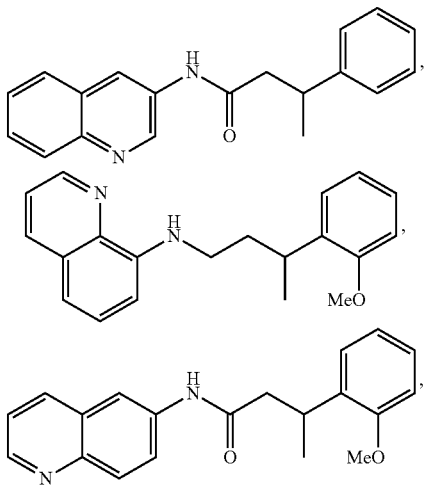

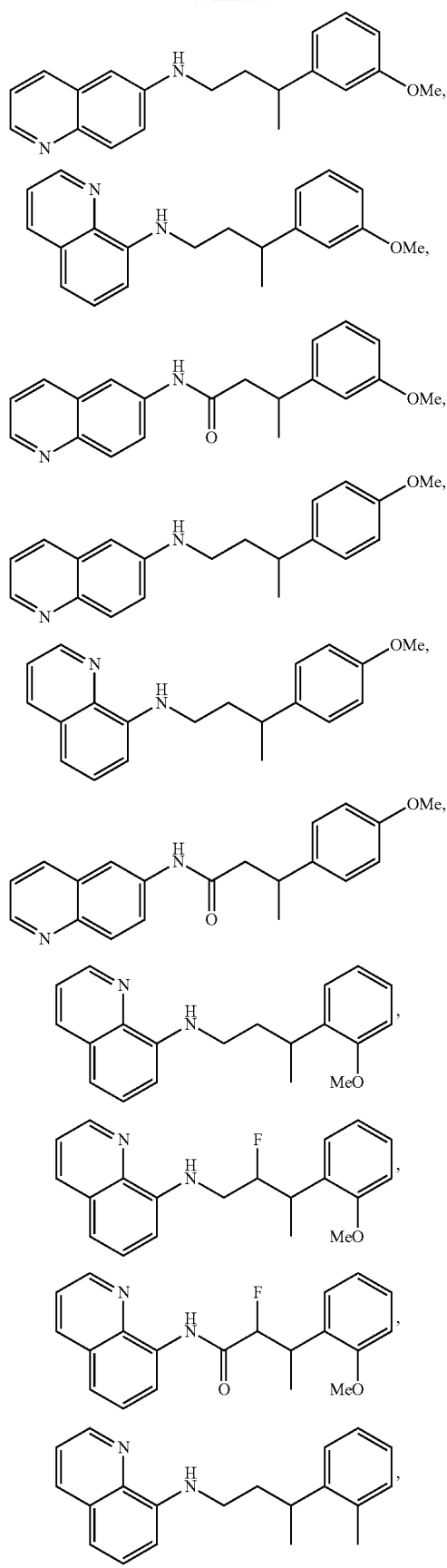
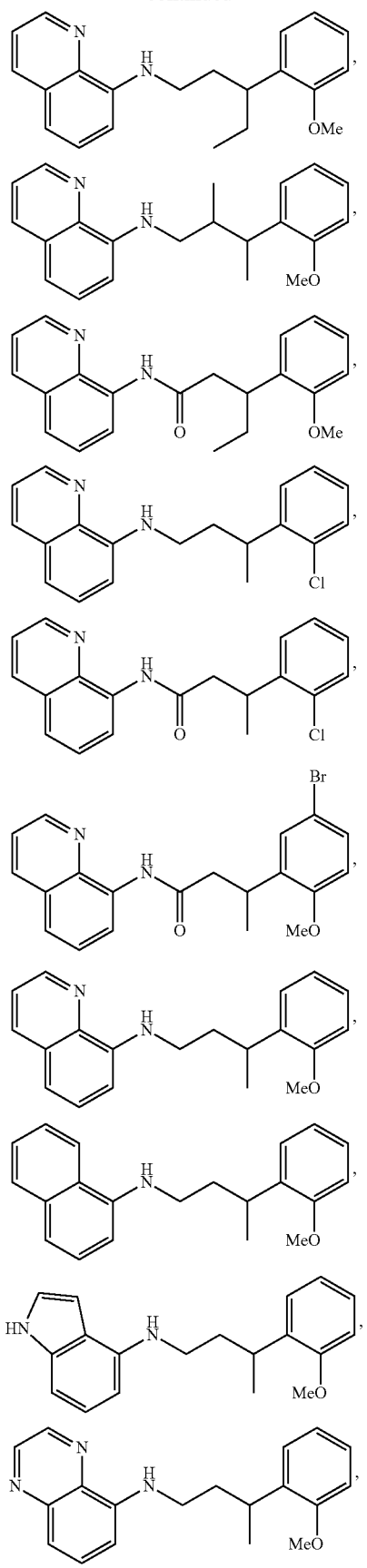

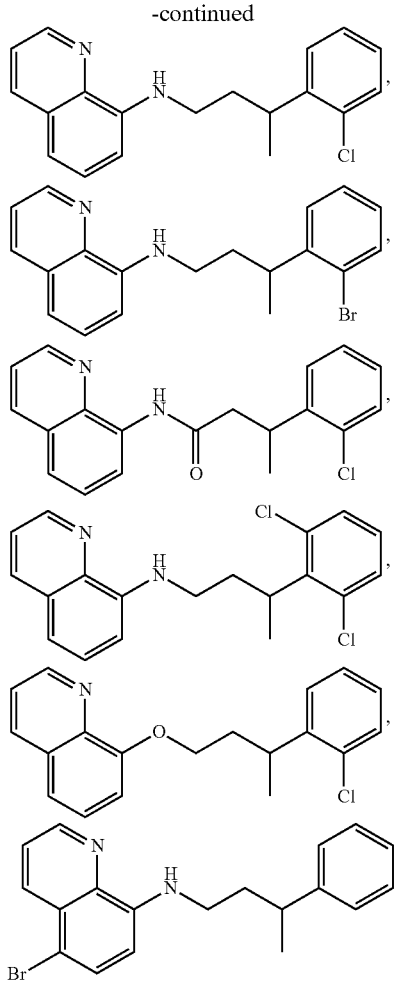

and pharmaceutically acceptable salts thereof.

Also provided herein is a method of inhibiting HCMV production comprising contacting an HCMV-infected cell with a virus production inhibiting amount of any of the compounds of Formula I.

An antiviral agent can also be administered in conjunction with the compounds and the methods described herein. The agent can be any therapeutic agent useful in the treatment of an HCMV infection. For example, an antiviral agent can include acyclovir, docosanol, ribarivin, interferons, and the like; cellulose acetate, carbopol and carrageenan, pleconaril, amantidine, rimantidine, fomivirsen, zidovudine, lamivudine, zanamivir, oseltamivir, brivudine, abacavir, adefovir, amprenavir, arbidol, atazanavir, atripla, cidofovir, combivir, edoxudine, efavirenz, emtricitabine, enfuvirtide, entecavir, famciclovir, fosamprenavir, foscarnet, fosfonet, ganciclovir, gardasil, ibacitabine, imunovir, idoxuridine, imiquimod, indinavir, inosine, integrase inhibitor, lamivudine, lopinavir, loviride, mk-0518, maraviroc, moroxydine, nelfinavir, nevirapine, nexavir, nucleotide and/or nucleoside analogues, oseltamivir, penciclovir, peramivir, podophyllotoxin, rimantadine, ritonavir, saquinavir, stavudine, tenofovir, tenofovir disoproxil, tipranavir, trifluridine, trizivir, tromantadine, truvada, valaciclovir, valganciclovir, vicriviroc, vidarabine, viramidine, zalcitabine, morpholino oligonucleotides, ribozyme, protease inhibitors, an assembly inhibitor (e.g., rifampicin), zidovudine, brincidofovir, favipiravir, nitoxanide, letermovir, maribavir, CMX157 or a combination or two or more antiviral agents.

In some embodiments, a compound provided herein can be administered before, after, or simultaneously with the administration or one or more antiviral agents.

Compounds and Compositions

Provided herein are compounds useful for preventing and/or treating HCMV infections. Such compounds include compounds having the structure of Formula I:

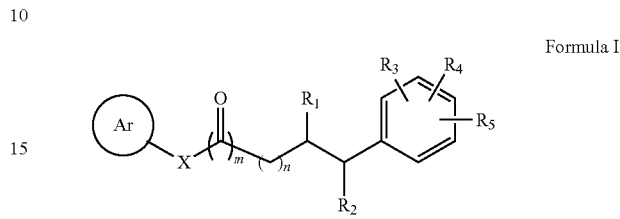

Formula I wherein:

X is NH or O, provided that when m is 1, X is NH;

$R_1$ and $R_2$ are independently selected from H, halo, lower straight chain or branched alkyl, and $OR_6$;

$R_3$, $R_4$, and $R_5$ are independently selected from H, halo, —CN, lower straight chain or branched alkyl, and $OR_6$;

each $R_6$ is independently selected from H, lower straight chain or branched alkyl;

m is 0 or 1;

n is 0, 1, 2 or 3, provided that when m is 1, n is not 3; and

Ar is selected from the group consisting of:

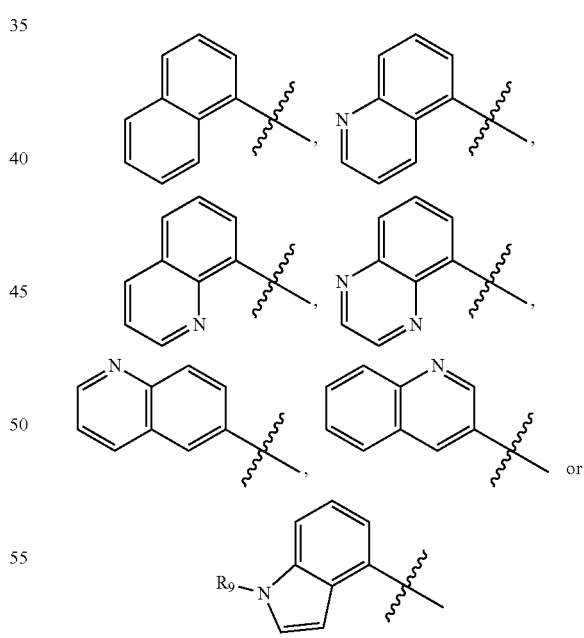

substituted with 0, 1 or 2 groups independently selected from halo, —CN, lower straight chain or branched alkyl and wherein:

$R_9$ is selected from H, lower straight chain or branched alkyl, —C(O)$R_{10}$ or —SO$_2$$R_{10}$ and $R_{10}$ is selected from lower straight chain or branched alkyl, with the proviso that the compound is not

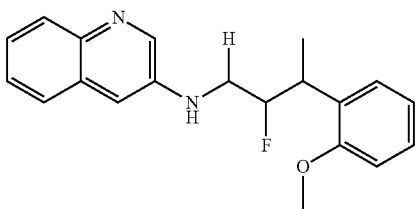 [SMILES: COc1ccccc1C(C)C(F)CNc1cnc2ccccc2c1]

or a pharmaceutically acceptable salt thereof.

In some embodiments of the compounds of Formula I, Ar is selected from the group consisting of:

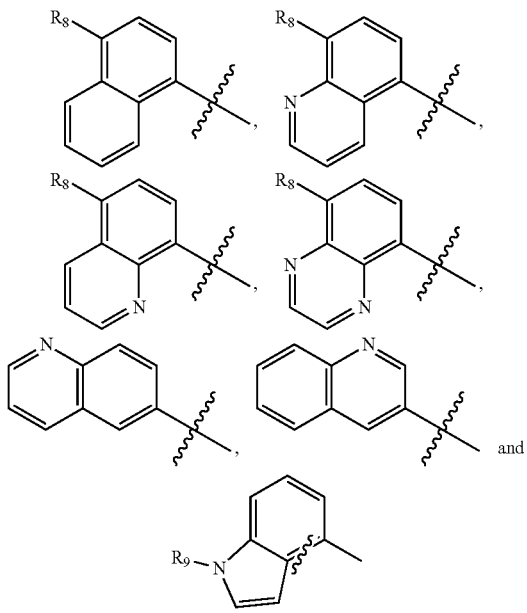

wherein:

$R_8$ is selected from H, halo and —CN;

$R_9$ is selected from H, lower straight chain or branched alkyl, —C(O)$R_{10}$ or —SO$_2R_0$ and $R_{10}$ is selected from lower straight chain or branched alkyl.

In some embodiments of the compounds of Formula I, at least one of $R_3$, $R_4$, or $R_5$ is in the ortho position and selected from the group consisting of halo, —CN, a straight chain or branched alkyl of 1 to 4 carbon atoms, and a straight or branched alkoxy of 1 to 4 carbon atoms.

In some embodiments of the compounds of Formula I, at least one of $R_3$, $R_4$ or $R_5$ is in the ortho position and selected from the group consisting of halo, —CN, and a straight or branched alkoxy of 1 to 4 carbon atoms.

In some embodiments of the compounds of Formula I, at least one of $R_3$, $R_4$, or $R_5$ is in the ortho position and selected from the group consisting of halo, —CN, a straight chain or branched alkyl of 1 to 4 carbon atoms, and a straight or branched alkoxy of 1 to 4 carbon atoms, and $R_2$ is selected from halo, lower straight chain or branched alkyl, and OR$_6$.

In some embodiments of the compounds of Formula I, at least one of $R_3$, $R_4$, or $R_5$ is in the ortho position and selected from the group consisting of chloro, methyl and methoxy.

In some embodiments of the compounds of Formula I, at least one of $R_3$, $R_4$ or $R_5$ is in the ortho position and selected from the group consisting of chloro, bromo and methoxy.

In some embodiments of the compounds of Formula I, at least one of $R_3$, $R_4$, or $R_5$ is in the ortho position and selected from the group consisting of chloro, methyl and methoxy, and $R_2$ is selected from halo, lower straight chain or branched alkyl, and OR$_6$.

In some embodiments of the compounds of Formula I, at least two of $R_3$, $R_4$, or $R_5$ are in the ortho position and selected from the group consisting of halo, —CN, a straight chain or branched alkyl of 1 to 4 carbon atoms, and a straight or branched alkoxy of 1 to 4 carbon atoms.

In some embodiments of the compounds of Formula I, at least two of $R_3$, $R_4$, or $R_5$ are in the ortho position and selected from the group consisting of halo, —CN, a straight chain or branched alkyl of 1 to 4 carbon atoms, and a straight or branched alkoxy of 1 to 4 carbon atoms, and $R_2$ is selected from halo, lower straight chain or branched alkyl, and OR$_6$.

In some embodiments of the compounds of Formula I, two of $R_3$, $R_4$, or $R_5$ are chloro in the ortho position.

In some embodiments of the compounds of Formula I, two of $R_3$, $R_4$, or $R_5$ are chloro in the ortho position and $R_2$ is selected from halo, lower straight chain or branched alkyl, and OR$_6$.

In some embodiments of the compounds of Formula I, $R_2$ is selected from halo, lower straight chain or branched alkyl, and OR$_6$.

In some embodiments of the compounds of Formula I, when m is 0, n is not 0.

In some embodiments of the compounds of Formula I are compounds selected from the group consisting of:

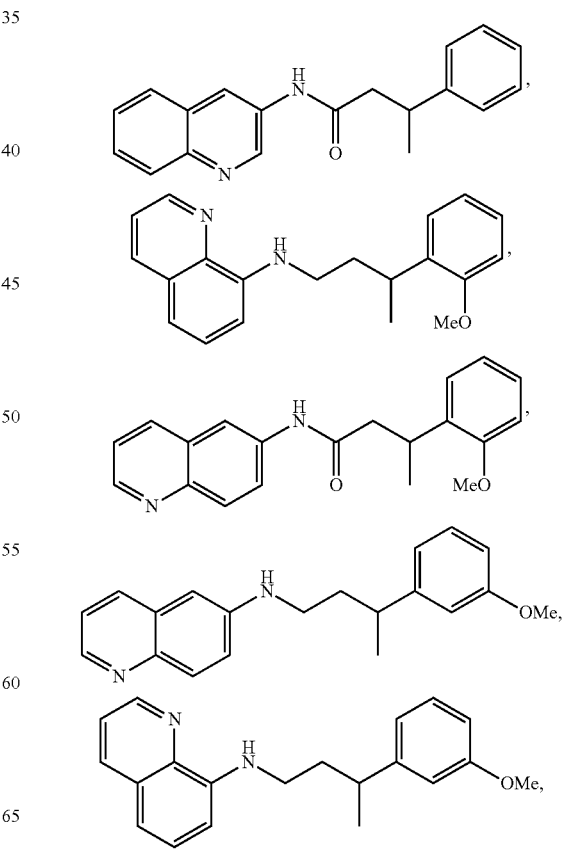

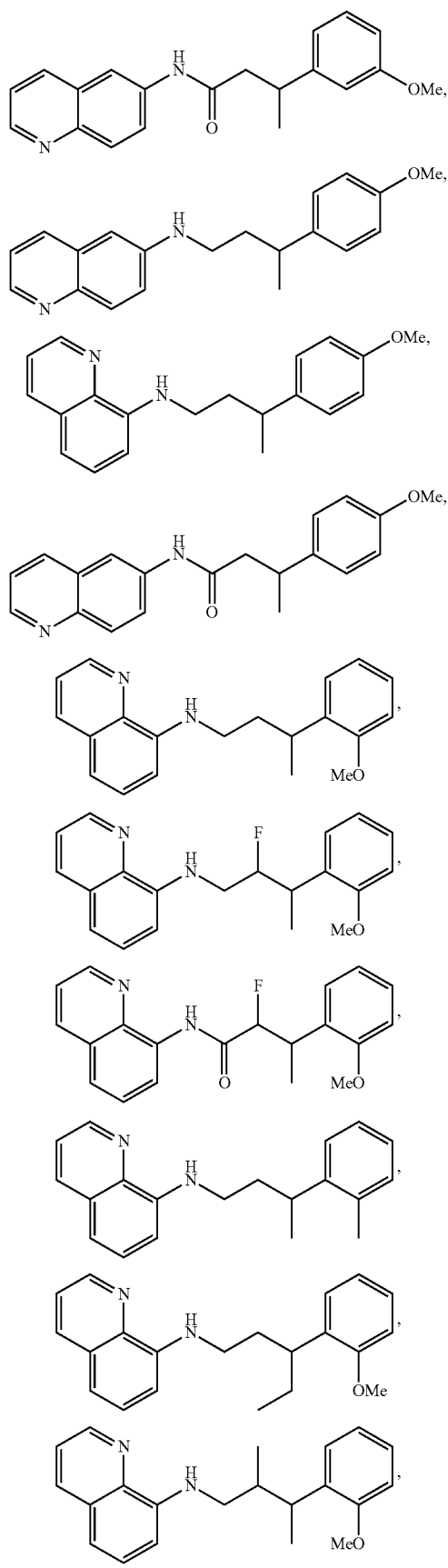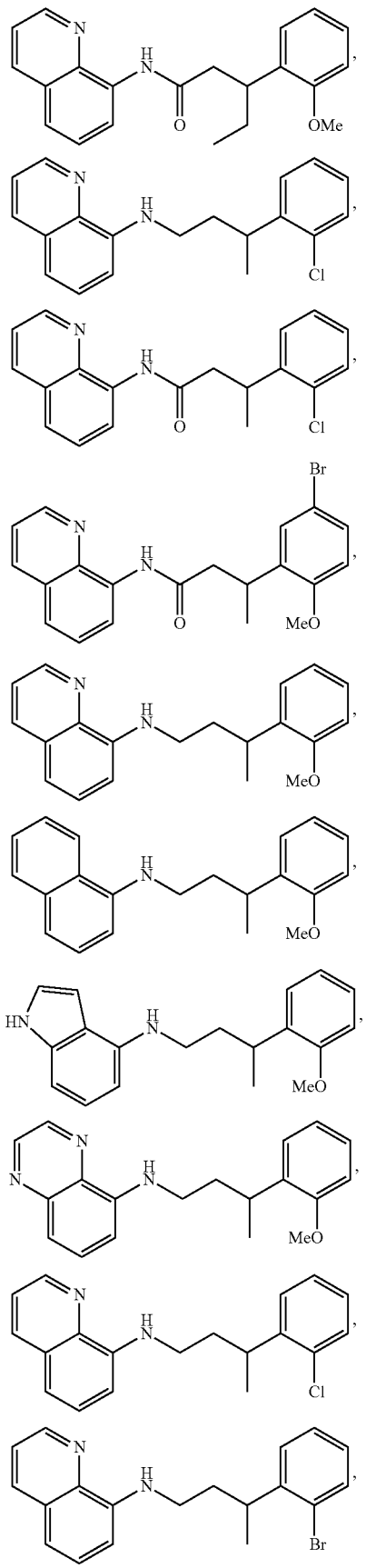

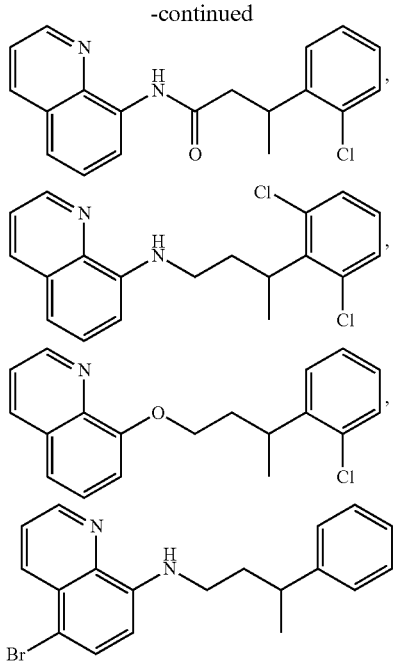

and pharmaceutically acceptable salts thereof.

A compound provided herein, including a pharmaceutically acceptable salt thereof, can be purchased commercially or prepared using known organic synthesis techniques.

The methods provided herein include the manufacture and use of pharmaceutical compositions, which include compounds provided herein and one or more pharmaceutically acceptable carriers. Also provided herein are the compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

A pharmaceutical composition is typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., *Remington: The Science and Practice of Pharmacy,* 21st ed., 2005; and the books in the series *Drugs and the Pharmaceutical Sciences: a Series of Textbooks and Monographs* (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injection can include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. The composition should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate and gelatin.

Sterile injectable solutions can be prepared by incorporating a compound provided herein in the required amount in an appropriate solvent with one or a combination of ingredients enumerated above, as required, followed by filtered sterilization. Generally, dispersions are prepared by incorporating a compound provided herein into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of a compound provided herein plus any additional desired ingredient from a previously sterile-filtered solution thereof.

Oral compositions generally include an inert diluent or an edible carrier. For the purpose of oral therapeutic administration, a compound provided herein can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the compounds provided herein can be formulated into ointments, salves, gels, or creams as generally known in the art.

The pharmaceutical compositions can also be prepared in the form of suppositories (e.g., with conventional suppository bases such as cocoa butter and other glycerides) or retention enemas for rectal delivery.

Additionally, intranasal delivery is possible, as described in, inter alia, Hamajima et al., *Clin. Immunol. Immunopathol.*, 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical composition may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Dosage forms or compositions containing a compound as described herein in the range of 0.005% to 100% with the balance made up from non-toxic carrier may be prepared. Methods for preparation of these compositions are known to those skilled in the art. The contemplated compositions may contain 0.001%-100% of a compound provided herein, in one embodiment 0.1-95%, in another embodiment 75-85%.

The pharmaceutical compositions can be included in a container, pack, or dispenser together with instructions for administration.

As described above, the preparations of one or more compounds provided herein may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. In some embodiments, administration is oral.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrastemal injection, and infusion.

Actual dosage levels of the active ingredients in the pharmaceutical compositions provided herein may be varied so as to obtain an amount of the active ingredient which is effective to achieve the desired therapeutic response for a particular patient, composition, and mode of administration, without being toxic to the patient.

The concentration of a compound provided herein in a pharmaceutically acceptable mixture will vary depending on several factors, including the dosage of the compound to be administered, the pharmacokinetic characteristics of the compound(s) employed, and the route of administration. In some embodiments, the compositions provided herein can be provided in an aqueous solution containing about 0.1-10% w/v of a compound disclosed herein, among other substances, for parenteral administration. Typical dose ranges can include from about 0.01 to about 50 mg/kg of body weight per day, given in 1-4 divided doses. Each divided dose may contain the same or different compounds. The dosage will be a therapeutically effective amount depending on several factors including the overall health of a patient, and the formulation and route of administration of the selected compound(s).

Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses. The amount of active ingredient which can be combined with a carrier material to produce a single dosage form will generally be that amount of the compound which produces a therapeutic effect.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the patient and adjusting the dosage and/or timing.

Also provided herein is a conjoint therapy wherein one or more other therapeutic agents are administered with a compound or a pharmaceutical composition comprising a compound provided herein. Such conjoint treatment may be achieved by way of the simultaneous, sequential, or separate dosing of the individual components of the treatment.

Definitions

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about", whether or not the term is explicitly used, unless explicitly stated otherwise. As used herein, the singular forms "a," "an," and "the" include plural referents unless the context clearly dictates otherwise.

A "subject," as used herein, includes both humans and other animals, particularly mammals. Thus, the methods are applicable to both human therapy and veterinary applications. In some embodiments, the patient is a mammal, for example, a primate. In some embodiments, the patient is a human.

A "therapeutically effective" amount of a compound provided herein is typically one which is sufficient to prevent, eliminate, ameliorate or reduce the symptoms of an HCMV infection. It will be appreciated that different concentrations may be employed for prophylaxis than for treatment of an active disease.

A "virus production inhibiting" amount of a compound provided herein is typically one which is sufficient to achieve a measurable reduction in the amount of virus produced by the cells contacted with the compound. In some embodiments, a "virus production inhibiting" amount is an amount which inhibits a least 30% of the virus production in untreated cells. In some embodiments, a "virus production inhibiting" amount is an amount which inhibits a least 50% of the virus production in untreated cells. In some embodiments, a "virus production inhibiting" amount is an amount which inhibits a least 70% of the virus production in untreated cells. In some embodiments, a "virus production inhibiting" amount is an amount which inhibits a least 90% of the virus production in untreated cells.

The terms "treatment" and "prevention" are art-recognized and include administration of one or more of the compounds or pharmaceutical compositions provided herein. If it is administered prior to clinical manifestation of the unwanted condition (e.g., disease or other unwanted state of the subject) then the treatment is preventative, (i.e., it protects the subject against developing the unwanted condition). As used in this context, the term "prevent" means to slow or prevent the onset of at least one symptom of a disorder as provided herein. For example, such prevention may be prompted by a likelihood of exposure to an infective agent (e.g., a virus) or when a subject exhibits other symptoms that indicate onset of a disorder (e.g., a metabolic disorder or cardiovascular disorder) may be likely. Alternatively, if it is administered after manifestation of the unwanted condition, the treatment is therapeutic, (i.e., it is intended to diminish, ameliorate, or stabilize the existing unwanted condition or side effects thereof). As used in this context, to "treat" means to ameliorate at least one symptom of a disorder as provided herein.

The term, "compound," as used herein is meant to include all stereoisomers, geometric isomers, and tautomers of the structures depicted. Compounds herein identified by name or structure as one particular tautomeric form are intended to include other tautomeric forms unless otherwise specified.

In some embodiments, a compound provided herein, or salt thereof, is substantially isolated. By "substantially isolated" it is meant that the compound is at least partially or substantially separated from the environment in which it was formed or detected. Partial separation can include, for example, a composition enriched in the compound provided herein. Substantial separation can include compositions containing at least about 50%, at least about 60%, at least about 70%, at least about 80%, at least about 90%, at least about 95%, at least about 97%, or at least about 99% by weight of the compound provided herein, or salt thereof. Methods for isolating compounds and their salts are routine in the art.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salt" refers to the relatively non-toxic, inorganic and organic acid addition salts of a compound provided herein. These salts can be prepared in situ during the final isolation and purification of a compound provided herein, or by separately reacting the compound in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", *J. Pharm. Sci.* 66: 1-19.)

In some embodiments, a compound provided herein may contain one or more acidic functional groups and, thus, is capable of forming pharmaceutically acceptable salts with pharmaceutically acceptable bases. The term "pharmaceutically acceptable salts" in these instances refers to the relatively non-toxic inorganic and organic base addition salts of a compound provided herein. These salts can likewise be prepared in situ during the final isolation and purification of the compound, or by separately reacting the purified compound in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

The term "alkyl" as employed herein refers to straight and branched chain aliphatic groups having from 1 to 12 carbon atoms, preferably 1-8 carbon atoms, and more preferably 1-6 carbon atoms, which is optionally substituted with one, two or three substituents. Preferred alkyl groups include, without limitation, methyl, ethyl, propyl, isopropyl, butyl, isobutyl, secbutyl, tertbutyl, pentyl, and hexyl. A "$C_0$" alkyl (as in "$C_0$-$C_3$-alkyl") is a covalent bond (like "$C_0$" hydrocarbyl). The term "lower alkyl" refers to straight and branched chain aliphatic groups having from 1 to 6 carbon atoms. Unless otherwise specified, the term "alkyl" includes alkenyl, alkynyl and cyclic alkyl groups.

The term "alkenyl" as used herein means an unsaturated straight or branched chain aliphatic group with one or more carbon-carbon double bonds, having from 2 to 12 carbon atoms, preferably 2-8 carbon atoms, and more preferably 2-6 carbon atoms, which is optionally substituted with one, two or three substituents. Preferred alkenyl groups include, without limitation, ethenyl, propenyl, butenyl, pentenyl, and hexenyl.

The term "alkynyl" as used herein means an unsaturated straight or branched chain aliphatic group with one or more carbon-carbon triple bonds, having from 2 to 12 carbon atoms, preferably 2-8 carbon atoms, and more preferably 2-6 carbon atoms, which is optionally substituted with one, two or three substituents. Preferred alkynyl groups include, without limitation, ethynyl, propynyl, butynyl, pentynyl, and hexynyl.

The term "heteroalkyl" refers to an alkyl group, as defined herein above, wherein one or more carbon atoms in the chain are replaced by a heteroatom selected from the group consisting of O, S, and N.

An "aryl" group is a $C_6$-$C_{14}$ aromatic moiety comprising one to three aromatic rings, which is optionally substituted. Preferably, the aryl group is a $C_6$-$C_{10}$ aryl group. Preferred aryl groups include, without limitation, phenyl, naphthyl, anthracenyl, and fluorenyl.

A "heterocyclyl" or "heterocyclic" group is a ring structure having from about 3 to about 8 atoms, wherein one or more atoms are selected from the group consisting of N, O, and S. The heterocyclic group is optionally substituted on carbon at one or more positions. The heterocyclic group is also independently optionally substituted on nitrogen with alkyl, aryl, aralkyl, alkylcarbonyl, alkylsulfonyl, arylcarbonyl, arylsulfonyl, alkoxycarbonyl, aralkoxycarbonyl, or on sulfur with oxo or lower alkyl. Preferred heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholino. In certain preferred embodiments, the heterocyclic group is fused to an aryl, heteroaryl, or cycloalkyl group. Examples of such fused heterocyles include, without limitation, tetrahydroquinoline and dihydrobenzofuran. Specifically excluded from the scope of this term are compounds having adjacent annular O and/or S atoms.

As used herein, the term "heteroaryl" refers to groups having 5 to 14 ring atoms, preferably 5, 6, 9, or 10 ring atoms; having 6, 10, or 14 π electrons shared in a cyclic array; and having, in addition to carbon atoms, from one to three heteroatoms per ring selected from the group consisting of N, O, and S. A "heteroaralkyl" or "heteroarylalkyl" group comprises a heteroaryl group covalently linked to an alkyl group, either of which is independently optionally substituted or unsubstituted. Preferred heteroalkyl groups comprise a C1-C6 alkyl group and a heteroaryl group having 5, 6, 9, or 10 ring atoms. Specifically excluded from the scope of this term are compounds having adjacent annular O and/or S atoms. Examples of preferred heteroaralkyl groups include pyridylmethyl, pyridylethyl, pyrrolylmethyl, pyrrolylethyl, imidazolylmethyl, imidazolylethyl, thiazolylmethyl, and thiazolylethyl. Specifically excluded from the scope of this term are compounds having adjacent annular O and/or S atoms.

Embodiments of heterocyclyls and heteroaryls include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

As employed herein, when a moiety (e.g., cycloalkyl, hydrocarbyl, aryl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—) nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups.

The term "halogen" or "halo" as employed herein refers to chlorine, bromine, fluorine, or iodine. As herein employed, the term "acyl" refers to an alkylcarbonyl or arylcarbonyl substituent. The term "acylamino" refers to an amide group attached at the nitrogen atom (i.e., R—CO—NH—). The term "carbamoyl" refers to an amide group attached at the carbonyl carbon atom (i.e., $NH_2$—CO—). The nitrogen atom of an acylamino or carbamoyl substituent is optionally additionally substituted. The term "sulfonamido" refers to a sulfonamide substituent attached by either the sulfur or the nitrogen atom. The term "amino" is meant to include $NH_2$, alkylamino, arylamino, and cyclic amino groups. The term "ureido" as employed herein refers to a substituted or unsubstituted urea moiety.

A moiety that is substituted is one in which one or more hydrogens have been independently replaced with another chemical substituent. As a non-limiting example, substituted phenyls include 2-flurophenyl, 3,4-dichlorophenyl, 3-chloro-4-fluoro-phenyl, 2-fluor-3-propylphenyl. As another non-limiting example, substituted n-octyls include 2,4 dimethyl-5-ethyl-octyl and 3-cyclopentyl-octyl. Included within this definition are methylenes (—$CH_2$—) substituted with oxygen to form carbonyl-CO—).

An "unsubstituted" moiety as defined above (e.g., unsubstituted cycloalkyl, unsubstituted heteroaryl, etc.) means that moiety as defined above that does not have any of the optional substituents for which the definition of the moiety (above) otherwise provides. Thus, for example, while an "aryl" includes phenyl and phenyl substituted with a halo, "unsubstituted aryl" does not include phenyl substituted with a halo.

Synthesis of Compounds of the Invention

The compounds in the present invention (compounds of general Formula I) can be prepared using the general reaction scheme set out in the schemes below.

Scheme 1

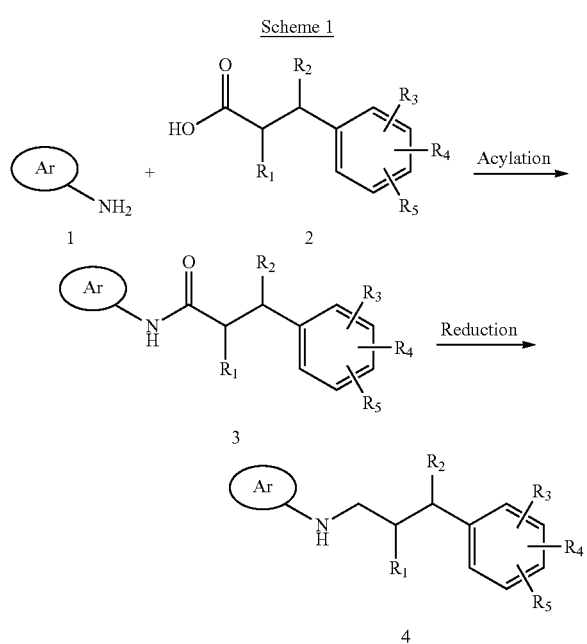

A suitable aryl amine of general formula 1 can be acylated with a suitable carboxylic acid of general formula 2 to provide compounds of general formula 3. The acylation methods include, but are not limited to, standard peptide coupling reagents, treatment with thionyl chloride or treatment with oxalyl chloride. It will be recognized that compounds of general formula 3 are identical to compounds of Formula I when m is 1. Compounds of general formula 3 can be treated with an appropriate reducing agent to provide compounds of general formula 4. Suitable reducing agents include, but are not limited to, lithium aluminum hydride. It will be recognized that compounds of general formula 4 are identical to compounds of Formula I when m is 0. Those skilled in the art will recognize there may be alternate synthetic paths to provide compound of Formula I. One such alternate synthetic path is described in Scheme 2.

Scheme 2

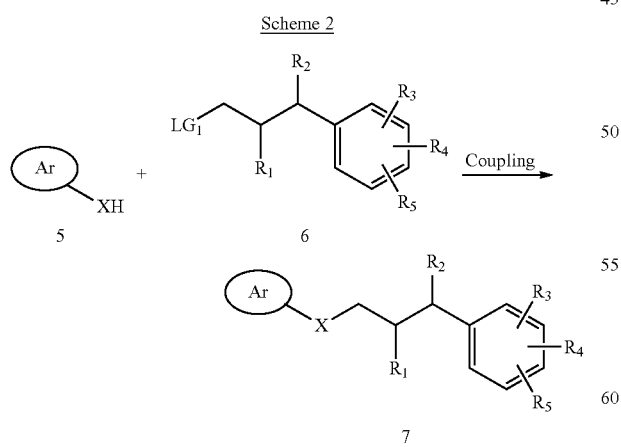

An aryl amine or aryl alcohol of general formula 5 can be reacted with a compound of general formula 6 where $LG_1$ is a suitable leaving group. Suitable leaving groups include, but are not limited to, halo, —OMs, —OTs and the like. It will be recognized that compounds of general formula 7 are identical to compounds of Formula I when m is 0.

Methods to perform the above described reactions and processes would be apparent to those of ordinary skill in the art based on the present disclosure, or can be deduced in analogy from the examples. Starting materials are commercially available or can be made by methods analogous to those described in the Examples below.

EXAMPLES

The invention is further described in the following examples, which do not limit the scope of the invention described in the claims.

Synthesis of Examples 1 and 2

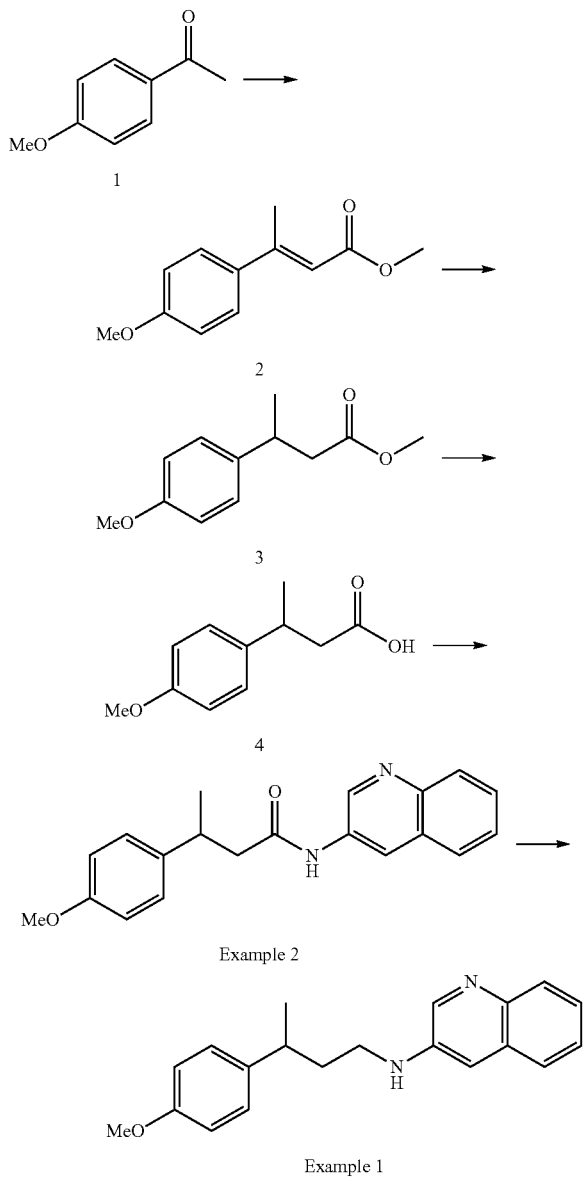 [SMILES: COc1ccc(C(C)=O)cc1 ; COC(=O)/C=C(\C)c1ccc(OC)cc1 ; COC(=O)CC(C)c1ccc(OC)cc1 ; COc1ccc(C(C)CC(=O)O)cc1 ; COc1ccc(C(C)CC(=O)Nc2ccc3ncccc3c2)cc1 ; COc1ccc(C(C)CCNc2ccc3ncccc3c2)cc1]

Procedure:
1. To a solution of Trimethyl phosphonoacetate (7.3 g, 40 mmol) in dry THF (200 mL) was added NaH (1.6 g, 40 mmol, 60%) in portions at 0° C. After the mixture was stirred at RT for 2 hours, a solution of Compound 1 (5 g, 33.3 mmol) in dry THF (10 mL) was added dropwise. The resulting solution was stirred at RT for 1 hour and refluxed for 2 hours. TLC indicated reaction completed. The reaction mixture was diluted with saturated NH$_4$Cl solution and extracted with EA. The organic extracts were washed with water, brine, dried over anhydrous Na$_2$SO$_4$, filtered and concentrated to give a crude oil. The crude product was purified by silica gel chromatography (5% EA/PE~20% EA/PE) to afford Compound 2 (3 g, 44%).

$^1$HNMR (CDCl$_3$, 300 MHz) δ: 7.6-7.4 (d, 2H), 7.0-6.8 (d, 2H), 6.2-6.1 (s, 1H), 4.0-3.7 (d, 6H), 2.7-2.6 (s, 3H).

2. To a solution of Compound 2 (3 g, 14.5 mmol) in THF (50 mL) was added Pd/C (300 mg). The reaction mixture was stirred under H$_2$ balloon at RT overnight. NMR indicated reaction completion. The residue was filtered and the filter cake washed with THF and the filtrate was concentrated to give Compound 3 (3 g, 99%).

$^1$HNMR (CDCl$_3$, 300 MHz) δ: 7.3-7.1 (d, 2H), 7.0-6.8 (d, 2H), 4.0-3.8 (s, 4H), 3.7-3.6 (s, 3H), 3.4-3.1 (m, 1H), 2.8-2.6 (m, 2H), 1.4-1.2 (m, 4H).

3. To a solution of Compound 3 (3 g, 14.4 mmol) in THF/H$_2$O (50 mL, 1:1) was added LiOH.H$_2$O (1.8 g, 43.2 mmol). The reaction mixture was stirred at RT overnight. TLC indicated reaction completion. The solvent was removed in vacuum, and the residue was adjusted to pH=3-4 with 6 N HCl solution at 0° C. Then it was extracted with EA. The organic extracts were washed with brine, dried over anhydrous Na$_2$SO$_4$, filtered and concentrated to give Compound 4 (2.5 g, 89.3%).

$^1$HNMR (CDCl$_3$, 300 MHz) δ: 7.2-7.1 (d, 2H), 6.9-6.8 (d, 2H), 4.2-4.0 (m, 1H), 3.9-3.8 (s, 3H), 3.3-3.1 (m, 1H), 2.1-2.0 (s, 2H), 1.4-1.2 (m, 3H).

4. To a solution of Compound 4 (400 mg, 2 mmol) in DCM (10 mL) were added 3-aminoquinoline (300 mg, 2 mmol), EDCI (760 mg, 4 mmol) and DMAP (80 mg). The reaction mixture was stirred at RT overnight. TLC indicated reaction completion. The residue was treated with water and extracted with DCM. The organic extracts were washed with brine, dried over anhydrous Na$_2$SO$_4$, filtered and concentrated to give a crude oil. The crude product was purified by silica gel chromatography to afford Example 2 (300 mg, 45.5%).

$^1$HNMR (CDCl$_3$, 300 MHz) δ: 8.8-8.7 (s, 1H), 8.5-8.4 (s, 1H), 8.1-8.0 (d, 1H), 7.9-7.8 (d, 1H), 7.7-7.6 (m, 1H), 7.6-7.5 (m, 1H), 7.4-7.2 (m, 4H), 7.1-7.0 (s, 1H), 6.9-6.8 (d, 2H), 3.9-3.7 (s, 3H), 3.4-3.2 (m, 1H), 2.8-2.7 (d, 2H), 1.5-1.3 (s, 3H).

LC-MS: m/z=321 (M+1)+.

5. To a solution of Example 2 (200 mg, 0.6 mmol) in THF (20 mL) were added LAH (120 mg, 3 mmol) portionwise at 0° C. The reaction mixture was stirred at refluxing for 2 hours. TLC indicated reaction completion. After cooling to 0° C., the residue was diluted with water and filtered and the filter cake washed with THF. The filtrate was concentrated and purified by silica gel chromatography to afford Example 1 (39 mg, 19.1%)

$^1$HNMR (CDCl$_3$, 300 MHz) δ: 8.4-8.3 (s, 1H), 8.0-7.9 (s, 1H), 7.6-7.5 (s, 1H), 7.5-7.4 (s, 2H), 7.2-7.1 (d, 2H), 7.0-6.8 (m, 3H), 4.9-4.8 (s, 4H), 3.2-3.0 (s, 2H), 2.9-2.8 (m, 1H), 2.0-1.9 (s, 2H), 1.4-1.2 (m, 4H).

LC-MS: m/z=307 (M+1)$^+$.

Synthesis of Examples 3 and 4

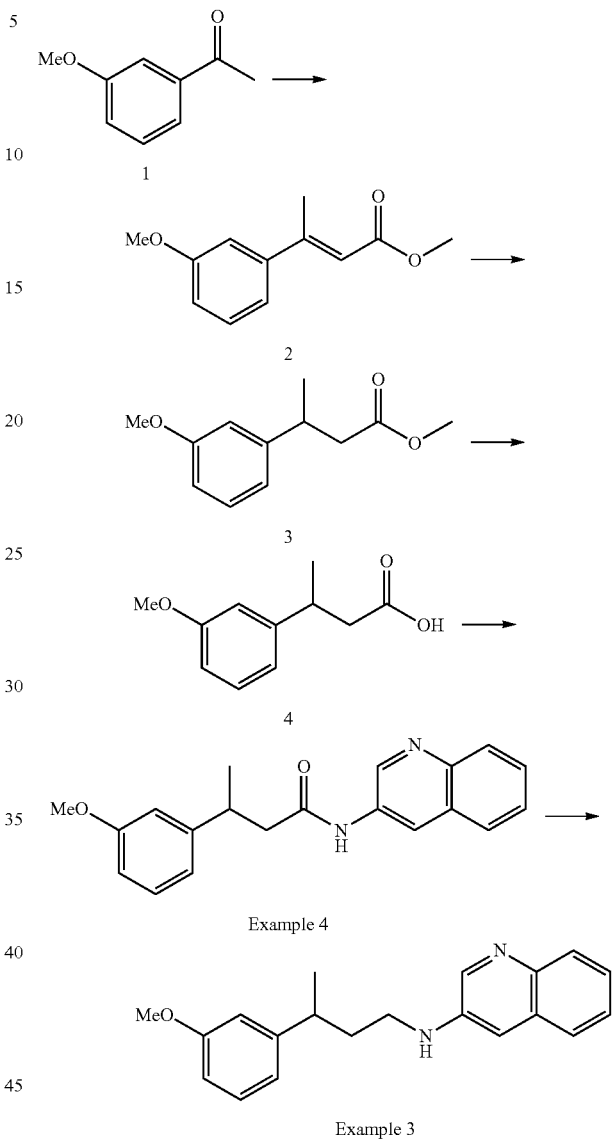

Example 4

Example 3

Procedure:

1. To a solution of Trimethyl phosphonoacetate (7.3 g, 40 mmol) in dry THF (200 mL) was added NaH (1.6 g, 40 mmol, 60%) portionwise at 0° C. After the mixture was stirred for 2 hours at RT, a solution of Compound 1 (5 g, 33.3 mmol) in dry THF (10 mL) was added dropwise. The resulting solution was stirred at RT for 1 hour and refluxed for 2 hours. TLC indicated reaction completion. The reaction mixture was diluted with saturated NH$_4$Cl solution and extracted with EA. The organic extracts were washed with water, brine, dried over anhydrous Na$_2$SO$_4$, filtered and the filtrate concentrated to give a crude oil. The crude product was purified by silica gel chromatography (5% EA/PE~20% EA/PE) to afford Compound 2 (3 g, 44%).

2. To a solution of Compound 2 (3 g, 14.5 mmol) in THF (50 mL) was added Pd/C (300 mg). The reaction mixture was stirred under H$_2$ balloon at RT overnight. NMR indicated reaction completion. The residue was filtered and the filter cake washed with THF and the filtrate was concentrated to give Compound 3 (3 g, 99%).

3. To a solution of Compound 3 (3 g, 14.4 mmol) in THF/H$_2$O (50 mL, 1:1) was added LiOH.H$_2$O (1.8 g, 43.2 mmol). The reaction mixture was stirred at RT overnight. TLC indicated reaction completion. The solvent was removed under vacuum, and the residue was adjusted to pH=3-4 with 6 N HCl solution at 0° C. and the mixture extracted with EA. The organic extracts were washed with brine, dried over anhydrous Na$_2$SO$_4$, filtered and concentrated to give Compound 4 (2.5 g, 89.3%).

4. To a solution of Compound 4 (400 mg, 2 mmol) in DCM (10 mL) were added 3-aminoquinoline (300 mg, 2 mmol), EDCI (760 mg, 4 mmol) and DMAP (80 mg). The reaction mixture was stirred at RT overnight. TLC indicated reaction completion. The residue was treated with water and extracted with DCM. The organic extracts were washed with brine, dried over anhydrous Na$_2$SO$_4$, filtered and concentrated to give a crude oil. The crude product was purified by silica gel chromatography to afford Example 4 (250 mg, 45.5%).

$^1$HNMR (CDCl$_3$, 300 MHz) δ: 1.3-1.5 (d, 3H), 2.6-2.8 (d, 2H), 3.3-3.5 (m, 1H), 3.7-3.8 (d, 3H), 6.7-6.9 (m, 3H), 7.1-7.2 (m, 1H), 7.5-7.6 (m, 1H), 7.6-7.7 (m, 1H), 7.7-7.8 (m, 1H), 7.9-8.1 (d, 1H), 8.4-8.5 (d, 1H), 8.6-8.7 (d, 1H)

LC-MS: m/z=343.2 (M+23)$^+$.

5. To a solution of Example 4 (200 mg, 0.6 mmol) in THF (20 mL) were added LAH (120 mg, 3 mmol) portionwise at 0° C. The reaction mixture was stirred at reflux for 2 hours. TLC indicated reaction completion. After cooling to 0° C., the residue was diluted with water and filtered and the filter cake washed with THF. The filtrate was concentrated and purified by silica gel chromatography to afford Example 3 (25 mg, 21.1%)

$^1$HNMR (CDCl$_3$, 300 MHz) δ: 1.2-1.4 (d, 3H), 1.9-2.0 (d, 2H), 2.8-3.0 (d, 1H), 3.1-3.3 (d, 2H), 3.6-3.9 (d, 3H), 6.7-6.9 (d, 4H), 7.2-7.3 (d, 2H), 7.3-7.4 (d, 2H), 7.5-7.6 (d, 1H), 7.9-8.0 (d, 1H), 8.3-8.4 (d, 1H)

LC-MS: m/z=307.2 (M+1)$^+$.

Synthesis of Examples 5 and 6

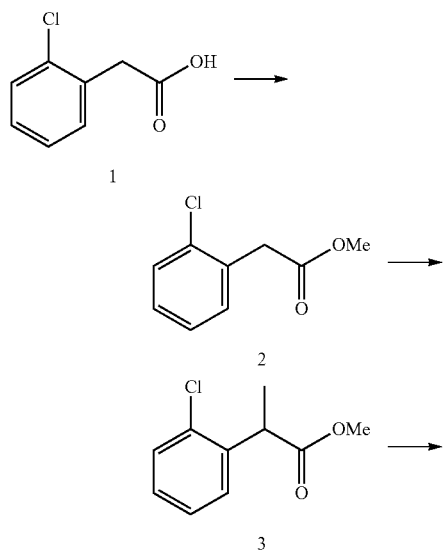

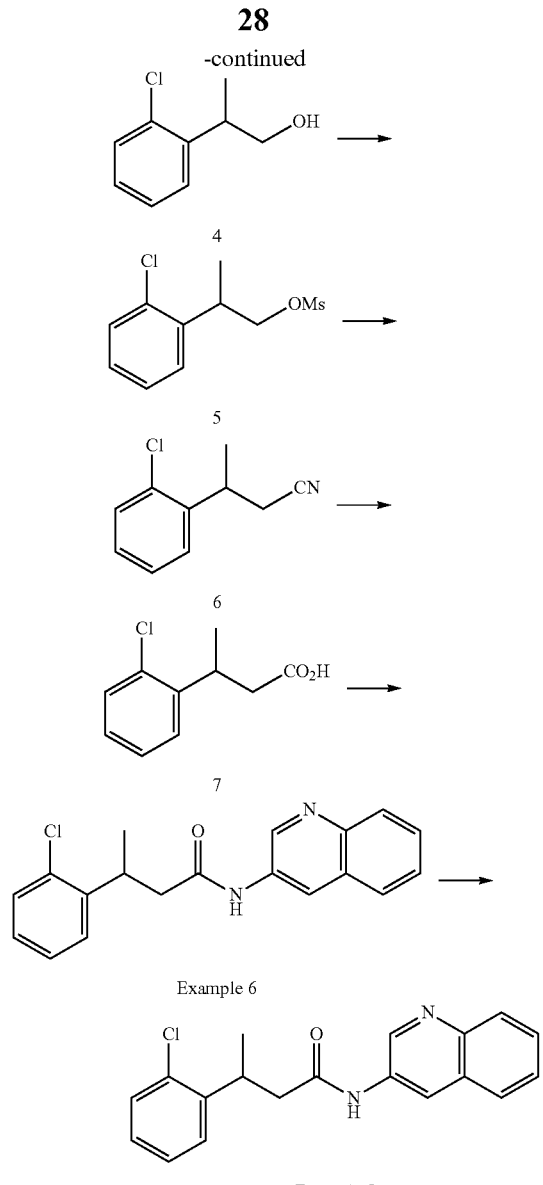

Procedure:

1. To a solution of Compound 1 (20 g, 117.6 mmol) in MeOH (100 mL) was added SOCl$_2$ (10 mL) dropwise at 0° C. The resulting solution was stirred at reflux overnight. TLC indicated reaction completion. The solvent was removed in vacuum, and the residue was treated with water and extracted with EA. The organic extracts were washed with saturated NaHCO$_3$ solution, brine, dried over anhydrous Na$_2$SO$_4$, filtered and concentrated to give Compound 2 (21 g, 97.2%).

2. To a solution of i-Pr$_2$NH (20 mL, 136.5 mmol) in dry THF (100 mL) was added n-BuLi (54.6 mL, 136.5 mmol) dropwise at −78° C. under N$_2$ and stirred for 30 min. Then a solution of Compound 2 (21 g, 113.7 mmol) in dry THF (100 mL) was added dropwise and stirred at −78° C. for 1 hour. CH$_3$I (24.2 g, 170.6 mmol) was added. The resulting solution was stirred at RT overnight. The residue was treated with water and extracted with EA. The organic extracts were washed with saturated water, brine, dried over anhydrous Na$_2$SO$_4$, filtered and concentrated to give Compound 3 (21 g, 93%).

3. To a suspension mixture of LAH (4 g, 106 mmol) in dry THF (150 mL) was added a solution of Compound 3 (21 g, 106 mmol) in dry THF (50 mL) dropwise at 0° C. under $N_2$. The reaction mixture was heated to reflux for 2 hours. TLC indicated reaction completion. After cooling to 0° C., the residue was diluted with water and filtered and the filter cake washed with THF. The filtrate was concentrated and purified by silica gel chromatography to afford Compound 4 (15 g, 83.3 mmol).

4. To a solution of Compound 4 (5 g, 33.3 mmol) in DCM (50 mL) was added TEA (6.8 g, 66.6 mmol), then MsCl (4.6 g, 40 mmol) was added dropwise at 0° C. The reaction mixture was stirred at RT for 2 hours. TLC indicated reaction completion. The residue was treated with water and extracted with DCM. The organic extracts were washed with brine, dried over anhydrous $Na_2SO_4$, filtered and concentrated to give Compound 5 (7 g, 95%).

5. To a solution of Compound 5 (7 g, 28.2 mmol) in MeCN (30 mL) was added TMSCN (4.5 g, 45.3 mmol) at 0° C., and then a solution of TBAF (11.5 g, 36.3 mmol) in dry THF (30 mL) was added dropwise. The reaction mixture was heated to 80° C. overnight. TLC indicated reaction completion. The solvent was removed in vacuum, and the residue was treated with water and extracted with EA. The organic extracts were washed with water, brine, dried over anhydrous $Na_2SO_4$, filtered and concentrated to give a crude oil. The crude product was purified by silica gel chromatography to afford Compound 6 (4 g, 80%).

6. To a solution of Compound 6 (4 g, 22.3 mmol) in EtOH (40 mL) was added 10% NaOH solution (40 mL). The reaction mixture was stirred at 90° C. overnight. TLC indicated reaction completion. The solvent was removed in vacuum, and the residue was treated with water and extracted with DCM. The organic extracts were washed with water, brine, dried over anhydrous $Na_2SO_4$, filtered and concentrated to give Compound 7 (3.5 g, 79.5%).

7. To a solution of Compound 7 (500 mg, 2.5 mmol) in DCM (10 mL) were added 3-aminoquinoline (300 mg, 2 mmol), EDCI (760 mg, 4 mmol) and DMAP (80 mg). The reaction mixture was stirred at RT overnight. TLC indicated reaction completion. The residue was treated with water and extracted with DCM. The organic extracts were washed with brine, dried over anhydrous $Na_2SO_4$, filtered and concentrated to give a crude oil. The crude product was purified by silica gel chromatography to afford Example 6 (300 mg, 45.5%).

$^1$HNMR (CDCl$_3$, 300 MHz) δ: 1.3-1.4 (d, 3H), 2.6-2.7 (m, 1H), 2.8-2.9 (m, 1H), 3.8-4.0 (m, 1H), 7.1-7.2 (m, 1H), 7.2-7.4 (m, 3H), 7.4-7.6 (m, 3H), 7.7-7.8 (d, 1H), 7.9-8.0 (d, 1H), 8.5-8.6 (d, 1H), 8.7-8.8 (d, 1H)

LC-MS: m/z=325.2 (M+1)$^+$.

8. To a solution of Example 6 (200 mg, 0.6 mmol) in THF (20 mL) were added LAH (120 mg, 3 mmol) portionwise at 0° C. The reaction mixture was stirred at refluxing for 2 hours. TLC indicated reaction completion. After cooling to 0° C., the residue was diluted with water and filtered and the filter cake washed with THF. The filtrate was concentrated and purified by silica gel chromatography to afford Example 5 (28 mg, 15.1%)

$^1$HNMR (CDCl$_3$, 300 MHz) δ: 1.1-1.4 (m, 3H), 1.9-2.1 (m, 2H), 3.1-3.3 (d, 2H), 3.5-3.69 (m, 1H), 3.9-4.0 (m, 1H), 6.8-6.9 (d, 1H), 7.1-7.2 (d, 1H), 7.2-7.3 (d, 3H), 7.3-7.4 (m, 3H), 7.5-7.6 (m, 1H), 7.9-8.0 (d, 1H), 8.3-8.4 (d, 1H).

LC-MS: m/z=311.2 (M+1)$^+$.

Synthesis of Examples 7 and 8

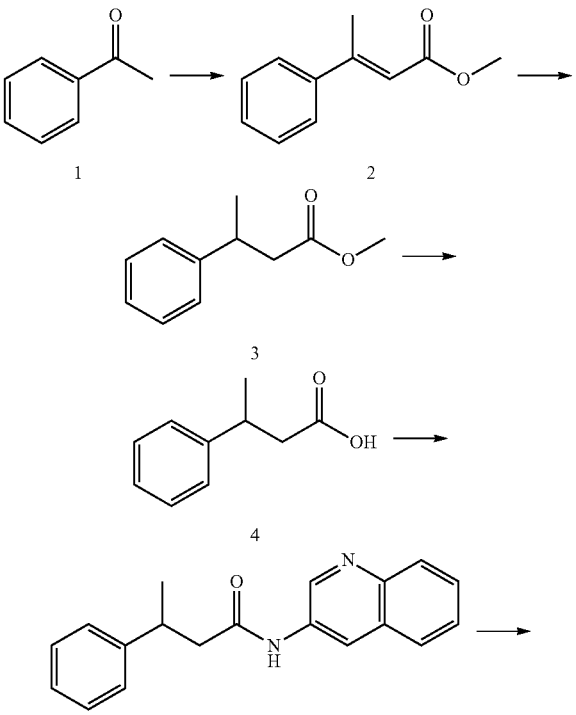

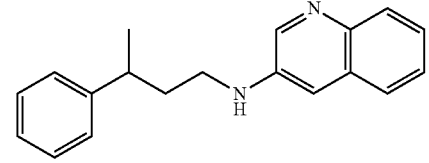

Example 7

Procedure:

1. To a solution of Trimethyl phosphonoacetate (9.1 g, 50 mmol) in dry THF (200 mL) was added NaH (2.0 g, 50 mmol, 60%) portionwise at 0° C. After the mixture was stirred at RT for 2 hours, a solution of Compound 1 (5 g, 41.67 mmol) in dry THF (10 mL) was added dropwise. The resulting solution was stirred at RT for 1 hour and reflux for 2 hours. TLC indicated reaction completion. The reaction mixture was diluted with saturated NH$_4$Cl solution and extracted with EA. The organic extracts were washed with water, brine, dried over anhydrous Na$_2$SO$_4$, filtered and concentrated to give a crude oil. The crude product was purified by silica gel chromatography (5% EA/PE~20% EA/PE) to afford Compound 2 (1.5 g).

$^1$HNMR (CDCl$_3$, 300 MHz) δ: 2.6 (s, 3H), 3.7 (s, 3H), 6.1 (s, 3H), 7.3-7.6 (m, 5H).

2. To a solution of Compound 2 (1.5 g, 8.5 mmol) in THF (50 mL) was added Pd/C (300 mg). The reaction mixture was stirred under H$_2$ balloon at RT overnight. NMR indicated reaction completion. The residue was filtered and the filter cake washed with THF and the filtrate was concentrated to give Compound 3 (1.2 g).

$^1$HNMR (CDCl$_3$, 300 MHz) δ: 1.3 (d, 3H), 2.5 (m, 2H), 3.2 (m, 1H), 3.6 (s, 3H), 7.1-7.4 (m, 5H).

3. To a solution of Compound 3 (1.2 g, 6.7 mmol) in THF/H$_2$O (30 mL, 1:1) was added LiOH.H$_2$O (0.84 g, 20 mmol). The reaction mixture was stirred at RT overnight. TLC indicated reaction completion. The solution was removed in vacuum, and the residue was adjusted to pH=3-4 with 6 N HCl solution at 0° C. and extracted with EA. The organic extracts were washed with brine, dried over anhydrous $Na_2SO_4$, filtered and concentrated to give Compound 4 (800 mg).

$^1$HNMR (CDCl$_3$, 300 MHz) δ: 1.3 (d, 3H), 2.6 (m, 2H), 3.2 (m, 1H), 7.1-7.4 (m, 5H).

4. To a solution of Compound 4 (700 mg, 4.88 mmol) in DCM (20 mL) were added Compound 5 (800 mg, 4.88 mmol), EDCI (1.87 g, 9.76 mmol) and DMAP (50 mg). The reaction mixture was stirred at RT overnight. TLC indicated reaction completion. The residue was treated with water and extracted with DCM. The organic extracts were washed with brine, dried over anhydrous $Na_2SO_4$, filtered and concentrated to give a crude oil. The crude product was purified by silica gel chromatography to afford Example 8 (500 mg).

$^1$HNMR (CDCl$_3$, 300 MHz) δ: 1.4 (d, 3H), 2.7 (d, 2H), 3.4 (m, 1H), 7.2-7.4 (m, 5H), 7.4-7.6 (m, 2H), 7.7 (d, 1H), 8.0 (d, 1H), 8.4 (s, 1H), 8.6 (s, 1H).

LC-MS: m/z=291 (M+1)$^+$.

5. To a solution of Example 8 (400 mg, 1.38 mmol) in THF (20 mL) were added LAH (260 mg, 6.9 mmol) portionwise at 0° C. The reaction mixture was stirred at reflux for 2 hours. TLC indicated reaction completion. After cooling to 0° C. the residue was diluted with water and filtered and the filter cake washed with THF. The filtrate was concentrated and purified by silica gel chromatography to afford Example 7 (15 mg)

$^1$HNMR (CDCl$_3$, 300 MHz) δ: 1.3 (m, 3H), 2.0 (m, 2H), 2.9 (m, 1H), 3.1 (m, 2H), 4.3 (t, 1H), 6.8 (s, 1H), 7.2-7.4 (m, 5H), 7.5 (m, 2H), 7.7 (d, 1H), 7.9 (d, 1H), 8.4 (s, 1H), 8.3 (s, 1H).

LC-MS: m/z=277 (M+1)$^+$.

Synthesis of Examples 9 and 10

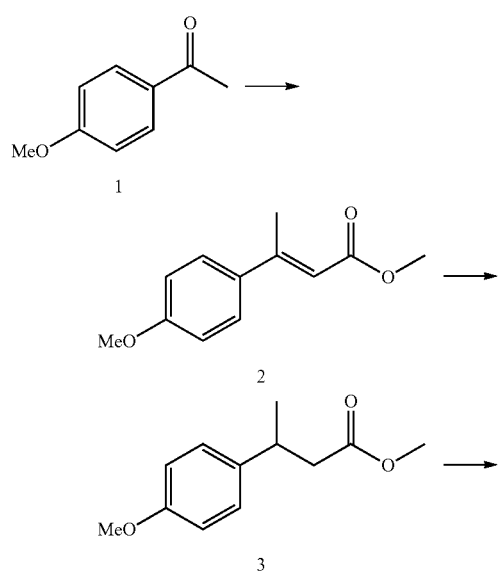

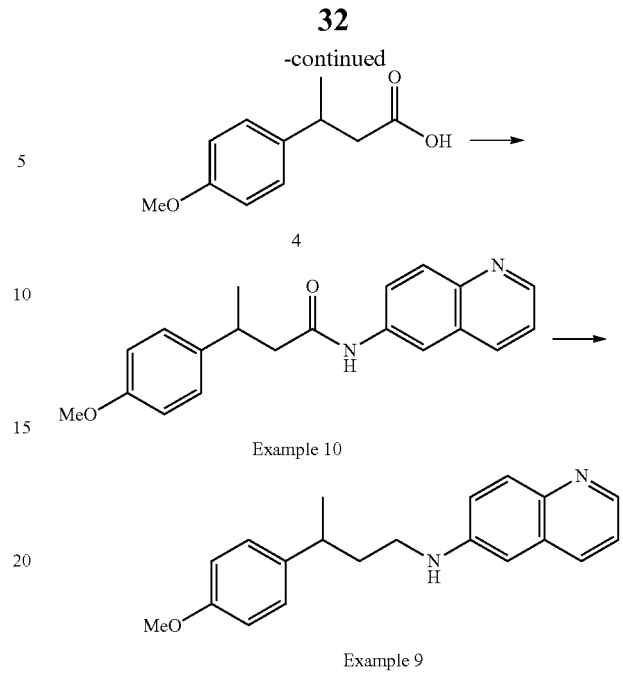

Example 10

Example 9

Procedure:

1. To a solution of Trimethyl phosphonoacetate (7.3 g, 40 mmol) in dry THF (200 mL) was added NaH (1.6 g, 40 mmol, 60%) portionwise at 0° C. After the mixture was stirred at RT for 2 hours, a solution of Compound 1 (5 g, 33.3 mmol) in dry THF (10 mL) was added dropwise. The resulting solution was stirred at RT for 1 hour and refluxed for 2 hours. TLC indicated reaction completion. The reaction mixture was diluted with saturated NH$_4$Cl solution and extracted with EA. The organic extracts were washed with water, brine, dried over anhydrous $Na_2SO_4$, filtered and concentrated to give a crude oil. The crude product was purified by silica gel chromatography (5% EA/PE~20% EA/PE) to afford Compound 2 (3 g, 44%).

$^1$HNMR (CDCl$_3$, 300 MHz) δ: 7.6-7.4 (d, 2H), 7.0-6.8 (d, 2H), 6.2-6.1 (s, 1H), 4.0-3.7 (d, 6H), 2.7-2.6 (s, 3H).

2. To a solution of Compound 2 (3 g, 14.5 mmol) in THF (50 mL) was added Pd/C (300 mg). The reaction mixture was stirred under H$_2$ balloon at RT overnight. NMR indicated reaction completion. The residue was filtered and the filter cake washed with THF and the filtrate was concentrated to give Compound 3 (3 g, 99%).

$^1$HNMR (CDCl$_3$, 300 MHz) δ: 7.3-7.1 (d, 2H), 7.0-6.8 (d, 2H), 4.0-3.8 (s, 4H), 3.7-3.6 (s, 3H), 3.4-3.1 (m, 1H), 2.8-2.6 (m, 2H), 1.4-1.2 (m, 4H).

3. To a solution of Compound 3 (3 g, 14.4 mmol) in THF/H$_2$O (50 mL, 1:1) was added LiOH.H$_2$O (1.8 g, 43.2 mmol). The reaction mixture was stirred at RT overnight. TLC indicated reaction completion. The solution was removed in vacuum, and the residue was adjusted to pH=3-4 with 6 N HCl solution at 0° C. and extracted with EA. The organic extracts were washed with brine, dried over anhydrous $Na_2SO_4$, filtered and concentrated to give Compound 4 (2.5 g, 89.3%).

$^1$HNMR (CDCl$_3$, 300 MHz) δ: 7.2-7.1 (d, 2H), 6.9-6.8 (d, 2H), 4.2-4.0 (m, 1H), 3.9-3.8 (s, 3H), 3.3-3.1 (m, 1H), 2.1-2.0 (s, 2H), 1.4-1.2 (m, 3H).

4. To a solution of Compound 4 (400 mg, 2 mmol) in DCM (10 mL) were added 6-aminoquinoline (300 mg, 2 mmol), EDCI (760 mg, 4 mmol) and DMAP (80 mg). The reaction mixture was stirred at RT overnight. TLC indicated reaction completion. The residue was treated with water and extracted with DCM. The organic extracts were washed with brine, dried over anhydrous $Na_2SO_4$, filtered and concentrated to give a crude oil. The crude product was purified by silica gel chromatography to afford Example 10 (300 mg, 45.5%).

$^1$HNMR (CDCl$_3$, 300 MHz) δ: 8.9-8.8 (s, 1H), 8.3-8.2 (s, 1H), 8.2-8.1 (m, 1H), 8.1-7.9 (d, 1H), 7.6-7.5 (m, 1H), 7.4-7.2 (m, 7H), 7.1-7.0 (s, 1H), 6.9-6.8 (d, 2H), 3.9-3.8 (s, 3H), 3.5-3.4 (m, 1H), 2.7-2.6 (m, 2H), 1.5-1.3 (m, 3H).

LC-MS: m/z=321 (M+1)$^+$.

5. To a solution of Example 10 (300 mg, 0.6 mmol) in THF (20 mL) were added LAH (120 mg, 3 mmol) portionwise at 0° C. The reaction mixture was stirred at reflux for 2 hours. TLC indicated reaction completion. After cooling to 0° C., the residue was diluted with water and filtered and the filter cake washed with THF. The filtrate was concentrated and purified by silica gel chromatography to afford Example 9 (212 mg, 74.1%)

$^1$HNMR (CDCl$_3$, 300 MHz) δ: 8.7-8.6 (s, 1H), 8.0-7.8 (m, 2H), 7.4-7.1 (m, 4H), 7.1-6.8 (m, 3H), 7.6-7.5 (s, 1H), 4.0-3.8 (s, 4H), 3.2-3.0 (s, 2H), 2.9-2.8 (s, 1H), 2.0-1.9 (s, 2H), 1.4-1.2 (d, 3H).

LC-MS: m/z=307 (M+1)$^+$.

Synthesis of Examples 11 and 12

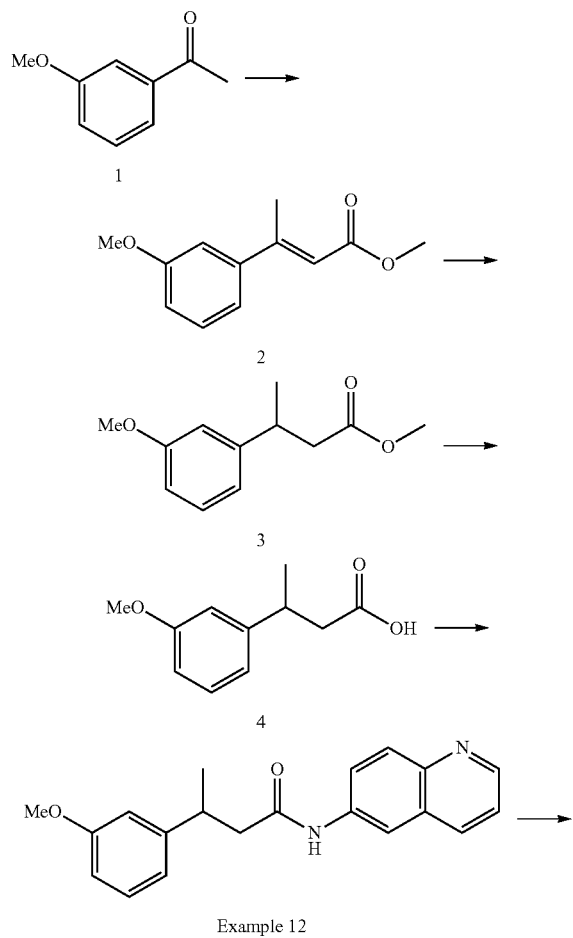

Example 12

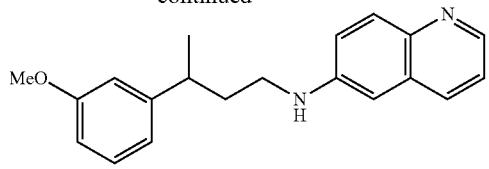

Example 11

Procedure:

1. To a solution of Trimethyl phosphonoacetate (7.3 g, 40 mmol) in dry THF (200 mL) was added NaH (1.6 g, 40 mmol, 60%) portionwise at 0° C. After the mixture was stirred at RT for 2 hours, a solution of Compound 1 (5 g, 33.3 mmol) in dry THF (10 mL) was added dropwise. The resulting solution was stirred at RT for 1 hour and refluxed for 2 hours. TLC indicated reaction completion. The reaction mixture was diluted with saturated NH$_4$Cl solution and extracted with EA. The organic extracts were washed with water, brine, dried over anhydrous $Na_2SO_4$, filtered and concentrated to give a crude oil. The crude product was purified by silica gel chromatography (5% EA/PE~20% EA/PE) to afford Compound 2 (3 g, 44%).

2. To a solution of Compound 2 (3 g, 14.5 mmol) in THF (50 mL) was added Pd/C (300 mg). The reaction mixture was stirred under H$_2$ balloon at RT overnight. NMR indicated reaction completion. The residue was filtered and the filter cake washed with THF and the filtrate was concentrated to give Compound 3 (3 g, 99%).

3. To a solution of Compound 3 (3 g, 14.4 mmol) in THF/H$_2$O (50 mL, 1:1) was added LiOH.H$_2$O (1.8 g, 43.2 mmol). The reaction mixture was stirred at RT overnight. TLC indicated reaction completion. The solution was removed in vacuum, and the residue was adjusted to pH=3-4 with 6 N HCl solution at 0° C. and extracted with EA. The organic extracts were washed with brine, dried over anhydrous $Na_2SO_4$, filtered and concentrated to give Compound 4 (2.5 g, 89.3%).

4. To a solution of Compound 4 (400 mg, 2 mmol) in DCM (10 mL) were added 6-aminoquinoline (300 mg, 2 mmol), EDCI (760 mg, 4 mmol) and DMAP (80 mg). The reaction mixture was stirred at RT overnight. TLC indicated reaction completion. The residue was treated with water and extracted with DCM. The organic extracts were washed with brine, dried over anhydrous $Na_2SO_4$, filtered and concentrated to give a crude oil. The crude product was purified by silica gel chromatography to afford Example 12 (300 mg, 45.5%).

$^1$HNMR (CDCl$_3$, 300 MHz) δ: 1.3-1.4 (d, 2H), 2.6-2.7 (t, 2H), 3.3-3.4 (m, 1H), 3.7-3.9 (d, 3H), 6.7-6.9 (m, 3H), 7.1-7.2 (d, 1H), 7.2-7.4 (m, 4H), 7.9-8.0 (d, 1H), 8.0-8.1 (d, 1H), 8.2-8.3 (d, 1H), 8.7-8.9 (d, 1H)

LC-MS: m/z=343.2 (M+23)$^+$.

5. To a solution of Example 12 (250 mg, 0.8 mmol) in THF (20 mL) were added LAH (120 mg, 3 mmol) portionwise at 0° C. The reaction mixture was stirred at reflux for 2 hours. TLC indicated reaction completion. After cooling to 0° C., the residue was diluted with water and filtered and the filter cake washed with THF. The filtrate was concentrated and purified by silica gel chromatography to afford Example 11 (40 mg, 21.1%)

$^1$HNMR (CDCl$_3$, 300 MHz) δ: 1.2-1.4 (d, 3H), 1.9-2.0 (t, 2H), 2.8-2.9 (t, 1H), 3.0-3.2 (d, 2H), 3.7-3.9 (d, 4H), 6.5-6.6 (d, 1H), 6.7-6.9 (m, 3H), 6.9-7.0 (t, 1H), 7.2-7.3 (d, 3H), 7.7-7.9 (m, 2H), 8.5-8.6 (m, 1H)

LC-MS: m/z=307.2 (M+1)$^+$.

Synthesis of Examples 13 and 14

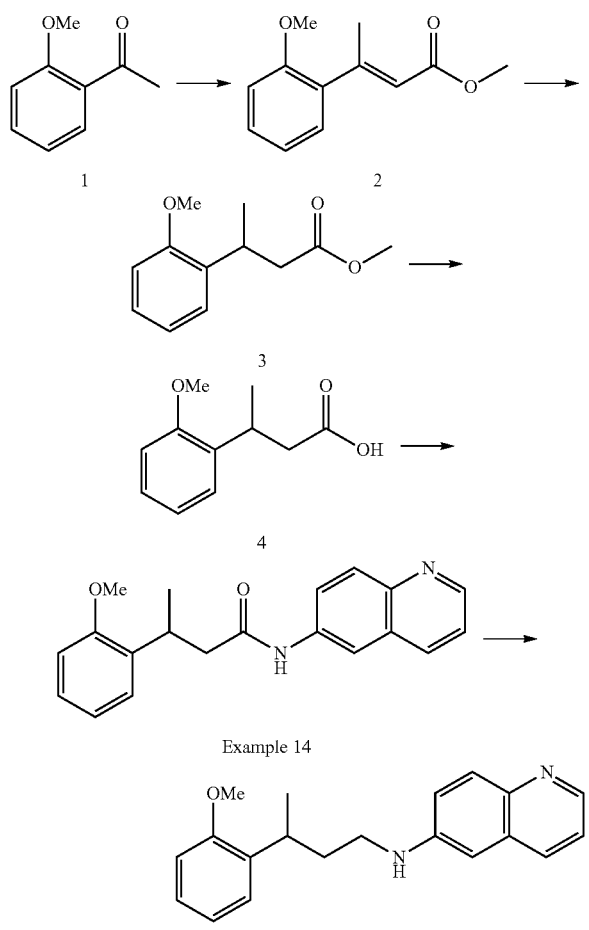

Example 14

Example 13

Procedure:

1. To a solution of Trimethyl phosphonoacetate (14.6 g, 80 mmol) in dry THF (350 mL) was added NaH (3.2 g, 80 mmol, 60%) portionwise at 0° C. After the mixture was stirred at RT for 2 hours, a solution of Compound 1 (10 g, 66.6 mmol) in dry THF (20 mL) was added dropwise. The resulting solution was stirred at RT for 1 hour and refluxed for 2 hours. TLC indicated reaction completion. The reaction mixture was diluted with saturated NH$_4$Cl solution and extracted with EA. The organic extracts were washed with water, brine, dried over anhydrous Na$_2$SO$_4$, filtered and concentrated to give a crude oil. The crude product was purified by silica gel chromatography (5% EA/PE~20% EA/PE) to afford Compound 2 (5.5 g).

$^1$HNMR (CDCl$_3$, 300 MHz) δ: 2.5 (s, 3H), 3.7-3.9 (d, 6H), 5.9 (s, 1H), 6.9 (m, 2H), 7.1-(d, 1H), 7.3 (m, 1H).

2. To a solution of Compound 2 (5.5 g, 26.7 mmol) in THF (80 mL) was added Pd/C (500 mg). The reaction mixture was stirred under H$_2$ balloon at RT overnight. NMR indicated reaction completion. The residue was filtered and the filter cake washed with THF and the filtrate was concentrated to give Compound 3 (5.5 g).

$^1$HNMR (CDCl$_3$, 300 MHz) δ: 1.2 (d, 3H), 2.4-2.7 (m, 2H), 3.6 (s, 3H), 3.9 (s, 3H), 6.9 (m, 2H), 7.1-7.3 (m, 2H).

3. To a solution of Compound 3 (5.5 g, 26.7 mmol) in THF/H$_2$O (100 mL, 1:1) was added LiOH.H$_2$O (3.36 g, 80 mmol). The reaction mixture was stirred at RT overnight. TLC indicated reaction completion. The solution was removed in vacuum, and the residue was adjusted to pH=3-4 with 6 N HCl solution at 0° C. and extracted with EA. The organic extracts were washed with brine, dried over anhydrous Na$_2$SO$_4$, filtered and concentrated to give Compound 4 (4.7 g).

4. To a solution of Compound 4 (500 mg, 2.57 mmol) in DCM (10 mL) were added 6-aminoquinoline (370 mg, 2.57 mmol), EDCI (1 g, 5.14 mmol) and DMAP (80 mg). The reaction mixture was stirred at RT overnight. TLC indicated reaction completion. The residue was treated with water and extracted with DCM. The organic extracts were washed with brine, dried over anhydrous Na$_2$SO$_4$, filtered and concentrated to give a crude oil. The crude product was purified by silica gel chromatography to afford Example 14 (350 mg).

$^1$HNMR (CDCl$_3$, 300 MHz) δ: 1.4 (d, 3H), 2.6-2.9 (m, 2H), 3.7-3.9 (m, 4H), 6.9-7.0 (m, 2H), 7.2-7.4 (m, 4H), 7.9-8.1 (m, 2H), 8.3 (d, 1H). 8.8 (d, 1H).

LC-MS: m/z=321 (M+1)$^+$.

5. To a solution of Example 14 (320 mg, 1 mmol) in THF (10 mL) were added LAH (190 mg, 5 mmol) portionwise at 0° C. The reaction mixture was stirred at reflux for 2 hours. TLC indicated reaction completion. After cooling to 0° C., the residue was diluted with water and filtered and the filter cake washed with THF. The filtrate was concentrated and purified by silica gel chromatography to afford Example 13 (120 mg)

$^1$HNMR (CDCl$_3$, 300 MHz) δ: 1.2 (d, 3H), 2.0 (m, 2H), 3.2 (m, 2H), 3.5 (m, 1H), 3.8 (s, 3H), 4.1 (m, 1H), 6.6 (d, 1H), 6.9 (m, 3H), 7.0 (m, 4H), 7.9 (m, 1H), 8.6 (d, 1H).

LC-MS: m/z=307.2 (M+1)$^+$.

Synthesis of Examples 15 and 16

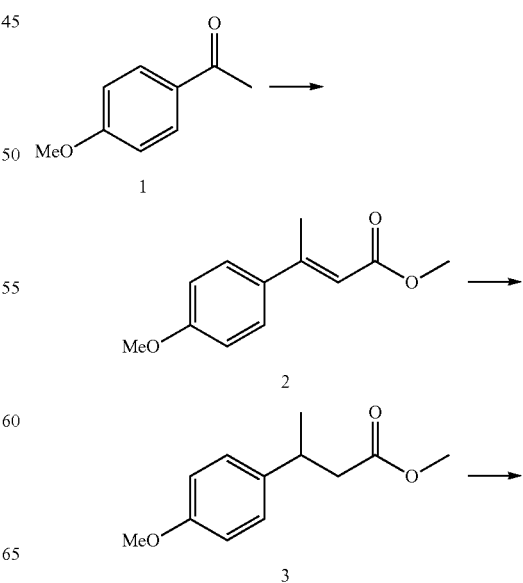

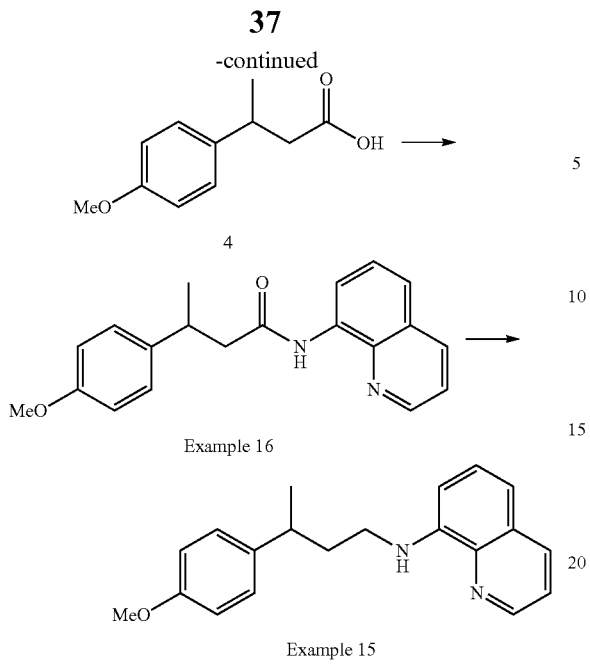

Example 16

Example 15

Procedure:
1. To a solution of Trimethyl phosphonoacetate (7.3 g, 40 mmol) in dry THF (200 mL) was added NaH (1.6 g, 40 mmol, 60%) portionwise at 0° C. After the mixture was stirred at RT for 2 hours, a solution of Compound 1 (5 g, 33.3 mmol) in dry THF (10 mL) was added dropwise. The resulting solution was stirred at RT for 1 hour and reflux for 2 hours. TLC indicated reaction completion. The reaction mixture was diluted with saturated $NH_4Cl$ solution and extracted with EA. The organic extracts were washed with water, brine, dried over anhydrous $Na_2SO_4$, filtered and concentrated to give a crude oil.

The crude product was purified by silica gel chromatography (5% EA/PE~20% EA/PE) to afford Compound 2 (3 g, 44%).

$^1$HNMR ($CDCl_3$, 300 MHz) δ: 7.6-7.4 (d, 2H), 7.0-6.8 (d, 2H), 6.2-6.1 (s, 1H), 4.0-3.7 (d, 6H), 2.7-2.6 (s, 3H).

2. To a solution of Compound 2 (3 g, 14.5 mmol) in THF (50 mL) was added Pd/C (300 mg). The reaction mixture was stirred under $H_2$ balloon at RT overnight. NMR indicated reaction completion. The residue was filtered and the filter cake washed with THF and the filtrate was concentrated to give Compound 3 (3 g, 99%).

$^1$HNMR ($CDCl_3$, 300 MHz) δ: 7.3-7.1 (d, 2H), 7.0-6.8 (d, 2H), 4.0-3.8 (s, 4H), 3.7-3.6 (s, 3H), 3.4-3.1 (m, 1H), 2.8-2.6 (m, 2H), 1.4-1.2 (m, 4H).

3. To a solution of Compound 3 (3 g, 14.4 mmol) in $THF/H_2O$ (50 mL, 1:1) was added $LiOH·H_2O$ (1.8 g, 43.2 mmol). The reaction mixture was stirred at RT overnight. TLC indicated reaction completion. The solution was removed in vacuum, and the residue was adjusted to pH=3-4 with 6 N HCl solution at 0° C. and extracted with EA. The organic extracts were washed with brine, dried over anhydrous $Na_2SO_4$, filtered and concentrated to give Compound 4 (2.5 g, 89.3%)

$^1$HNMR ($CDCl_3$, 300 MHz) δ: 7.2-7.1 (d, 2H), 6.9-6.8 (d, 2H), 4.2-4.0 (m, 1H), 3.9-3.8 (s, 3H), 3.3-3.1 (m, 1H), 2.1-2.0 (s, 2H), 1.4-1.2 (m, 3H).

4. To a solution of Compound 4 (500 mg, 2.57 mmol) in DCM (10 mL) were added 8-aminoquinoline (370 mg, 2.57 mmol), EDCI (1 g, 5.14 mmol) and DMAP (80 mg). The reaction mixture was stirred at RT overnight. TLC indicated reaction completion. The residue was treated with water and extracted with DCM. The organic extracts were washed with brine, dried over anhydrous $Na_2SO_4$, filtered and concentrated to give a crude oil. The crude product was purified by silica gel chromatography to afford Example 16 (390 mg).

$^1$HNMR ($CDCl_3$, 300 MHz) δ: 1.4 (d, 3H), 2.8 (m, 2H), 3.4 (m, 1H), 3.8 (s, 3H), 6.8 (d, 2H), 7.3 (m, 2H), 7.5 (m, 3H), 8.1 (d, 1H), 8.7 (s, 2H).

LC-MS: m/z=321 (M+1)+.

5. To a solution of Example 16 (250 mg, 0.82 mmol) in THF (10 mL) were added LAH (155 mg, 4.1 mmol) portionwise at 0° C. The reaction mixture was stirred at refluxing for 2 hours. TLC indicated reaction completion. After cooling to 0° C., the residue was diluted with water and filtered and the filter cake washed with THF. The filtrate was concentrated and purified by silica gel chromatography to afford Example 15 (80 mg)

$^1$HNMR ($CDCl_3$, 300 MHz) δ: 1.3 (d, 3H), 2.1 (m, 2H), 2.9 (m, 1H), 3.2 (m, 2H), 3.8 (s, 3H), 6.1 (m, 1H), 6.5 (d, 1H), 6.9 (d, 2H), 7.0 (d, 1H), 7.2-7.4 (m, 4H), 8.1 (d, 1H), 8.7 (s, 1H).

LC-MS: m/z=307.2 (M+1)$^+$.

Synthesis of Examples 17 and 18

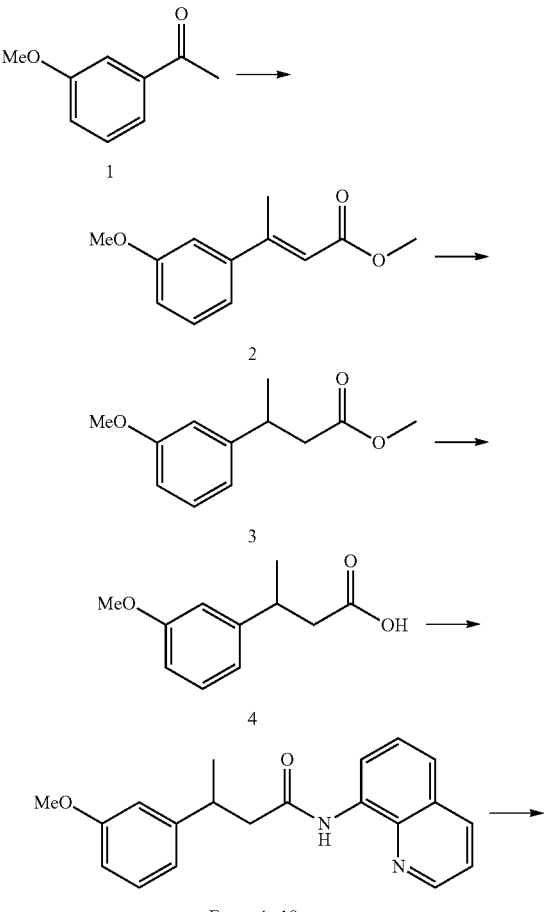

Example 18

39
-continued

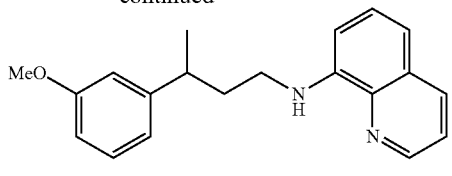

Example 17

Procedure:
1. To a solution of Trimethyl phosphonoacetate (7.3 g, 40 mmol) in dry THF (200 mL) was added NaH (1.6 g, 40 mmol, 60%) portionwise at 0° C. After the mixture was stirred at RT 2 hours, a solution of Compound 1 (5 g, 33.3 mmol) in dry THF (10 mL) was added dropwise. The resulting solution was stirred at RT for 1 hour and refluxed for 2 hours. TLC indicated reaction completion. The reaction mixture was diluted with saturated NH$_4$Cl solution and extracted with EA. The organic extracts were washed with water, brine, dried over anhydrous Na$_2$SO$_4$, filtered and concentrated to give a crude oil. The crude product was purified by silica gel chromatography (5% EA/PE~20% EA/PE) to afford Compound 2 (3 g, 44%).
2. To a solution of Compound 2 (3 g, 14.5 mmol) in THF (50 mL) was added Pd/C (300 mg). The reaction mixture was stirred under H$_2$ balloon at RT overnight. NMR indicated reaction completion. The residue was filtered and the filter cake washed with THF and the filtrate was concentrated to give Compound 3 (3 g, 99%).
3. To a solution of Compound 3 (3 g, 14.4 mmol) in THF/H$_2$O (50 mL, 1:1) was added LiOH.H$_2$O (1.8 g, 43.2 mmol). The reaction mixture was stirred at RT overnight. TLC indicated reaction completion. The solution was removed in vacuum, and the residue was adjusted to pH=3-4 with 6 N HCl solution at 0° C. and extracted with EA. The organic extracts were washed with brine, dried over anhydrous Na$_2$SO$_4$, filtered and concentrated to give Compound 4 (2.5 g, 89.3%).
4. To a solution of Compound 4 (400 mg, 2 mmol) in DCM (10 mL) were added 8-aminoquinoline (300 mg, 2 mmol), EDCI (760 mg, 4 mmol) and DMAP (80 mg). The reaction mixture was stirred at RT overnight. TLC indicated reaction completion. The residue was treated with water and extracted with DCM. The organic extracts were washed with brine, dried over anhydrous Na$_2$SO$_4$, filtered and concentrated to give a crude oil. The crude product was purified by silica gel chromatography to afford Example 18 (280 mg, 43.5%).
   $^1$HNMR (CDCl$_3$, 300 MHz) δ: 1.3-1.4 (d, 3H), 2.8-3.0 (m, 2H), 3.3-3.5 (m, 1H), 3.7-3.9 (d, 3H), 6.6-6.8 (m, 1H), 6.8-7.0 (m, 2H), 7.1-7.3 (m, 1H), 7.4-7.6 (m, 3H), 8.1-8.2 (d, 1H), 8.7-8.8 (d, 2H), 9.7-9.9 (s, 1H)
   LC-MS: m/z=343.2 (M+23)$^+$.
5. To a solution of Example 18 (180 mg, 0.6 mmol) in THF (20 mL) were added LAH (120 mg, 3 mmol) portionwise at 0° C. The reaction mixture was stirred at reflux for 2 hours. TLC indicated reaction completion. After cooling to 0° C., the residue was diluted with water and filtered and the filter cake washed with THF. The filtrate was concentrated and purified by silica gel chromatography to afford Example 17 (32 mg, 19.1%)
   $^1$HNMR (CDCl$_3$, 300 MHz) δ: 1.2-1.4 (d, 3H), 2.0-2.1 (t, 2H), 2.8-3.0 (t, 1H), 3.1-3.3 (m, 2H), 3.7-3.9 (d, 3H), 6.0-6.2 (d, 1H), 6.5-6.6 (d, 1H), 6.7-6.9 (m, 3H), 6.9-7.0 (d, 1H), 7.2-7.5 (m, 4H), 8.0-8.1 (t, 1H), 8.6-8.7 (d, 1H)
   LC-MS: m/z=307.2 (M+1)$^+$.

40
Synthesis of Examples 19 and 20

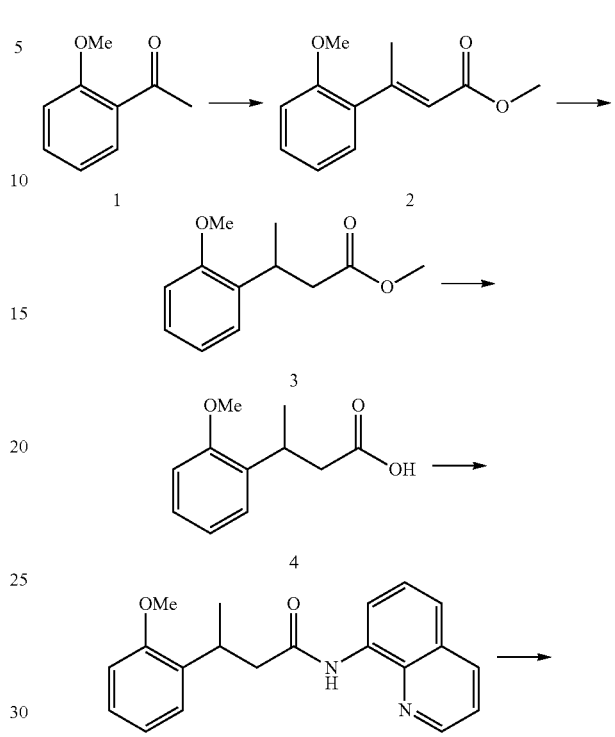

Example 20

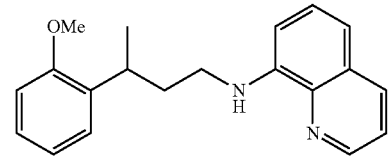

Example 19

Procedure:
1. To a solution of Trimethyl phosphonoacetate (14.6 g, 80 mmol) in dry THF (350 mL) was added NaH (3.2 g, 80 mmol, 60%) portionwise at 0° C. After the mixture was stirred at RT 2 hours, a solution of Compound 1 (10 g, 66.6 mmol) in dry THF (20 mL) was added dropwise. The resulting solution was stirred at RT for 1 hour and refluxed for 2 hours. TLC indicated reaction completion. The reaction mixture was diluted with saturated NH$_4$Cl solution and extracted with EA. The organic extracts were washed with water, brine, dried over anhydrous Na$_2$SO$_4$, filtered and concentrated to give a crude oil. The crude product was purified by silica gel chromatography (5% EA/PE~20% EA/PE) to afford Compound 2 (5.5 g).
   $^1$HNMR (CDCl$_3$, 300 MHz) δ: 2.5 (s, 3H), 3.7-3.9 (d, 6H), 5.9 (s, 1H), 6.9 (m, 2H), 7.1-(d, 1H), 7.3 (m, 1H)
2. To a solution of Compound 2 (5.5 g, 26.7 mmol) in THF (80 mL) was added Pd/C (500 mg). The reaction mixture was stirred under H$_2$ balloon at RT overnight. NMR indicated reaction completion. The residue was filtered and the filter cake washed with THF and the filtrate was concentrated to give Compound 3 (5.5 g).
   $^1$HNMR (CDCl$_3$, 300 MHz) δ: 1.2 (d, 3H), 2.4-2.7 (m, 2H), 3.6 (s, 3H), 3.9 (s, 3H), 6.9 (m, 2H), 7.1-7.3 (m, 2H).
3. To a solution of Compound 3 (5.5 g, 26.7 mmol) in THF/H$_2$O (100 mL, 1:1) was added LiOH.H$_2$O (3.36 g, 80 mmol). The reaction mixture was stirred at RT overnight. TLC indicated reaction completion. The solution was removed in vacuum, and the residue was adjusted to pH=3-4 with 6 N HCl solution at 0° C. Then it was extracted with EA. The organic extracts were washed with brine, dried over anhydrous Na$_2$SO$_4$, filtered and concentrated to give Compound 4 (4.7 g).

4. To a solution of Compound 4 (500 mg, 2.57 mmol) in DCM (10 mL) were added 8-aminoquinoline (370 mg, 2.57 mmol), EDCI (1 g, 5.14 mmol) and DMAP (80 mg). The reaction mixture was stirred at RT overnight. TLC indicated reaction completion. The residue was treated with water and extracted with DCM. The organic extracts were washed with brine, dried over anhydrous Na$_2$SO$_4$, filtered and concentrated to give a crude oil. The crude product was purified by silica gel chromatography to afford Example 20 (470 mg).
$^1$HNMR (CDCl$_3$, 300 MHz) δ: 1.4 (d, 3H), 2.6 (t, 1H), 3.0 (m, 1H), 3.9 (s, 3H), 6.9 (m, 2H), 7.2 (m, 2H), 7.5 (m, 3H), 8.1 (d, 2H), 8.8 (d, 2H), 9.8 (s, 1H).
LC-MS: m/z=321 (M+1)+.

5. To a solution of Example 20 (300 mg, 0.94 mmol) in THF (10 mL) were added LAH (180 mg, 4.7 mmol) portionwise at 0° C. The reaction mixture was stirred at refluxing for 2 hours. TLC indicated reaction completion. After cooling to 0° C., the residue was diluted with water and filtered and the filter cake washed with THF. The filtrate was concentrated and purified by silica gel chromatography to afford Example 19 (210 mg)
$^1$HNMR (CDCl$_3$, 300 MHz) δ: 1.4 (d, 3H), 2.0 (m, 2H), 3.2 (m, 2H), 3.5 (m, 1H), 3.9 (s, 3H), 6.2 (m, 1H), 6.6 (d, 1H), 6.9-7.1 (m, 3H), 7.1-7.5 (m, 4H), 8.0 (d, 1H), 8.7 (d, 1H).
LC-MS: m/z=307.2 (M+1)$^+$.

Synthesis of Examples 21 and 22

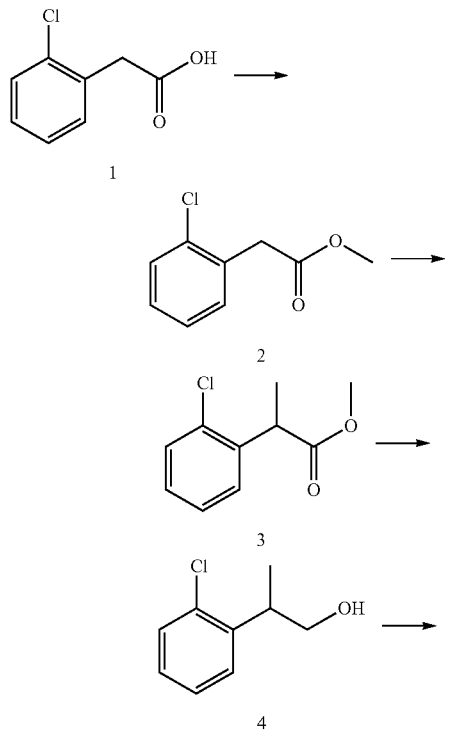

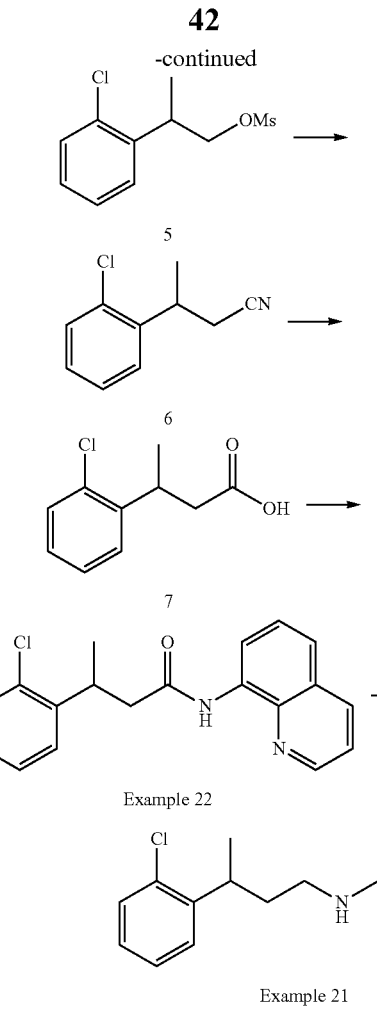

Example 22

Example 21

Procedure:
1. To a solution of Compound 1 (20 g, 117.6 mmol) in MeOH (100 mL) was added SOCl$_2$ (10 mL) dropwise at 0° C. The resulting solution was stirred at reflux overnight. TLC indicated reaction completion. The solvent was removed in vacuo, and the residue was treated with water and extracted with EA. The organic extracts were washed with saturated NaHCO$_3$ solution, brine, dried over anhydrous Na$_2$SO$_4$, filtered and concentrated to give Compound 2 (21 g, 97.2%).

2. To a solution of i-Pr$_2$NH (20 mL, 136.5 mmol) in dry THF (100 mL) was added n-BuLi (54.6 mL, 136.5 mmol) dropwise at −78° C. under N$_2$ and stirred for 30 min. Then a solution of Compound 2 (21 g, 113.7 mmol) in dry THF (100 mL) was added dropwise and stirred at this temp for 1 hour. CH$_3$I (24.2 g, 170.6 mmol) was added. The resulting solution was stirred at RT overnight. The residue was treated with water and extracted with EA. The organic extracts were washed with water, brine, dried over anhydrous Na$_2$SO$_4$, filtered and concentrated to give Compound 3 (21 g, 93%).

3. To a suspension mixture of LAH (4 g, 106 mmol) in dry THF (150 mL) was added a solution of Compound 3 (21 g, 106 mmol) in dry THF (50 mL) dropwise at 0° C. under N$_2$. The reaction mixture was heated to reflux for 2 hours. TLC indicated reaction completion. After cooling to 0° C., the residue was diluted with water and filtered and the filter cake washed with THF. The filtrate was concentrated and purified by silica gel chromatography to afford Compound 4 (15 g, 83.3 mmol).

43

4. To a solution of Compound 4 (5 g, 33.3 mmol) in DCM (50 mL) was added TEA (6.8 g, 66.6 mmol), then MsCl (4.6 g, 40 mmol) was added dropwise at 0° C. The reaction mixture was stirred at RT for 2 hours. TLC indicated reaction completion. The residue was treated with water and extracted with DCM. The organic extracts were washed with brine, dried over anhydrous $Na_2SO_4$, filtered and concentrated to give Compound 5 (7 g, 95%).
5. To a solution of Compound 5 (7 g, 28.2 mmol) in MeCN (30 mL) was added TMSCN (4.5 g, 45.3 mmol) at 0° C. and a solution of TBAF (11.5 g, 36.3 mmol) in dry THF (30 mL) was added dropwise. The reaction mixture was heated to 80° C. overnight. TLC indicated reaction completion. The solvent was removed in vacuo, and the residue was treated with water and extracted with EA. The organic extracts were washed with water, brine, dried over anhydrous $Na_2SO_4$, filtered and concentrated to give a crude oil. The crude product was purified by silica gel chromatography to afford Compound 6 (4 g, 80%).
6. To a solution of Compound 6 (4 g, 22.3 mmol) in EtOH (40 mL) was added 10% NaOH solution (40 mL). The reaction mixture was stirred at 90° C. overnight. TLC indicated reaction completion. The solvent was removed in vacuo, and the residue was treated with water and extracted with DCM. The organic extracts were washed with water, brine, dried over anhydrous $Na_2SO_4$, filtered and concentrated to give Compound 7 (3.5 g, 79.5%).
7. To a solution of Compound 7 (500 mg, 2.5 mmol) in DCM (10 mL) were added 8-aminoquinoline (300 mg, 2 mmol), EDCI (760 mg, 4 mmol) and DMAP (80 mg). The reaction mixture was stirred at RT overnight. TLC indicated reaction completion. The residue was treated with water and extracted with DCM. The organic extracts were washed with brine, dried over anhydrous $Na_2SO_4$, filtered and concentrated to give a crude oil. The crude product was purified by silica gel chromatography to afford Example 22 (150 mg, 22.8%).
$^1$HNMR (CDCl$_3$, 300 MHz) δ: 1.3-1.4 (d, 3H), 2.6-2.7 (m, 1H), 2.9-3.0 (m, 1H), 3.9-4.1 (m, 1H), 7.1-7.2 (m, 1H), 7.2-7.6 (m, 6H), 8.1-8.2 (d, 1H), 8.7-8.9 (m, 2H), 9.8-9.9 (s, 1H)
LC-MS: m/z=325.2 (M+1)$^+$.
8. To a solution of Example 22 (100 mg, 0.3 mmol) in THF (20 mL) were added LAH (60 mg, 1.5 mmol) portionwise at 0° C. The reaction mixture was stirred at reflux for 2 hours. TLC indicated reaction completion. After cooling to 0° C., the residue was diluted with water and filtered and the filter cake washed with THF. The filtrate was concentrated and purified by silica gel chromatography to afford Example 21 (30 mg, 16.5%)
$^1$HNMR (CDCl$_3$, 300 MHz) δ: 1.2-1.3 (d, 3H), 2.0-2.2 (m, 2H), 3.1-3.3 (m, 2H), 3.4-3.5 (m, 1H), 6.1-6.2 (m, 1H), 6.5-6.6 (m, 1H), 6.9-7.1 (m, 2H), 7.2-7.4 (m, 4H), 8.0-8.1 (m, 1H), 8.6-8.7 (m, 1H).
LC-MS: m/z=311.2 (M+1.

Synthesis of Examples 23 and 24

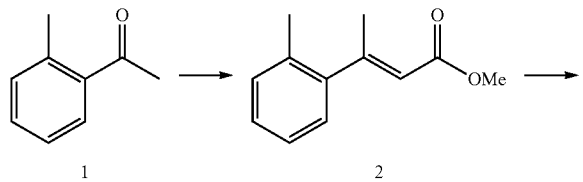

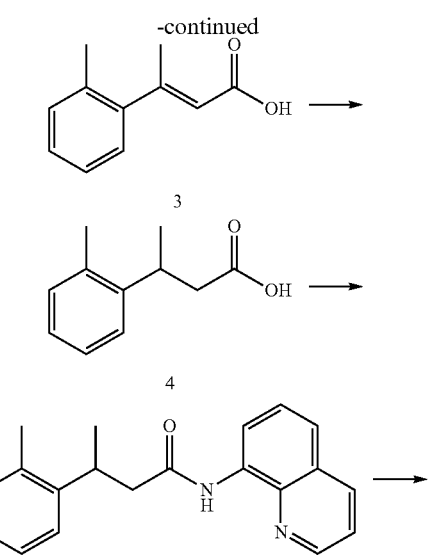

Example 24

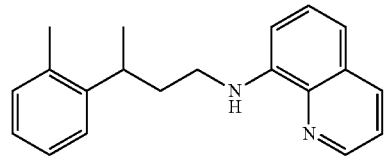

Example 23

Procedure:
1. To a solution of Trimethyl phosphonoacetate (7.0 g, 40 mmol) in dry THF (200 mL) was added NaH (1.6 g, 40 mmol, 60%) portionwise at 0° C. After 2 hours stirring at RT, a solution of Compound 1 (5 g, 33.3 mmol) in dry THF (10 mL) was added dropwise at this temp. The resulting solution was stirred at RT for 1 hour and reflux for 2 hours. TLC indicated reaction completion. The reaction mixture was diluted with saturated NH$_4$Cl solution and extracted with EA. The organic extracts were washed with water, brine, dried over anhydrous $Na_2SO_4$, filtered and concentrated to give a crude oil. The crude product was purified by silica gel chromatography (5% EA/PE~20% EA/PE) to afford Compound 2 (3 g, 44%).
2. To a solution of Compound 2 (2.8 g, 14.5 mmol) in THF (50 mL) was added Pd/C (300 mg). The reaction mixture was stirred under a H$_2$ balloon, RT overnight. NMR indicated reaction completion. The residue was filtered and the filter cake washed with THF and the filtrate was concentrated to give Compound 3 (3 g, 99%).
3. To a solution of Compound 3 (2.8 g, 14.4 mmol) in THF/H$_2$O (50 mL, 1:1) was added LiOH.H$_2$O (1.8 g, 43.2 mmol). The reaction mixture was stirred at RT overnight. TLC indicated reaction completion. The solution was remove in vacuo, and the residue was adjusted to pH=3-4 with 6 N HCl solution at 0° C. and extracted with EA. The organic extracts were washed with brine, dried over anhydrous $Na_2SO_4$, filtered and concentrated to give Compound 4 (2.5 g, 89.3%).
4. To a solution of Compound 4 (380 mg, 2 mmol) in DCM (10 mL) were added 8-aminoquinoline (300 mg, 2 mmol), EDCI (760 mg, 4 mmol) and DMAP (80 mg). The reaction mixture was stirred at RT overnight. TLC indicated reaction completion. The residue was treated with water and extracted with DCM. The organic extracts were washed with brine, dried over anhydrous Na₂SO₄, filtered and concentrated to give a crude oil. The crude product was purified by silica gel chromatography to afford Example 24 (250 mg, 45.5%).

¹HNMR (CDCl₃, 300 MHz) δ: 1.3-1.5 (d, 3H), 2.4 (s, 2H), 2.7-2.8 (m, 1H), 2.8-2.9 (m, 1H), 3.7-3.8 (m, 1H), 7.0-7.3 (m, 5H), 7.4-7.5 (m, 3H), 8.1-8.2 (dm, 1H), 8.7-8.8 (s, 2H), 9.7-9.8 (s, 1H).

LC-MS: m/z=327.2 (M+23)⁺.

5. To a solution of Example 24 (180 mg, 0.6 mmol) in THF (20 mL) were added LAH (120 mg, 3 mmol) portionwise at 0° C. The reaction mixture was stirred at reflux for 2 hours. TLC indicated reaction completion. After cooling to 0° C., the residue was diluted with water and filtered and the filter cake washed with THF. The filtrate was concentrated and purified by silica gel chromatography to afford Example 23 (25 mg, 21.1%)

¹HNMR (CDCl₃, 300 MHz) δ: 1.3-1.5 (d, 3H), 2.1-2.2 (d, 2H), 2.3-2.4 (s, 3H), 3.2-3.3 (m, 3H), 6.1-6.2 (m, 1H), 6.5-6.6 (d, 1H), 7.0-7.1 (d, 1H), 7.1-7.3 (m, 3H), 7.4-7.5 (m, 3H), 8.0-8.1 (d, 1H), 8.7-8.8 (s, 1H)

LC-MS: m/z=291.3 (M+1)⁺.

Synthesis of Examples 25, 26 and 27

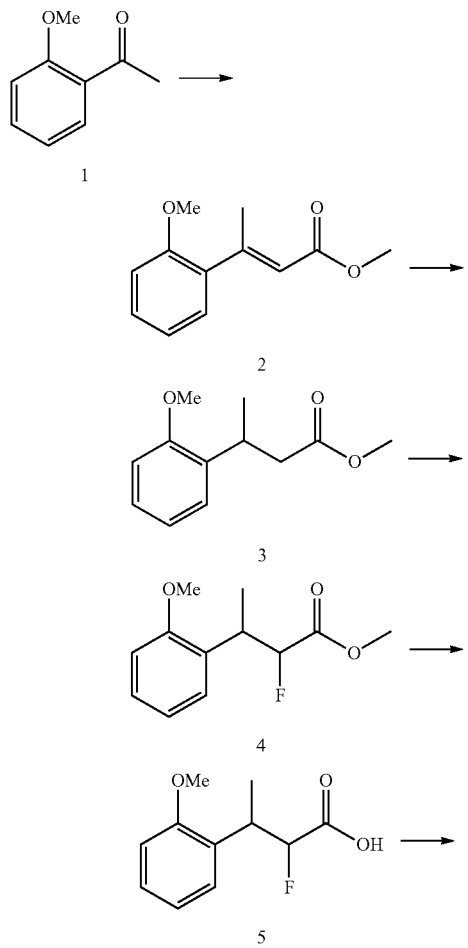

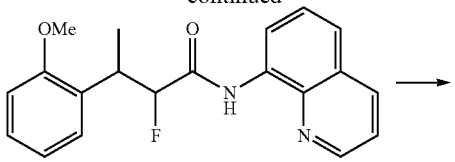

Example 26

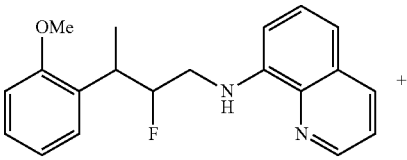

Example 25

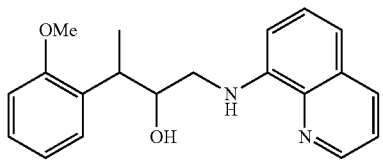

Example 27

Procedure:

1. To a solution of Trimethyl phosphonoacetate (14.6 g, 80 mmol) in dry THF (350 mL) was added NaH (3.2 g, 80 mmol, 60%) portionwise at 0° C. After 2 hours stirring at RT, a solution of Compound 1 (10 g, 66.6 mmol) in dry THF (20 mL) was added dropwise at this temp. The resulting solution was stirred at RT for 1 hour and reflux for 2 hours. TLC indicated reaction completion. The reaction mixture was diluted with saturated NH₄Cl solution and extracted with EA. The organic extracts were washed with water, brine, dried over anhydrous Na₂SO₄, filtered and concentrated to give a crude oil. The crude product was purified by silica gel chromatography (5% EA/PE~20% EA/PE) to afford Compound 2 (5.5 g).

¹HNMR (CDCl₃, 300 MHz) δ: 2.5 (s, 3H), 3.7-3.9 (d, 6H), 5.9 (s, 1H), 6.9 (m, 2H), 7.1-(d, 1H), 7.3 (m, 1H).

2. To a solution of Compound 2 (5.5 g, 26.7 mmol) in THF (80 mL) was added Pd/C (500 mg). The reaction mixture was stirred under a H₂ balloon, RT overnight. NMR indicated reaction completion. The residue was filtered and the filter cake washed with THF and the filtrate was concentrated to give Compound 3 (5.5 g).

¹HNMR (CDCl₃, 300 MHz) δ: 1.2 (d, 3H), 2.4-2.7 (m, 2H), 3.6 (s, 4H), 3.9 (s, 3H), 6.9 (m, 2H), 7.1-7.3 (m, 2H).

3. To a solution of i-Pr₂NH (1.2 mL, 9.6 mmol) in dry THF (10 mL) was added n-BuLi (3.8 mL, 9.6 mmol) dropwise at −78° C. under N₂ and stirred for 30 min. Then a solution of Compound 3 (1 g, 4.8 mmol) in dry THF (5 mL) was added dropwise and stirred at this temp. The reaction mixture was allowed to slowly warmed to −5° C. Then re-cooled to −78° C., a solution of NFSI (3.8 g, 12 mmol) in dry THF (10 mL) was added dropwise. The resulting solution was stirred at RT overnight. The residue was treated with water and extracted with EA. The organic extracts were washed with saturated water, brine, dried over anhydrous Na₂SO₄, filtered and concentrated to give 1.2 g crude. The crude product was purified by silica gel chromatography to afford Compound 4 (500 mg, 46.3%).

¹HNMR (CDCl₃, 300 MHz) δ: 1.2-1.3 (d, 3H), 3.6-3.7 (m, 1H), 3.8 (s, 3H), 3.9 (s, 3H), 5.0-5.3 (d, 1H), 6.8-7.0 (m, 2H), 7.1-7.3 (m, 2H).

4. To a solution of Compound 4 (500 mg, 2.2 mmol) in THF/MeOH/H₂O (10 mL, 1:1:2) was added LiOH.H₂O (280 mg, 6.6 mmol). The reaction mixture was stirred at RT overnight. TLC indicated reaction completion. The solution was remove in vacuo, and the residue was adjusted to pH=3-4 with 6 N HCl solution at 0° C. and extracted with EA. The organic extracts were washed with brine, dried over anhydrous Na₂SO₄, filtered and concentrated to give Compound 5 (400 mg, 85.3%).

¹HNMR (CDCl₃, 300 MHz) δ: 1.2-1.3 (d, 3H), 3.8-3.9 (s, 3H), 3.9-4.0 (m 1H), 5.1-5.3 (d, 1H), 6.8-7.0 (m, 2H), 7.1-7.3 (m, 2H).

5. To a solution of Compound 5 (500 mg, 2.57 mmol) in DCM (10 mL) were added 8-aminoquinoline (370 mg, 2.57 mmol), EDCI (1 g, 5.14 mmol) and DMAP (80 mg). The reaction mixture was stirred at RT overnight. TLC indicated reaction completion. The residue was treated with water and extracted with DCM. The organic extracts were washed with brine, dried over anhydrous Na₂SO₄, filtered and concentrated to give a crude oil. The crude product was purified by silica gel chromatography to afford Example 26 (130 mg, 16.3%).

¹HNMR (CDCl₃, 300 MHz) δ: 1.2-1.3 (d, 3H), 3.8-3.9 (s, 3H), 4.0-4.3 (m, 1H), 5.2-5.4 (d, 1H), 6.8-7.0 (m, 2H), 7.2-7.3 (m, 1H), 7.4-7.6 (m, 4H), 8.1-8.2 (d, 1H). 8.8-8.9 (d, 2H).

LC-MS: m/z=361.2 (M+1)+.

6. To a solution of Example 26 (100 mg, 0.3 mmol) in THF (10 mL) were added LAH (56 mg, 1.5 mmol) portionwise at 0° C. The reaction mixture was stirred at RT for 6 hours. After cooling to 0° C., the residue was diluted with water and filtered and the filter cake washed with THF. The filtrate was concentrated and purified by silica gel chromatography to afford Example 25 (8 mg, 8.4%) and Example 27 (3 mg, 8.2%).

Example 25

¹HNMR (CDCl₃, 300 MHz) δ: 1.2-1.4 (m, 3H), 3.3-3.6 (m, 2H), 3.8-3.9 (m, 3H), 4.8-5.1 (m, 1H), 6.4-6.5 (m, 1H), 6.8-7.1 (m, 3H), 7.2-7.5 (m, 5H), 8.0-8.1 (m, 1H), 8.7-8.8 (m, 1H).

LC-MS: m/z=325.2 (M+1)+

Example 27

LC-MS: m/z=323.3 (M+1)

Synthesis of Examples 28 and 29

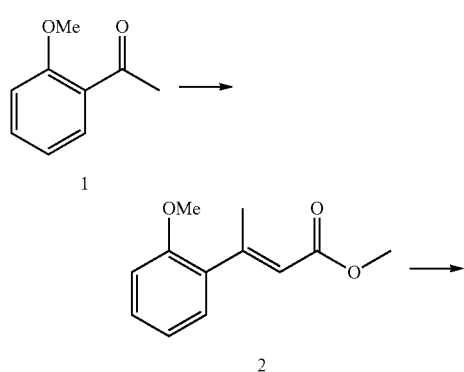

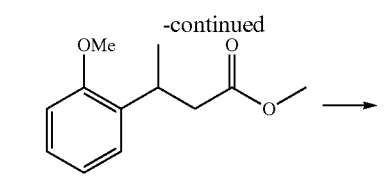

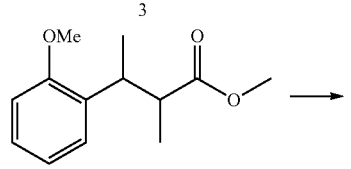

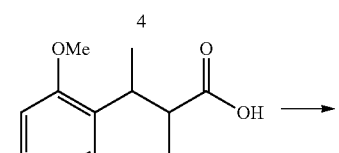

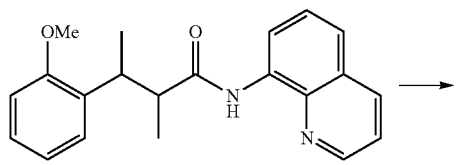

Example 29

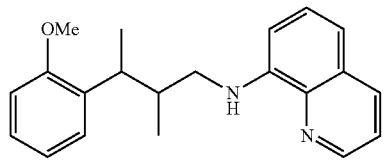

Example 28

Procedure:

1. To a solution of Trimethyl phosphonoacetate (14.6 g, 80 mmol) in dry THF (350 mL) was added NaH (3.2 g, 80 mmol, 60%) portionwise at 0° C. After 2 hours stirring at RT, a solution of Compound 1 (10 g, 66.6 mmol) in dry THF (20 mL) was added dropwise at this temp. The resulting solution was stirred at RT for 1 hour and reflux for 2 hours. TLC indicated reaction completion. The reaction mixture was diluted with saturated NH₄Cl solution and extracted with EA. The organic extracts were washed with water, brine, dried over anhydrous Na₂SO₄, filtered and concentrated to give a crude oil. The crude product was purified by silica gel chromatography (5% EA/PE~20% EA/PE) to afford Compound 2 (5.5 g).

¹HNMR (CDCl₃, 300 MHz) δ: 2.5 (s, 3H), 3.7-3.9 (d, 6H), 5.9 (s, 1H), 6.9 (m, 2H), 7.1-(d, 1H), 7.3 (m, 1H).

2. To a solution of Compound 2 (5.5 g, 26.7 mmol) in THF (80 mL) was added Pd/C (500 mg). The reaction mixture was stirred under a H₂ balloon, RT overnight. NMR indicated reaction completion. The residue was filtered and the filter cake washed with THF and the filtrate was concentrated to give Compound 3 (5.5 g).

¹HNMR (CDCl₃, 300 MHz) δ: 1.2 (d, 3H), 2.4-2.7 (m, 2H), 3.6 (s, 4H), 3.9 (s, 3H), 6.9 (m, 2H), 7.1-7.3 (m, 2H).

3. To a solution of i-Pr₂NH (2.7 mL, 19.2 mmol) in dry THF (20 mL) was added n-BuLi (7.7 mL, 19.2 mmol) dropwise at −78° C. under N₂ and stirred for 30 min. Then a solution of Compound 3 (2 g, 9.6 mmol) in dry THF (10 mL) was added dropwise and stirred at this temp. The reaction mixture was allowed to slowly warmed to −5° C. Then re-cooled to −78° C., a solution of CH$_3$I (3.4 g, 24 mmol) in dry THF (10 mL) was added dropwise. The resulting solution was stirred at RT overnight. The residue was treated with water and extracted with EA. The organic extracts were washed with water, brine, dried over anhydrous Na$_2$SO$_4$, filtered and concentrated to give 2 g crude oil. The crude product was purified by silica gel chromatography to afford Compound 4 (700 mg, 33.3%).

$^1$HNMR (CDCl$_3$, 300 MHz) δ: 0.9-1.0 (d, 3H), 1.2-1.3 (d, 3H), 2.7-2.8 (m, 1H), 3.3-3.4 (m, 1H), 3.7 (s, 3H), 3.9 (s, 3H), 6.8-7.0 (m, 2H), 7.1-7.3 (m, 2H).

4. To a solution of Compound 4 (700 mg, 3.2 mmol) in THF/MeOH/H$_2$O (25 mL, 2:1:2) was added LiOH.H$_2$O (660 mg, 15.6 mmol). The reaction mixture was stirred at RT overnight. TLC indicated reaction completion. The solution was remove in vacuo, and the residue was adjusted to pH=3-4 with 6 N HCl solution at 0° C. and extracted with EA. The organic extracts were washed with brine, dried over anhydrous Na$_2$SO$_4$, filtered and concentrated to give Compound 5 (600 mg, 92%).

$^1$HNMR (CDCl$_3$, 300 MHz) δ: 0.9-1.0 (d, 3H), 1.2-1.3 (d, 3H), 2.7-2.8 (m, 1H), 3.3-3.4 (m, 1H), 3.8 (s, 3H), 6.8-7.0 (m, 2H), 7.1-7.3 (m, 2H).

5. To a solution of Compound 5 (500 mg, 2.57 mmol) in DCM (10 mL) were added 8-aminoquinoline (370 mg, 2.57 mmol), EDCI (1 g, 5.14 mmol) and DMAP (80 mg). The reaction mixture was stirred at RT overnight. TLC indicated reaction completion. The residue was treated with water and extracted with DCM. The organic extracts were washed with brine, dried over anhydrous Na$_2$SO$_4$, filtered and concentrated to give a crude oil. The crude product was purified by silica gel chromatography to afford Example 29 (120 mg, 15%).

$^1$HNMR (CDCl$_3$, 300 MHz) δ: 1.1-1.2 (d, 3H), 1.3-1.4 (d, 3H), 2.9-3.1 (m, 1H), 3.5-3.7 (m, 1H), 3.9-4.1 (ss, 3H), 6.8-7.0 (m, 2H), 7.1-7.3 (m, 3H), 7.4-7.6 (m, 3H), 8.1-8.2 (m, 1H), 8.7-8.9 (m, 2H). 9.8-10.0 (ss, 1H).

LC-MS: m/z=357.2 (M+23)+.

6. To a solution of Example 29 (80 mg, 0.24 mmol) in THF (10 mL) were added LAH (45 mg, 1.2 mmol) portionwise at 0° C. The reaction mixture was stirred at 60° C. for 2 hours. After cooling to 0° C., the residue was diluted with water and filtered and the filter cake washed with THF. The filtrate was concentrated and purified by silica gel chromatography to afford Example 28 (13 mg, 17%).

$^1$HNMR (CDCl$_3$, 300 MHz) δ: 0.9-1.0 (d, 3H), 1.2-1.4 (d, 3H), 2.2-2.3 (m, 1H), 3.0-3.2 (m, 1H), 3.2-3.5 (m, 2H), 6.5-6.6 (m, 1H), 6.8-7.0 (m, 2H), 7.1-7.4 (m, 4H), 8.0-8.1 (m, 1H), 8.7-8.8 (m, 1H).

LC-MS: m/z=321.3 (M+1)+.

Synthesis of Examples 30 and 31

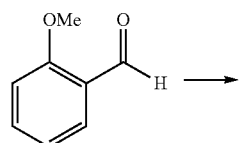

1

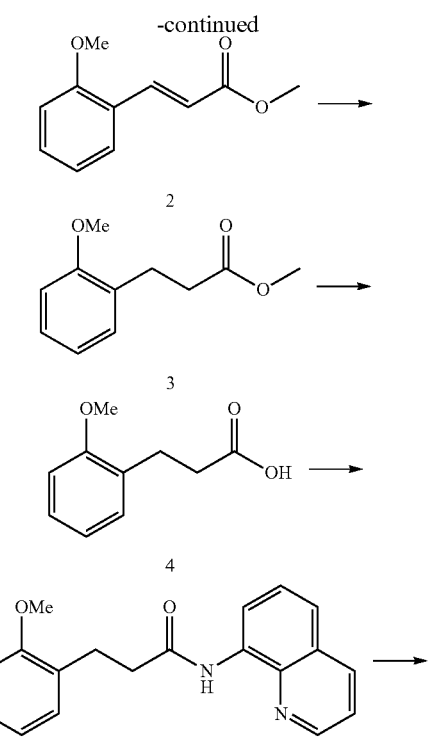

Example 31

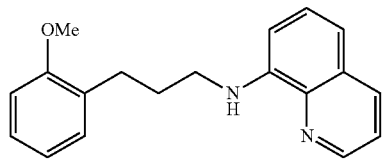

Example 30

Procedure:

1. To a solution of Trimethyl phosphonoacetate (8 g, 44 mmol) in dry THF (200 mL) was added NaH (1.75 g, 44 mmol, 60%) portionwise at 0° C. After 2 hours stirring at RT, a solution of Compound 1 (5 g, 36.6 mmol) in dry THF (10 mL) was added dropwise at this temp. The resulting solution was stirred at RT for 1 hour and reflux for 2 hours. TLC indicated reaction completion. The reaction mixture was diluted with saturated NH$_4$Cl solution and extracted with EA. The organic extracts were washed with water, brine, dried over anhydrous Na$_2$SO$_4$, filtered and concentrated to give a crude oil. The crude product was purified by silica gel chromatography (5% EA/PE~10% EA/PE) to afford Compound 2 (4 g, 53%).

2. To a solution of Compound 2 (4 g, 14.5 mmol) in THF (50 mL) was added Pd/C (300 mg). The reaction mixture was stirred under a H$_2$ balloon, RT overnight. NMR indicated reaction completion. The residue was filtered and the filter cake washed with THF and the filtrate was concentrated to give Compound 3 (3 g, 85.7%).

3. To a solution of Compound 3 (3 g, 15.4 mmol) in THF/H$_2$O (50 mL, 1:1) was added LiOH.H$_2$O (3.2 g, 77.3 mmol). The reaction mixture was stirred at RT overnight. TLC indicated reaction completion. The solution was remove in vacuo, and the residue was adjusted to pH=3-4 with 6 N HCl solution at 0° C. and extracted with EA. The organic extracts were washed with brine, anhydrous Na$_2$SO$_4$, filtered and concentrated to give Compound 4 (1 g, 36%).

4. To a solution of Compound 4 (1 g, 5.55 mmol) in DCM (10 mL) were added 8-aminoquinoline (400 mg, 2.78 mmol), EDCI (2.19 g, 11.1 mmol) and DMAP (135 mg). The reaction mixture was stirred at RT overnight. TLC indicated reaction completion. The residue was treated with water and extracted with DCM. The organic extracts were washed with brine, dried over anhydrous Na$_2$SO$_4$, filtered and concentrated to give a crude oil. The crude product was purified by silica gel chromatography to afford Example 31 (400 mg, 25.6%).

$^1$HNMR (CDCl$_3$, 300 MHz) δ: 2.7-2.9 (d, 2H), 3.1-3.3 (d, 2H), 3.8-4.0 (s, 3H), 6.8-7.0 (d, 2H), 7.2-7.4 (s, 3H), 7.5-7.7 (s, 3H), 8.1-8.3 (m, 1H), 8.8-9.0 (d, 2H), 9.7-9.9 (m, 1H)

LC-MS: m/z=306.1 (M+1)$^+$.

5. To a solution of Example 31 (200 mg, 0.65 mmol) in THF (20 mL) were added LAH (124 mg, 3.5 mmol) portionwise at 0° C. The reaction mixture was stirred at reflux for 2 hours. TLC indicated reaction completion. After cooling to 0° C., the residue was diluted with water and filtered and the filter cake washed with THF. The filtrate was concentrated and purified by silica gel chromatography to afford Example 30 (100 mg, 52.6%)

$^1$HNMR (CDCl$_3$, 300 MHz) δ: 2.0-2.2 (d, 2H), 2.8-3.0 (d, 2H), 3.1-3.3 (d, 2H), 4.8-5.0 (s, 3H), 6.2-6.4 (d, 4H), 6.6-6.7 (m, 1H), 6.8-7.0 (d, 2H), 7.0-7.2 (m, 1H), 7.2-7.5 (s, 6H), 8.0-8.2 (m, 1H), 8.7-8.9 (m, 1H)

LC-MS: m/z=292.16 (M+1)+.

Synthesis of Examples 32 and 33

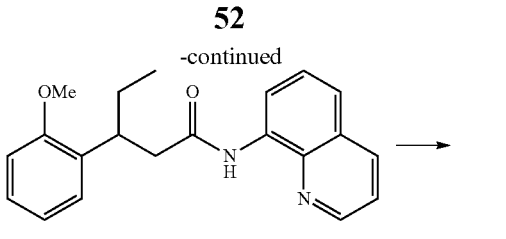

Example 33

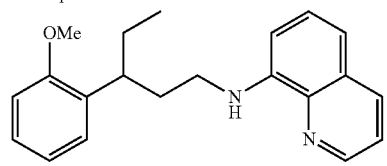

Example 32

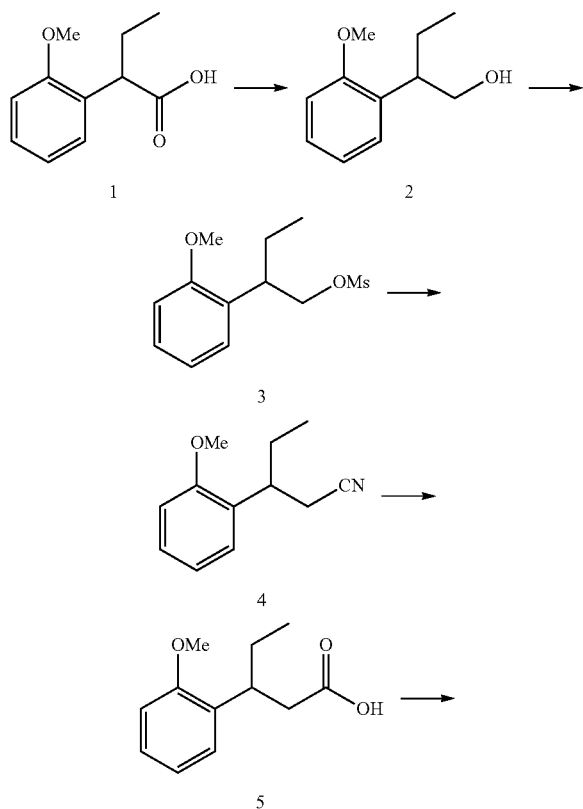

Procedure:

1. To a solution of i-Pr$_2$NH (15.2 g, 150 mmol) in dry THF (100 mL) was added n-BuLi (60 mL, 150 mmol) dropwise at −78° C. under N$_2$ and stirred for 30 min. Then a solution of 2-methoxyphenylacetic acid (10 g, 60.2 mmol) in dry THF (100 mL) was added dropwise and stirred at this temp for 1 hour. Bromoethane (9.8 g, 90.3 mmol) was added. The resulting solution was stirred at RT overnight. The residue was treated with water and extracted with EA. The organic extracts were washed with water, brine, dried over anhydrous Na$_2$SO$_4$, filtered and concentrated to give Compound 1 (10 g, 86.2%).

$^1$HNMR (CDCl$_3$, 300 MHz) δ: 0.9-1.0 (t, 3H), 1.7-1.9 (m, 1H), 2.0-2.2 (m, 1H), 3.8-3.9 (s, 1H), 3.9-4.0 (m, 1H), 6.8-7.0 (m, 2H), 7.2-7.4 (m, 2H).

2. To a mixture of LAH (4.3 g, 113 mmol) in THF (100 mL) were added a solution of Compound 1 (11 g, 56.7 mmol) in THF (50 mL) dropwise at 0° C. under N$_2$. The reaction mixture was stirred at RT for 4 hours. TLC indicated reaction completion. After cooling to 0° C., the residue was diluted with water and filtered and the filter cake washed with THF. The filtrate was concentrated to afford Compound 2 (8 g, 87%).

$^1$HNMR (CDCl$_3$, 300 MHz) δ: 0.8-0.9 (t, 3H), 1.6-1.9 (m, 2H), 3.2-3.3 (m, 1H), 3.7-3.8 (m, 2H), 3.8-3.9 (s, 3H), 6.8-7.0 (m, 2H), 7.1-7.3 (m, 2H).

3. To a solution of Compound 2 (4 g, 22.2 mmol) in DCM (50 mL) was added TEA (4.6 mL, 33.3 mmol), then MsCl (3 g, 26.7 mmol) was added dropwise at 0° C. The reaction mixture was stirred at RT for 3 hours. TLC indicated reaction completion. The residue was treated with water and extracted with DCM. The organic extracts were washed with brine, dried over anhydrous Na$_2$SO$_4$, filtered and concentrated to give Compound 3 (5.2 g, 91.2%).

$^1$HNMR (CDCl$_3$, 300 MHz) δ: 0.8-0.9 (t, 3H), 1.6-1.9 (m, 2H), 2.7-2.8 (s, 3H), 3.3-3.4 (m, 1H), 3.8-3.9 (s, 3H), 4.3-4.5 (m, 2H), 6.8-7.0 (m, 2H), 7.1-7.3 (m, 2H).

4. To a solution of Compound 3 (5.2 g, 20 mmol) in MeCN (30 mL) was added TMSCN (4 g, 40 mmol) at 0° C., and a solution of TBAF (7.9 g, 30 mmol) in dry THF (30 mL) was added dropwise. The reaction mixture was heated to 80° C. overnight. TLC indicated reaction completion. The solvent was removed in vacuo, and the residue was treated with water and extracted with EA. The organic extracts were washed with water, brine, dried over anhydrous Na$_2$SO$_4$, filtered and concentrated to give a crude oil. The crude product was purified by silica gel chromatography to afford Compound 4 (2.2 g, 58%).

¹HNMR (CDCl₃, 300 MHz) δ: 0.8-0.9 (t, 3H), 1.7-2.0 (m, 2H), 2.5-2.6 (m, 2H), 3.2-3.3 (m, 1H), 3.8-3.9 (s, 3H), 6.8-7.0 (m, 2H), 7.1-7.3 (m, 2H).

5. To a solution of Compound 4 (2.2 g, 11.6 mmol) in EtOH (25 mL) was added 10% NaOH solution (25 mL). The reaction mixture was stirred at 90° C. overnight. TLC indicated reaction completion. The solvent was removed in vacuo, and the residue was treated with water and adjusted PH=1 with 3 N HCl solution and extracted with EA. The organic extracts were washed with water, brine, dried over anhydrous Na₂SO₄, filtered and concentrated to give Compound 5 (2 g, 83.3%).

¹HNMR (CDCl₃, 300 MHz) δ: 0.8-0.9 (t, 3H), 1.6-1.8 (m, 2H), 2.5-2.7 (m, 2H), 3.3-3.5 (m, 1H), 3.8-3.9 (d, 3H), 6.8-7.0 (m, 2H), 7.1-7.3 (m, 2H).

6. To a solution of Compound 5 (500 mg, 2.4 mmol) in DCM (10 mL) were added 8-aminoquinoline (350 mg, 2.4 mmol), EDCI (700 mg, 3.6 mmol) and DMAP (150 mg). The reaction mixture was stirred at RT overnight. TLC indicated reaction completion. The residue was treated with water and extracted with DCM. The organic extracts were washed with brine, dried over anhydrous Na₂SO₄, filtered and concentrated to give a crude oil. The crude product was purified by silica gel chromatography to afford Example 33 (200 mg, 25%).

¹HNMR (CDCl₃, 300 MHz) δ: 0.8-0.9 (t, 3H), 1.7-1.9 (m, 2H), 2.7-3.0 (m, 2H), 3.5-3.7 (m, 1H), 3.8-3.9 (s, 3H), 6.8-7.0 (m, 2H), 7.1-7.3 (m, 2H), 7.4-7.6 (m, 3H), 8.1-8.2 (d, 1H), 8.7-8.8 (m, 2H).

LC-MS: m/z=357.2 (M+23)+.

7. To a solution of Example 33 (150 mg, 0.45 mmol) in THF (10 mL) were added LAH (85 mg, 2.2 mmol) portionwise at 0° C. The reaction mixture was stirred at reflux for 2 hours. TLC indicated reaction completion. After cooling to 0° C., the residue was diluted with water and filtered and the filter cake washed with THF. The filtrate was concentrated and purified by silica gel chromatography to afford Example 32 (40 mg, 28%).

¹HNMR (CDCl₃, 300 MHz) δ: 0.7-0.9 (t, 3H), 1.7-1.7 (m, 2H), 1.9-2.1 (m, 2H), 3.1-3.3 (m, 3H), 3.8-3.9 (s, 3H), 6.1-6.2 (m, 1H), 6.5-6.6 (d, 1H), 6.8-7.0 (m, 3H), 7.1-7.2 (m, 2H), 7.3-7.4 (m, 2H), 8.0-8.1 (d, 1H), 8.6-8.7 (m, 1H).

LC-MS: m/z=321.2 (M+1)+.

Synthesis of Examples 34 and 35

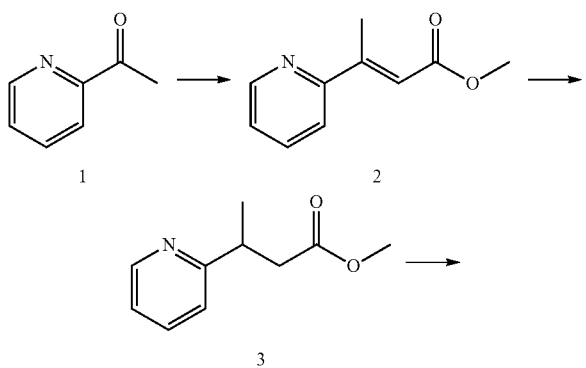

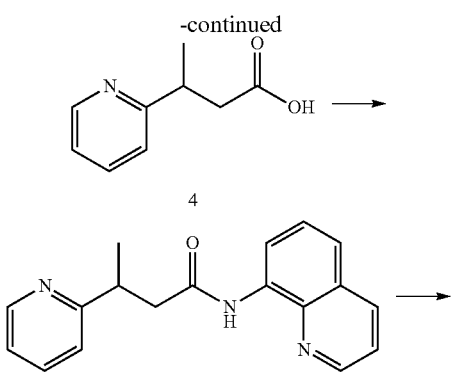

Example 35

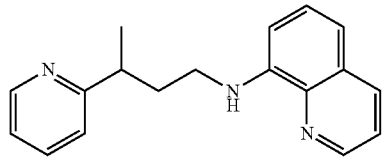

Example 34

Procedure:

6. To a solution of Trimethyl phosphonoacetate (10.2 g, 56 mmol) in dry THF (200 mL) was added NaH (2.24 g, 56 mmol, 60%) portionwise at 0° C. After 2 hours stirring at RT, a solution of Compound 1 (5 g, 46 mmol) in dry THF (10 mL) was added dropwise at this temp. The resulting solution was stirred at RT for 1 hour and reflux for 2 hours. TLC indicated reaction completion. The reaction mixture was diluted with saturated NH₄Cl solution and extracted with EA. The organic extracts were washed with water, brine, dried over anhydrous Na₂SO₄, filtered and concentrated to give a crude oil. The crude product was purified by silica gel chromatography (5% EA/PE~20% EA/PE) to afford Compound 2 (3.5 g).

7. To a solution of Compound 2 (3.5 g, 21.4 mmol) in THF (50 mL) was added Pd/C (300 mg). The reaction mixture was stirred under a H₂ balloon, RT overnight. NMR indicated reaction completion. The residue was filtered and the filter cake washed with THF and the filtrate was concentrated to give Compound 3 (3.2 g).

8. To a solution of Compound 3 (2.7 g, 15 mmol) in THF/H₂O (50 mL, 1:1) was added LiOH.H₂O (1.9 g, 45 mmol). The reaction mixture was stirred at RT overnight. TLC indicated reaction completion. The solution was remove in vacuo, and the residue was adjusted to pH=6 with 6 N HCl solution at 0° C. and extracted with EA. The organic extracts were washed with brine, dried over anhydrous Na₂SO₄, filtered and concentrated to give 2.4 g of Compound 4.

9. To a solution of Compound 4 (400 mg, 2.4 mmol) in DCM (10 mL) were added 8-aminoquinoline (360 mg, 2.4 mmol), EDCI (910 mg, 4.8 mmol) and DMAP (100 mg). The reaction mixture was stirred at RT overnight. TLC indicated reaction completion. The residue was treated with water and extracted with DCM. The organic extracts were washed with brine, dried over anhydrous Na₂SO₄, filtered and concentrated to give a crude oil. The crude product was purified by silica gel chromatography to afford Example 35 (280 mg, 35.5%).

¹HNMR (CDCl₃, 300 MHz) δ: 1.4 (d, 3H), 2.8 (m, 1H), 3.2 (m, 1H), 3.6 (m, 1H), 6.7-6.9 (m, 3H), 7.1-7.2 (m, 1H), 7.4 (m, 3H), 7.5-7.6 (m, 1H), 8.1 (m, 1H), 8.6 (d, 1H), 8.7 (m, 2H), 9.9 (s, 1H)

LC-MS: m/z=292 (M+1)⁺.

10. To a solution of Example 35 (200 mg, 0.68 mmol) in THF (20 mL) were added LAH (120 mg, 3 mmol) portionwise at 0° C. The reaction mixture was stirred at reflux for 2 hours. TLC indicated reaction completion. After cooling to 0° C., the residue was diluted with water and filtered and the filter cake washed with THF. The filtrate was concentrated and purified by silica gel chromatography to afford Example 34 (65 mg, 34.2%)

$^1$HNMR (CDCl$_3$, 300 MHz) δ: 1.2-1.3 (d, 3H), 2.1-2.3 (m, 3H), 3.1-3.2 (m, 3H), 6.1 (m, 1H), 6.5 (m, 1H), 6.9 (m, 1H), 7.1 (m, 2H), 7.3 (m, 2H), 7.6 (d, 1H), 8.0 (m, 1H), 8.5-8.7 (d, 2H)

LC-MS: m/z=278.2 (M+1)+.

Synthesis of Examples 36 and 37

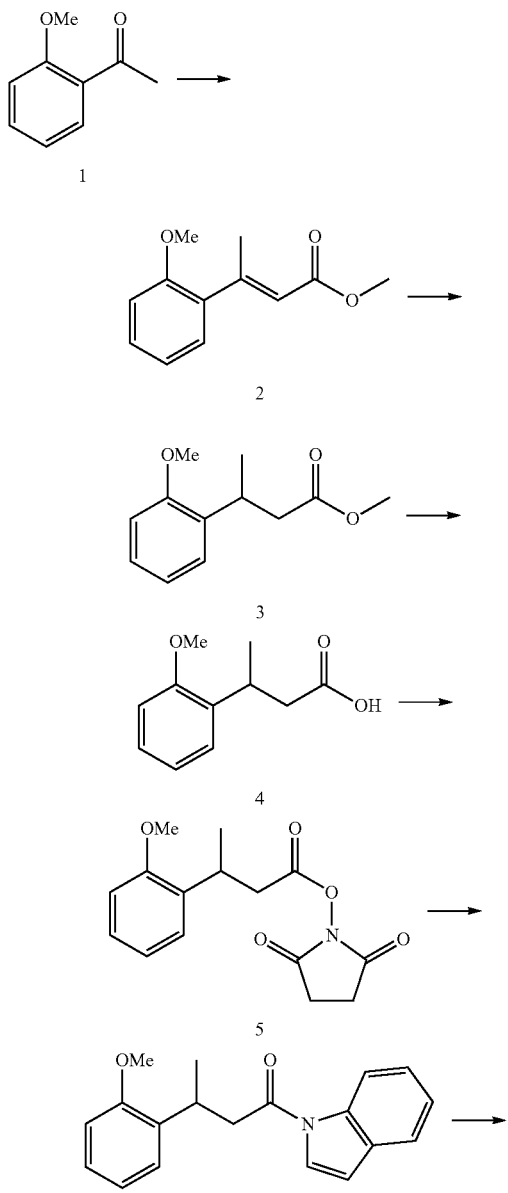

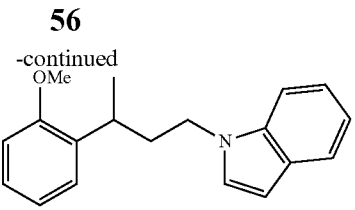

Example 36

Procedure:
1. To a solution of Trimethyl phosphonoacetate (7.3 g, 40 mmol) in dry THF (200 mL) was added NaH (1.6 g, 40 mmol, 60%) portionwise at 0° C. After 2 hours stirring at RT, a solution of Compound 1 (5 g, 33.3 mmol) in dry THF (10 mL) was added dropwise at this temp. The resulting solution was stirred at RT for 1 hour and reflux for 2 hours. TLC indicated reaction completion. The reaction mixture was diluted with saturated NH$_4$Cl solution and extracted with EA. The organic extracts were washed with water, brine, dried over anhydrous Na$_2$SO$_4$, filtered and concentrated to give a crude oil. The crude product was purified by silica gel chromatography (5% EA/PE~20% EA/PE) to afford Compound 2 (3 g, 44%).
2. To a solution of Compound 2 (3 g, 14.5 mmol) in THF (50 mL) was added Pd/C (300 mg). The reaction mixture was stirred under H$_2$ balloon, RT overnight. NMR indicated reaction completion. The residue was filtered and the filter cake washed with THF and the filtrate was concentrated to give Compound 3 (3 g, 99%).
3. To a solution of Compound 3 (3 g, 14.4 mmol) in THF/H$_2$O (50 mL, 1:1) was added LiOH.H$_2$O (1.8 g, 43.2 mmol). The reaction mixture was stirred at RT overnight. TLC indicated reaction completion. The solution was remove in vacuo, and the residue was adjusted to pH=3-4 with 6 N HCl solution at 0° C. and extracted with EA. The organic extracts were washed with brine, dried over anhydrous Na$_2$SO$_4$, filtered and concentrated to give Compound 4 (2.5 g, 89.3%).
4. To a solution of Compound 4 (3 g, 15.5 mmol), 1-hydroxypyrrolidine-2,5-dione (1.8 g, 15.5 mmol) in 1,4-dioxane (30 mL) and ethyl acetate (30 mL) were added, DCC (3.2 g, 15.5 mmol). The reaction mixture was stirred at RT overnight. TLC indicated reaction completion. Filtered and concentrated to give a crude oil. The crude product was purified by silica gel chromatography to afford Compound 5 (250 mg, 45.5%).

$^1$HNMR (CDCl$_3$, 300 MHz) δ: 1.3-1.5 (d, 3H), 2.6-2.8 (d, 2H), 3.3-3.5 (m, 1H), 3.7-3.8 (d, 3H), 6.7-6.9 (m, 3H), 7.1-7.2 (m, 1H), 7.5-7.6 (m, 1H), 7.6-7.7 (m, 1H), 7.7-7.8 (m, 1H), 7.9-8.1 (d, 1H), 8.4-8.5 (d, 1H), 8.6-8.7 (d, 1H)

5. To a solution of 1H-indole (0.67 g, 5.7 mmol) in DMF (10 mL) were added NaH (0.33 g, 8.5 mmol) at ice bath. The reaction mixture was stirred at ice bath for 2 hours. Then Compound 5 (2.5 g, 8.5 mmol) in DMF (10 mL) were added it at ice bath. TLC indicated reaction completion. The residue was treated with water and extracted with EA. The organic extracts were washed with brine, dried over anhydrous Na$_2$SO$_4$, filtered and concentrated to give a crude oil. The crude product was purified by silica gel chromatography to afford Example 37 (750 mg, 45.5%).

$^1$HNMR (CDCl$_3$, 300 MHz) δ: 1.4 (d, 3H), 2.9-3.0 (m, 1H), 3.3-3.4 (d, 1H), 3.8-3.9 (s, 4H), 6.6-6.7 (s, 1H), 6.8-7.0 (m, 2H), 7.2-7.4 (m, 5H), 7.6 (d, 2H), 8.5-8.6 (d, 1H).

LC-MS: m/z=316.2 (M+23)+.

6. To a solution of Example 37 (100 mg, 0.34 mmol) in THF (20 mL) were added Borane-methyl sulfide complex (0.17 ml, 10M, 1.7 mmol) portionwise at 0° C. The reaction mixture was stirred at 50° C. for 2 hours. TLC indicated reaction completion. After cooling to 0° C., the residue was diluted with saturated NH₄Cl solution and extracted with EA. The organic extracts were washed with water, brine, dried over anhydrous Na₂SO₄, filtered and concentrated to give a crude oil, purified by silica gel chromatography to afford Example 36 (25 mg, 21.1%)

¹HNMR (CDCl₃, 300 MHz) δ: 1.4 (d, 3H), 2.0-2.2 (m, 2H), 3.2-3.3 (d, 1H), 3.7-3.8 (s, 3H), 4.0 (d, 2H), 6.4-6.5 (s, 1H), 6.8-6.9 (m, 1H), 6.9-7.2 (m, 3H), 7.2-7.3 (m, 4H), 7.6 (d, 1H).

LC-MS: m/z=280.2 (M+1)+.

Synthesis of Example 38

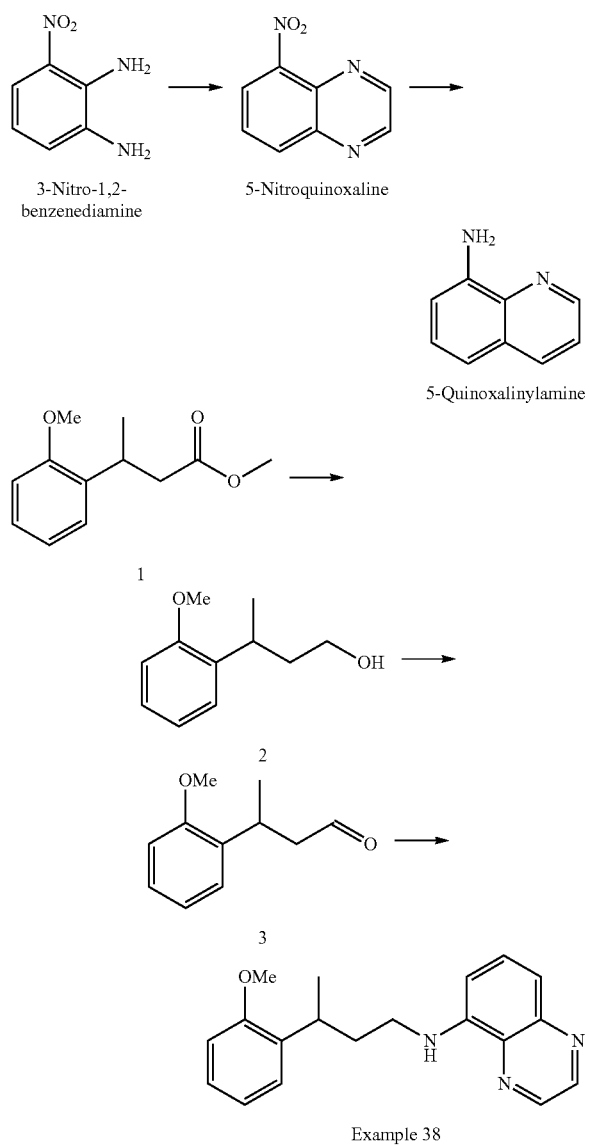

Example 38

Procedure:

Synthesis of 5-quinoxalinylamine

To a solution of 3-nitro-1,2-benzenediamine (2 g, 13 mmol) in EtOH (30 mL) was added glyoxal (4.4 mL, 40% in water, 39 mmol). The reaction mixture was heated to reflux for 2 hours before stirring at RT for overnight. The solvent was removed in vacuo, the residue was treated with water and extracted with DCM. The organic extracts were concentrated and purified by recrystallization to afford 5-nitroquinoxaline (2.2 g, 97%).

¹HNMR (CDCl₃, 300 MHz) δ: 7.8-7.9 (t, 1H), 8.2-8.3 (d, 2H), 8.4-8.5 (d, 1H), 9.0-0.1 (d, 2H).

To a solution of 5-nitroquinoxaline (500 mg, 3 mmol) in THF/EtOH (10 mL, 1:1) was added NiCl*6H₂O (675 mg, 3 mmol) and NaBH₄ (114 mg, 3 mmol) portionwise at 0° C. The resulting solution was stirred at RT for 1 hour. The residue was filtered and the filter cake washed with EtOH and the filtrated with concentrated to give a crude oil. The crude product was purified by silica gel chromatography to afford 5-quinoxalinylamine (150 mg, 36%).

¹HNMR (CDCl₃, 300 MHz) δ: 6.9-7.0 (d, 1H), 7.4-7.5 (d, 1H), 7.5-7.6 (t, 1H), 8.6-8.7 (s, 1H), 8.8-8.9 (s, 1H).

1. To a solution of Compound 3, prepared as described for Compound 3 in Examples 36 and 37, (800 mg, 3.8 mmol) in THF (20 mL) were added LAH (150 mg, 3.8 mmol) portionwise at 0° C. The reaction mixture was stirred at RT for 2 hours. TLC indicated reaction completion. After cooling to 0° C., the residue was diluted with water and filtered and the filter cake washed with THF. The filtrate was concentrated to afford Compound 2 (650 mg, 94%).

2. To a solution of Oxalyl chloride (530 mg, 4.2 mmol) in DCM (10 mL) was added dry DMSO (650 mg, 8.3 mmol) dropwise at −78° C. under N₂ protection. After 10 min stirring, a solution of Compound 2 (500 mg, 2.8 mmol) in DCM (5 mL) was added dropwise. Then stirred at this temp for 30 min. TEA (1.2 mL, 8.3 mmol) was added dropwise. The resulting solution was allowed to slowly warm to RT. The residue was treated with water and extracted with DCM. The organic extracts were concentrated and purified by silica gel chromatography to afford Compound 3 (240 mg, 48.5%).

¹HNMR (CDCl₃, 300 MHz) δ: 1.2-1.3 (d, 2H), 2.5-2.8 (m, 2H), 3.7-3.8 (m, 1H), 3.8-3.9 (s, 1H), 6.8-7.0 (m, 2H), 7.1-7.3 (m, 2H), 9.7-9.8 (s, 1H).

3. To a solution of Compound 3 (62 mg, 0.34 mmol) in MeOH (1 mL) were added 5-quinoxalinylamine (50 mg, 0.34 mmol), NaCNBH₃ (22 mg, 0.34 mmol) and AcOH (41 mg, 0.69 mmol). The resulting solution was stirred at RT overnight. The residue was purified by silica gel chromatography to afford Example 38 (20 mg, 23.2%).

¹HNMR (CDCl₃, 300 MHz) δ: 1.3-1.4 (d, 3H), 2.0-2.2 (m, 2H), 3.2-3.4 (m, 2H), 3.4-3.5 (m, 1H), 3.8-3.9 (m, 4H), 6.1-6.2 (m, 1H), 6.6-6.7 (m, 1H), 6.8-7.0 (m, 2H), 7.1-7.3 (m, 2H), 7.5-7.6 (m, 1H). 8.6-8.7 (s, 1H), 8.8-8.9 (s, 1H).

LC-MS: m/z=308.2 (M+1)+.

Synthesis of Example 39

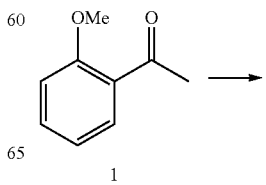

1

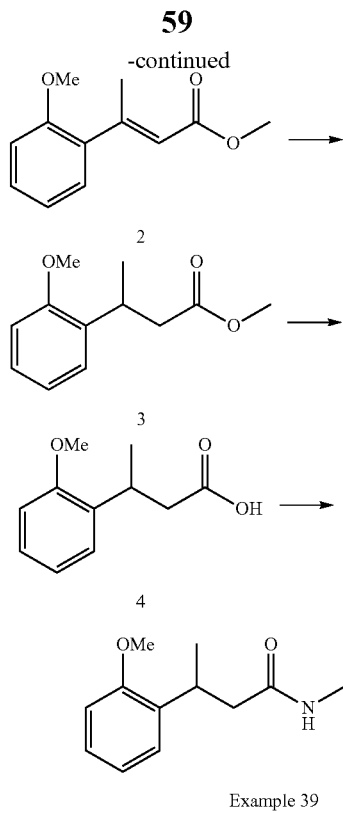

Example 39

Procedure:
1. To a solution of Trimethyl phosphonoacetate (14.6 g, 80 mmol) in dry THF (350 mL) was added NaH (3.2 g, 80 mmol, 60%) portionwise at 0° C. After 2 hours stirring at RT, a solution of Compound 1 (10 g, 66.6 mmol) in dry THF (20 mL) was added dropwise at this temp. The resulting solution was stirred at RT for 1 hour and reflux for 2 hours. TLC indicated reaction completion. The reaction mixture was diluted with saturated NH$_4$Cl solution and extracted with EA. The organic extracts were washed with water, brine, dried over anhydrous Na$_2$SO$_4$, filtered and concentrated to give a crude oil. The crude product was purified by silica gel chromatography (5% EA/PE~20% EA/PE) to afford Compound 2 (5.5 g).
$^1$HNMR (CDCl$_3$, 300 MHz) δ: 2.5 (s, 3H), 3.7-3.9 (d, 6H), 5.9 (s, 1H), 6.9 (m, 2H), 7.1-(d, 1H), 7.3 (m, 1H).
2. To a solution of Compound 2 (5.5 g, 26.7 mmol) in THF (80 mL) was added Pd/C (500 mg). The reaction mixture was stirred under a H$_2$ balloon, RT overnight. NMR indicated reaction completion. The residue was filtered and the filter cake washed with THF and the filtrate was concentrated to give Compound 3 (5.5 g).
$^1$HNMR (CDCl$_3$, 300 MHz) δ: 1.2 (d, 3H), 2.4-2.7 (m, 2H), 3.6 (s, 4H), 3.9 (s, 3H), 6.9 (m, 2H), 7.1-7.3 (m, 2H).
3. To a solution of Compound 3 (5.5 g, 26.7 mmol) in THF/H$_2$O (100 mL, 1:1) was added LiOH.H$_2$O (3.36 g, 80 mmol). The reaction mixture was stirred at RT overnight. TLC indicated reaction completion. The solution was remove in vacuo, and the residue was adjusted to pH=3-4 with 6 N HCl solution at 0° C. and extracted with EA. The organic extracts were washed with brine, dried over anhydrous Na$_2$SO$_4$, filtered and concentrated to give Compound 4 (4.7 g).
$^1$HNMR (CDCl$_3$, 300 MHz) δ: 1.2-1.3 (d, 3H), 2.4-2.8 (m, 2H), 3.5-3.7 (m 1H), 3.8-3.9 (s, 3H), 6.8-7.0 (m, 2H), 7.1-7.3 (m, 2H).

4. To a solution of Compound 4 (100 mg, 0.51 mmol) in DCM (5 mL) were added 5-quinoxalinylamine, prepared as described in Example 38, (75 mg, 0.51 mmol), EDCI (197 mg, 1.03 mmol) and DMAP (20 mg). The reaction mixture was stirred at RT overnight. TLC indicated reaction completion. The residue was treated with water and extracted with DCM. The organic extracts were washed with brine, dried over anhydrous Na$_2$SO$_4$, filtered and concentrated to give a crude oil. The crude product was purified by silica gel chromatography to afford Example 39 (15 mg, 9.1%).
$^1$HNMR (CDCl$_3$, 300 MHz) δ: 1.3-1.4 (d, 3H), 2.6-3.0 (m, 2H), 3.7-3.9 (m, 4H), 6.8-7.0 (m, 2H), 7.1-7.3 (m, 2H), 7.7-7.8 (s, 2H), 8.7-8.8 (s, 1H). 8.8-8.9 (d, 1H), 8.9-9.0 (s, 1H).
LC-MS: m/z=322.2 (M+1)+.

Synthesis of Examples 40 and 41

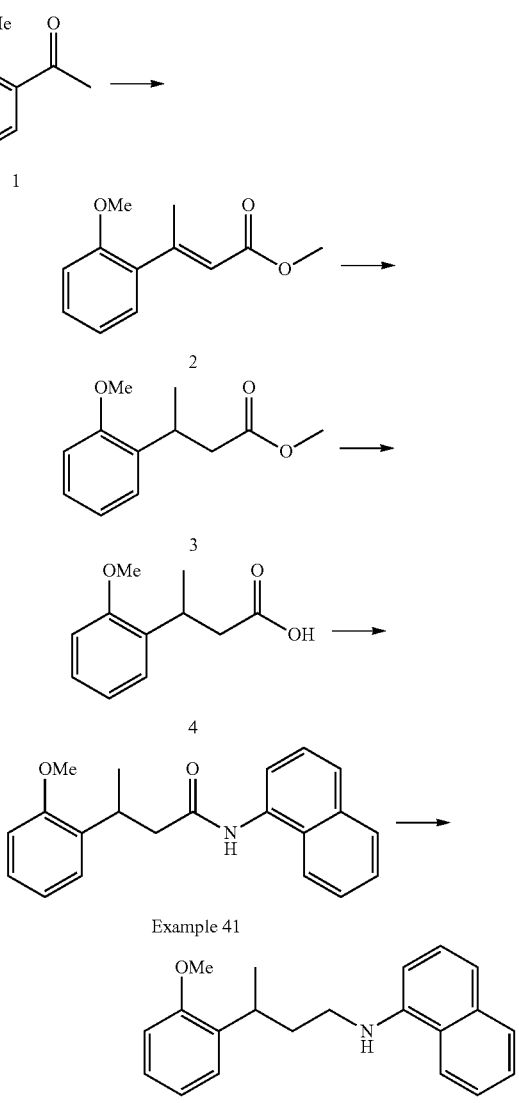

Example 41

Example 40

Procedure:
1. To a solution of Trimethyl phosphonoacetate (14.6 g, 80 mmol) in dry THF (350 mL) was added NaH (3.2 g, 80 mmol, 60%) portionwise at 0° C. After 2 hours stirring at RT, a solution of Compound 1 (10 g, 66.6 mmol) in dry THF (20 mL) was added dropwise at this temp. The resulting solution was stirred at RT for 1 hour and reflux for 2 hours. TLC indicated reaction completion. The reaction mixture was diluted with saturated NH₄Cl solution and extracted with EA. The organic extracts were washed with water, brine, dried over anhydrous Na₂SO₄, filtered and concentrated to give a crude oil. The crude product was purified by silica gel chromatography (5% EA/PE~20% EA/PE) to afford Compound 2 (5.5 g).

¹HNMR (CDCl₃, 300 MHz) δ: 2.5 (s, 3H), 3.7-3.9 (d, 6H), 5.9 (s, 1H), 6.9 (m, 2H), 7.1-(d, 1H), 7.3 (m, 1H).

2. To a solution of Compound 2 (5.5 g, 26.7 mmol) in THF (80 mL) was added Pd/C (500 mg). The reaction mixture was stirred under a H₂ balloon, RT overnight. NMR indicated reaction completion. The residue was filtered and the filter cake washed with THF and the filtrate was concentrated to give Compound 3 (5.5 g).

¹HNMR (CDCl₃, 300 MHz) δ: 1.2 (d, 3H), 2.4-2.7 (m, 2H), 3.6 (s, 4H), 3.9 (s, 3H), 6.9 (m, 2H), 7.1-7.3 (m, 2H).

3. To a solution of Compound 3 (5.5 g, 26.7 mmol) in THF/H₂O (100 mL, 1:1) was added LiOH.H₂O (3.36 g, 80 mmol). The reaction mixture was stirred at RT overnight. TLC indicated reaction completion. The solution was remove in vacuo, and the residue was adjusted to pH=3-4 with 6 N HCl solution at 0° C. and extracted with EA. The organic extracts were washed with brine, dried over anhydrous Na₂SO₄, filtered and concentrated to give Compound 4 (4.7 g).

¹HNMR (CDCl₃, 300 MHz) δ: 1.2-1.3 (d, 3H), 2.4-2.8 (m, 2H), 3.5-3.7 (m 1H), 3.8-3.9 (s, 3H), 6.8-7.0 (m, 2H), 7.1-7.3 (m, 2H).

4. To a solution of Compound 4 (500 mg, 2.57 mmol) in DCM (10 mL) were added 1-naphthylamine (370 mg, 2.57 mmol), EDCI (1 g, 5.14 mmol) and DMAP (80 mg). The reaction mixture was stirred at RT overnight. TLC indicated reaction completion. The residue was treated with water and extracted with DCM. The organic extracts were washed with brine, dried over anhydrous Na₂SO₄, filtered and concentrated to give a crude oil. The crude product was purified by silica gel chromatography to afford Example 41 (350 mg, 42.5%).

¹HNMR (CDCl₃, 300 MHz) δ: 1.3-1.4 (d, 3H), 2.6-3.0 (m, 2H), 3.7-3.9 (m, 4H), 6.8-7.0 (m, 2H), 7.2-7.4 (m, 2H), 7.4-7.6 (m, 4H), 7.6-7.8 (m, 1H). 7.8-7.9 (d, 2H).

LC-MS: m/z=320.3 (M+1)+.

5. To a solution of Example 41 (300 mg, 0.94 mmol) in THF (10 mL) were added LAH (178 mg, 4.7 mmol) portionwise at 0° C. The reaction mixture was stirred at reflux for 2 hours. TLC indicated reaction completion. After cooling to 0° C., the residue was diluted with water and filtered and the filter cake washed with THF. The filtrate was concentrated and purified by silica gel chromatography to afford Example 40 (50 mg, 17.5%)

¹HNMR (CDCl₃, 300 MHz) δ: 1.2-1.3 (d, 3H), 1.9-2.1 (m, 2H), 3.1-3.3 (m, 2H), 3.5 (m, 1H), 3.8-3.9 (s, 3H), 4.4-4.5 (m, 1H), 6.5-6.6 (d, 1H), 6.8-7.0 (m, 2H), 7.1-7.3 (m, 4H), 7.3-7.5 (m, 2H), 7.6-7.8 (m, 1H).

LC-MS: m/z=306.2 (M+1)+.

Synthesis of Examples 42 and 43

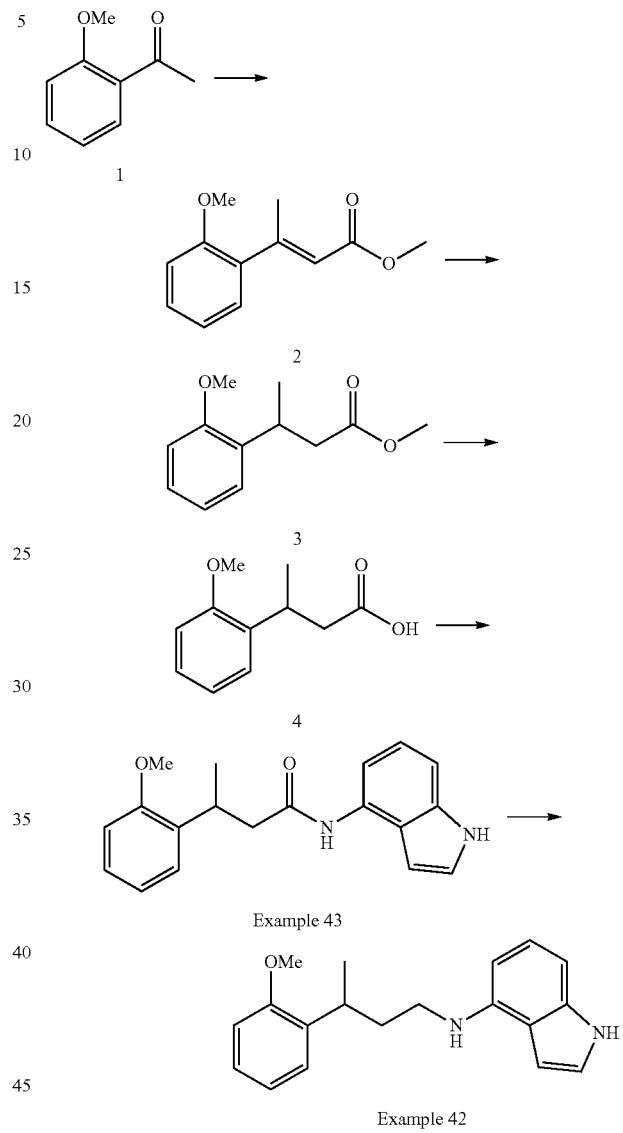

Example 43

Example 42

Procedure:

1. To a solution of Trimethyl phosphonoacetate (14.6 g, 80 mmol) in dry THF (350 mL) was added NaH (3.2 g, 80 mmol, 60%) portionwise at 0° C. After 2 hours stirring at RT, a solution of Compound 1 (10 g, 66.6 mmol) in dry THF (20 mL) was added dropwise at this temp. The resulting solution was stirred at RT for 1 hour and reflux for 2 hours. TLC indicated reaction completion. The reaction mixture was diluted with saturated NH₄Cl solution and extracted with EA. The organic extracts were washed with water, brine, dried over anhydrous Na₂SO₄, filtered and concentrated to give a crude oil. The crude product was purified by silica gel chromatography (5% EA/PE~20% EA/PE) to afford Compound 2 (5.5 g).

¹HNMR (CDCl₃, 300 MHz) δ: 2.5 (s, 3H), 3.7-3.9 (d, 6H), 5.9 (s, 1H), 6.9 (m, 2H), 7.1-(d, 1H), 7.3 (m, 1H).

2. To a solution of Compound 2 (5.5 g, 26.7 mmol) in THF (80 mL) was added Pd/C (500 mg). The reaction mixture was stirred under a H₂ balloon, RT overnight. NMR indicated reaction completion. The residue was filtered and the filter cake washed with THF and the filtrate was concentrated to give Compound 3 (5.5 g).

¹HNMR (CDCl₃, 300 MHz) δ: 1.2 (d, 3H), 2.4-2.7 (m, 2H), 3.6 (s, 4H), 3.9 (s, 3H), 6.9 (m, 2H), 7.1-7.3 (m, 2H).

3. To a solution of Compound 3 (5.5 g, 26.7 mmol) in THF/H₂O (100 mL, 1:1) was added LiOH.H₂O (3.36 g, 80 mmol). The reaction mixture was stirred at RT overnight. TLC indicated reaction completion. The solution was remove in vacuo, and the residue was adjusted to pH=3-4 with 6 N HCl solution at 0° C. and extracted with EA. The organic extracts were washed with brine, dried over anhydrous Na₂SO₄, filtered and concentrated to give Compound 4 (4.7 g).

¹HNMR (CDCl₃, 300 MHz) δ: 1.2-1.3 (d, 3H), 2.4-2.8 (m, 2H), 3.5-3.7 (m 1H), 3.8-3.9 (s, 3H), 6.8-7.0 (m, 2H), 7.1-7.3 (m, 2H).

4. To a solution of Compound 4 (500 mg, 2.57 mmol) in DCM (10 mL) were added 4-aminoindole (340 mg, 2.57 mmol), EDCI (1 g, 5.14 mmol) and DMAP (80 mg). The reaction mixture was stirred at RT overnight. TLC indicated reaction completion. The residue was treated with water and extracted with DCM. The organic extracts were washed with brine, dried over anhydrous Na₂SO₄, filtered and concentrated to give a crude oil. The crude product was purified by silica gel chromatography to afford Example 43 (200 mg, 25.2%).

¹HNMR (CDCl₃, 300 MHz) δ: 1.3-1.4 (d, 3H), 2.6-3.0 (m, 2H), 3.7-3.9 (m, 4H), 6.8-7.0 (m, 2H), 7.2-7.5 (m, 5H), 7.6-7.8 (m, 1H). 8.2-8.3 (m, 1H).

LC-MS: m/z=309.3 (M+1)⁺.

5. To a solution of Example 43 (150 mg, 0.48 mmol) in THF (10 mL) were added LAH (93 mg, 2.4 mmol) portionwise at 0° C. The reaction mixture was stirred at reflux for 2 hours. TLC indicated reaction completion. After cooling to 0° C., the residue was diluted with water and filtered and the filter cake washed with THF. The filtrate was concentrated and purified by silica gel chromatography to afford Example 42 (50 mg, 35%)

¹HNMR (CDCl₃, 300 MHz) δ: 1.2-1.3 (d, 3H), 1.9-2.1 (m, 2H), 3.1-3.3 (m, 2H), 3.4-3.5 (m, 1H), 3.8-3.9 (s, 3H), 6.2-6.3 (t, 1H), 6.3-6.4 (d, 1H), 6.6-7.1 (m, 4H), 7.1-7.3 (m, 2H), 8.0-8.1 (m, 1H).

LC-MS: m/z=295.2 (M+1)+.

Synthesis of Examples 44 and 45

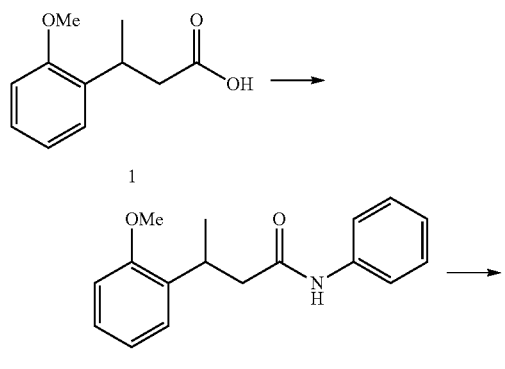

Example 45

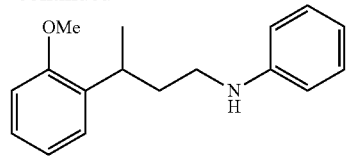

Example 44

Procedure:

1. To a solution of Compound 1, prepared as described for Compound 4 in Examples 42 and 43, (500 mg, 2.57 mmol) in DCM (10 mL) were added aniline (240 mg, 2.57 mmol), EDCI (1 g, 5.14 mmol) and DMAP (80 mg). The reaction mixture was stirred at RT overnight. TLC indicated reaction completion. The residue was treated with water and extracted with DCM. The organic extracts were washed with brine, dried over anhydrous Na₂SO₄, filtered and concentrated to give a crude oil. The crude product was purified by silica gel chromatography to afford Example 45 (300 mg, 43.3%).

¹HNMR (CDCl₃, 300 MHz) δ: 1.3-1.4 (d, 3H), 2.5-2.8 (m, 2H), 3.6-3.8 (m, 1H), 3.8-3.9 (s, 3H), 6.8-7.0 (m, 2H), 7.0-7.2 (m, 2H), 7.2-7.4 (m, 4H), 7.4-7.5 (m, 2H).

LC-MS: m/z=270.2 (M+1)+.

2. To a solution of Example 45 (200 mg, 0.74 mmol) in THF (10 mL) were added LAH (141 mg, 3.7 mmol) portionwise at 0° C. The reaction mixture was stirred at reflux for 2 hours. TLC indicated reaction completion. After cooling to 0° C., the residue was diluted with water and filtered and the filter cake washed with THF. The filtrate was concentrated and purified by silica gel chromatography to afford Example 44 (80 mg, 42.1%).

¹HNMR (CDCl₃, 300 MHz) δ: 1.2-1.3 (d, 3H), 1.8-2.0 (m, 2H), 2.9-3.1 (m, 2H), 3.3-3.4 (m, 1H), 3.8-3.9 (s, 3H), 6.5-6.6 (d, 1H), 6.6-6.7 (t, 1H), 6.8-7.0 (m, 2H), 7.1-7.3 (m, 4H).

LC-MS: m/z=256.2 (M+1)+.

Synthesis of Examples 46 and 47

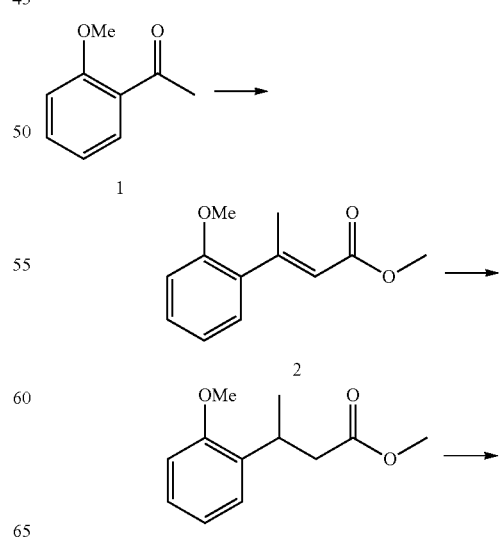

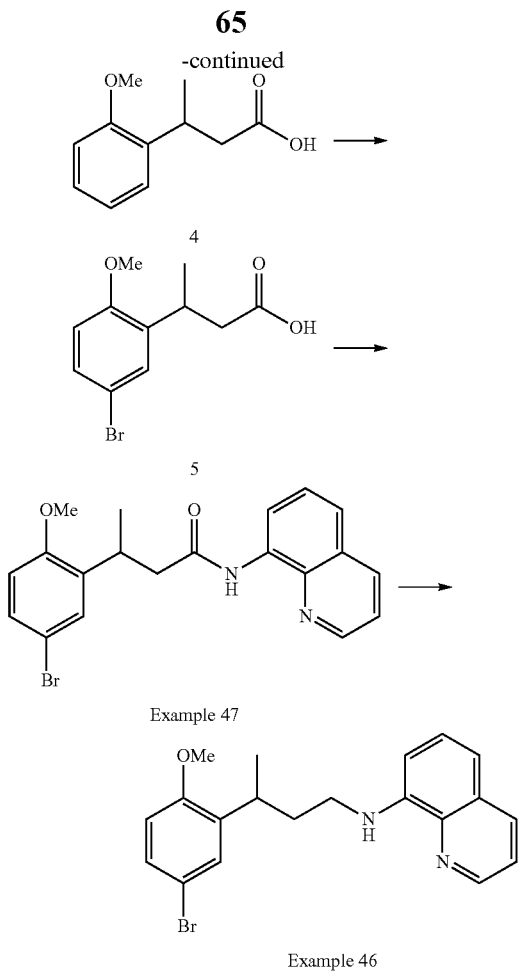

Example 47

Example 46

Procedure:
1. To a solution of Trimethyl phosphonoacetate (14.6 g, 80 mmol) in dry THF (350 mL) was added NaH (3.2 g, 80 mmol, 60%) portionwise at 0° C. After 2 hours stirring at RT, a solution of Compound 1 (10 g, 66.6 mmol) in dry THF (20 mL) was added dropwise at this temp. The resulting solution was stirred at RT for 1 hour and reflux for 2 hours. TLC indicated reaction completion. The reaction mixture was diluted with saturated NH$_4$Cl solution and extracted with EA. The organic extracts were washed with water, brine, dried over anhydrous Na$_2$SO$_4$, filtered and concentrated to give a crude oil. The crude product was purified by silica gel chromatography (5% EA/PE~20% EA/PE) to afford Compound 2 (5.5 g).
$^1$HNMR (CDCl$_3$, 300 MHz) δ: 2.5 (s, 3H), 3.7-3.9 (d, 6H), 5.9 (s, 1H), 6.9 (m, 2H), 7.1-(d, 1H), 7.3 (m, 1H).
2. To a solution of Compound 2 (5.5 g, 26.7 mmol) in THF (80 mL) was added Pd/C (500 mg). The reaction mixture was stirred under a H$_2$ balloon, RT overnight. NMR indicated reaction completion. The residue was filtered and the filter cake washed with THF and the filtrate was concentrated to give Compound 3 (5.5 g).
$^1$HNMR (CDCl$_3$, 300 MHz) δ: 1.2 (d, 3H), 2.4-2.7 (m, 2H), 3.6 (s, 4H), 3.9 (s, 3H), 6.9 (m, 2H), 7.1-7.3 (m, 2H).
3. To a solution of Compound 3 (5.5 g, 26.7 mmol) in THF/H$_2$O (100 mL, 1:1) was added LiOH.H$_2$O (3.36 g, 80 mmol). The reaction mixture was stirred at RT overnight. TLC indicated reaction completion. The solution was remove in vacuo, and the residue was adjusted to pH=3-4 with 6 N HCl solution at 0° C. and extracted with EA. The organic extracts were washed with brine, dried over anhydrous Na$_2$SO$_4$, filtered and concentrated to give Compound 4 (4.7 g).
$^1$HNMR (CDCl$_3$, 300 MHz) δ: 1.2-1.3 (d, 3H), 2.4-2.8 (m, 2H), 3.5-3.7 (m 1H), 3.8-3.9 (s, 3H), 6.8-7.0 (m, 2H), 7.1-7.3 (m, 2H).
4. To a solution of Compound 4 (1 g, 5.15 mmol) in AcOH (20 mL) was added Br$_2$ (1.2 g, 7.7 mmol) dropwise at RT. The reaction mixture was stirred at RT overnight. The residue was treated with water and extracted with DCM. The organic extracts were washed with Na$_2$SO$_3$ solution, brine, dried over anhydrous Na$_2$SO$_4$, filtered and concentrated to give 8-aminoquinoline (1.2 g, 85.7%).
$^1$HNMR (CDCl$_3$, 300 MHz) δ: 1.2-1.3 (d, 3H), 2.4-2.8 (m, 2H), 3.5-3.7 (m 1H), 3.8-3.9 (s, 3H), 6.7-6.8 (d, 1H), 7.2-7.4 (m, 2H).
5. To a solution of Compound 5 (800 mg, 2.94 mmol) in DCM (10 mL) were added Compound 6 (423 mg, 2.94 mmol), EDCI (1.14 g, 5.88 mmol) and DMAP (80 mg). The reaction mixture was stirred at RT overnight. TLC indicated reaction completion. The residue was treated with water and extracted with DCM. The organic extracts were washed with brine, dried over anhydrous Na$_2$SO$_4$, filtered and concentrated to give a crude oil. The crude product was purified by silica gel chromatography to afford Example 47 (500 mg, 42.6%).
$^1$HNMR (CDCl$_3$, 300 MHz) δ: 1.3-1.4 (d, 3H), 2.5-2.9 (m, 2H), 3.7-3.9 (m, 4H), 6.6-6.7 (m, 1H), 7.2-7.4 (m, 2H), 7.4-7.6 (m, 3H), 8.1-8.2 (m, 1H), 8.7-8.9 (m, 2H).
LC-MS: m/z=399.2 (M+1)+.
6. To a solution of Example 47 (450 mg, 1.1 mmol) in THF (20 mL) were added Borane-methyl sulfide complex (0.34 mL, 3.3 mmol, 10 mol/L) dropwise at 0° C. The reaction mixture was stirred at 40° C. for 1 hours. After cooling to 0° C. the residue was diluted with water and extracted with EA. The organic extracts were washed with brine, dried over anhydrous Na$_2$SO$_4$, filtered and concentrated to give a crude oil. The crude product was purified by silica gel chromatography to afford Example 46 (30 mg, 7%).
$^1$HNMR (CDCl$_3$, 300 MHz) δ: 1.2-1.3 (d, 3H), 1.9-2.1 (m, 2H), 3.2-3.5 (m, 3H), 3.8-3.9 (s, 3H), 6.5-6.6 (d, 1H), 6.7-6.8 (d, 1H), 7.0-7.1 (d, 1H), 7.2-7.4 (m, 4H), 8.0-8.1 (m, 1H), 8.7-8.8 (d, 1H).
LC-MS: m/z=385.2 (M+1)+.

Synthesis of Examples 48 and 49

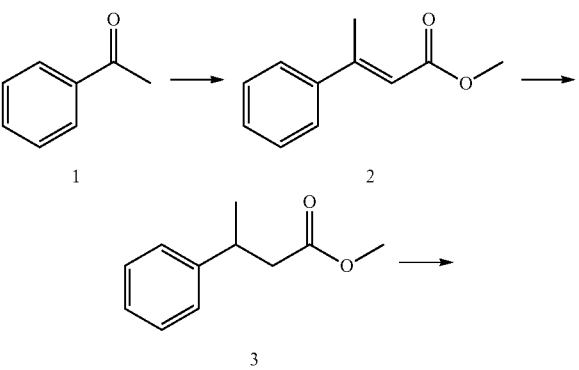

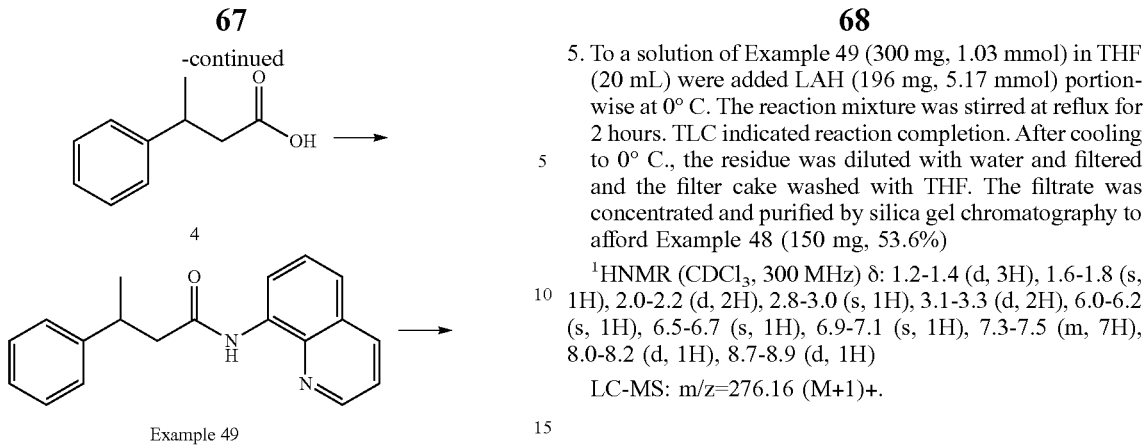

Procedure:
1. To a solution of Trimethyl phosphonoacetate (9.1 g, 50 mmol) in dry THF (200 mL) was added NaH (2 g, 50 mmol, 60%) portionwise at 0° C. After 2 hours stirring at RT, a solution of Compound 1 (5 g, 41.6 mmol) in dry THF (10 mL) was added dropwise at this temp. The resulting solution was stirred at RT for 1 hour and reflux for 2 hours. TLC indicated reaction completion. The reaction mixture was diluted with saturated NH$_4$Cl solution and extracted with EA. The organic extracts were washed with water, brine, dried over anhydrous Na$_2$SO$_4$, filtered and concentrated to give a crude oil. The crude product was purified by silica gel chromatography (5% EA/PE~10% EA/PE) to afford Compound 2 (6 g, 81%).
2. To a solution of Compound 2 (6 g, 33.3 mmol) in THF (50 mL) was added Pd/C (600 mg). The reaction mixture was stirred under a H$_2$ balloon, RT overnight. NMR indicated reaction completion. The residue was filtered and the filter cake washed with THF and the filtrate was concentrated to give Compound 3 (3 g, 51%).
3. To a solution of Compound 3 (3 g, 16.8 mmol) in THF/H$_2$O (50 mL, 1:1) was added LiOH.H$_2$O (3.5 g, 84.2 mmol). The reaction mixture was stirred at RT overnight. TLC indicated reaction completion. The solution was remove in vacuo, and the residue was adjusted to pH=3-4 with 6 N HCl solution at 0° C. and extracted with EA. The organic extracts were washed with brine, dried over anhydrous Na$_2$SO$_4$, filtered and concentrated to give Compound 4 (2.4 g, 88.9%).
4. To a solution of Compound 4 (500 mg, 3 mmol) in DCM (10 mL) were added 8-aminoquinoline (351 mg, 2.44 mmol), EDCI (1.2 g, 6 mmol) and DMAP (75 mg). The reaction mixture was stirred at RT overnight. TLC indicated reaction completion. The residue was treated with water and extracted with DCM. The organic extracts were washed with brine, dried over anhydrous Na$_2$SO$_4$, filtered and concentrated to give a crude oil. The crude product was purified by silica gel chromatography to afford Example 49 (300 mg, 36.7%).

$^1$HNMR (CDCl$_3$, 300 MHz) δ: 1.3-1.5 (d, 3H), 2.8-3.0 (d, 2H), 3.3-3.5 (m, 1H), 7.2-7.4 (m, 1H), 7.4-7.6 (s, 3H), 7.6-7.7 (s, 3H), 8.1-8.3 (m, 1H), 8.6-8.7 (m, 1H), 9.6-9.8 (m, 1H)

LC-MS: m/z=290.14 (M+23)$^+$.

5. To a solution of Example 49 (300 mg, 1.03 mmol) in THF (20 mL) were added LAH (196 mg, 5.17 mmol) portionwise at 0° C. The reaction mixture was stirred at reflux for 2 hours. TLC indicated reaction completion. After cooling to 0° C., the residue was diluted with water and filtered and the filter cake washed with THF. The filtrate was concentrated and purified by silica gel chromatography to afford Example 48 (150 mg, 53.6%)

$^1$HNMR (CDCl$_3$, 300 MHz) δ: 1.2-1.4 (d, 3H), 1.6-1.8 (s, 1H), 2.0-2.2 (d, 2H), 2.8-3.0 (s, 1H), 3.1-3.3 (d, 2H), 6.0-6.2 (s, 1H), 6.5-6.7 (s, 1H), 6.9-7.1 (s, 1H), 7.3-7.5 (m, 7H), 8.0-8.2 (d, 1H), 8.7-8.9 (d, 1H)

LC-MS: m/z=276.16 (M+1)+.

Synthesis of Example 50

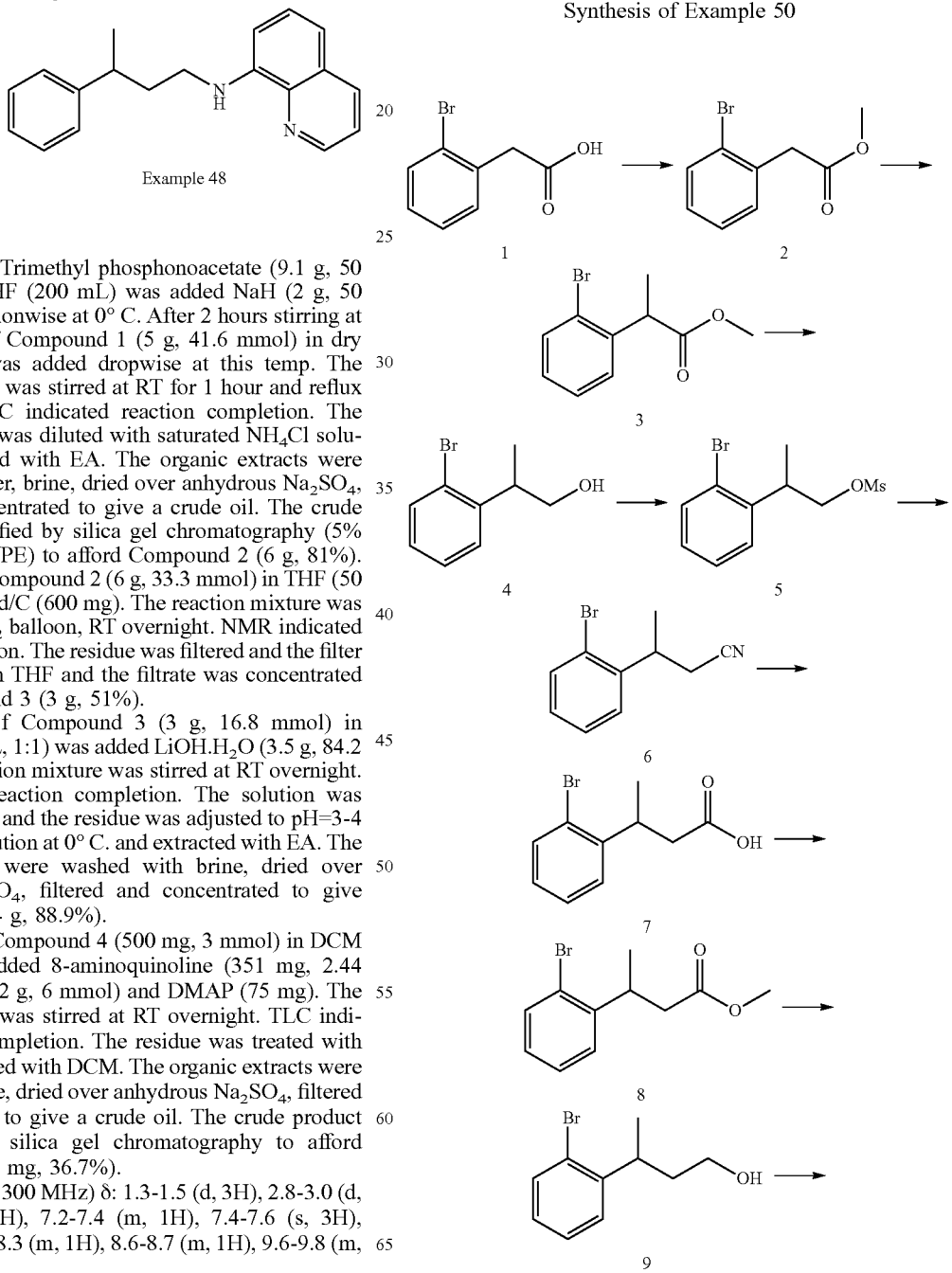

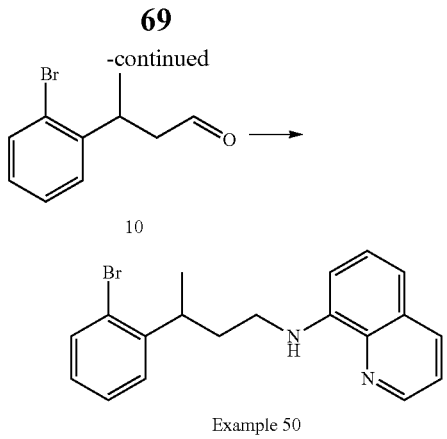

Example 50

Procedure:
1. To a solution of Compound 1 (10 g, 46 mmol) in MeOH (100 mL) was added $SOCl_2$ (10 mL) dropwise at 0° C. The resulting solution was stirred at reflux overnight. TLC indicated reaction was completed. The solvent was removed in vacuum, and the residue was treated with water and extracted with EA. The organic extracts were washed with saturated $NaHCO_3$ solution, brine, dried over anhydrous $Na_2SO_4$, filtered and concentrated to give Compound 2 (10 g, 94.3%).
2. To a solution of i-$Pr_2NH$ (8.5 mL, 65.7 mmol) in dry THF (100 mL) was added n-BuLi (26 mL, 65.7 mmol) dropwise at −78° C. under $N_2$ and stirred for 30 min. Then a solution of Compound 2 (10 g, 43.8 mmol) in dry THF (100 mL) was added dropwise and stirred at this temp for 1 hour. $CH_3I$ (9.3 g, 65.7 mmol) was added. The resulting solution was stirred at RT overnight. The residue was treated with water and extracted with EA. The organic extracts were washed with saturated water, brine, dried over anhydrous $Na_2SO_4$, filtered and concentrated to give Compound 3 (10 g, 94%).
$^1$HNMR ($CDCl_3$, 300 MHz) δ: 1.4-1.5 (d, 3H), 3.7 (s, 3H), 4.2-4.3 (m, 1H), 7.1-7.2 (m, 1H), 7.2-7.4 (m, 2H), 7.5-7.6 (m, 1H).
3. To a suspension mixture of LAH (1.6 g, 41.3 mmol) in dry THF (10 mL) was added a solution of Compound 3 (10 g, 41.3 mmol) in dry THF (20 mL) dropwise at 0° C. under $N_2$. The reaction mixture was heated to reflux for 3 hours. TLC indicated reaction was completed. The residue was diluted with water and filtered and the filter cake washed with THF. The filtrate was concentrated to afford Compound 4 (8 g, 88.4%).
$^1$HNMR ($CDCl_3$, 300 MHz) δ: 1.2-1.3 (d, 3H), 3.4-3.6 (m, 1H), 3.6-3.9 (m, 2H), 7.1-7.2 (m, 1H), 7.2-7.4 (m, 2H), 7.5-7.6 (m, 1H).
4. To a solution of Compound 4 (8 g, 37.4 mmol) in DCM (100 mL) was added TEA (7.8 mL, 56 mmol), then MsCl (5.1 g, 44.8 mmol) was added dropwise at 0° C. The reaction mixture was stirred at RT for 2 hours. TLC indicated reaction completion. The residue was treated with water and extracted with DCM. The organic extracts were washed with brine, dried over anhydrous $Na_2SO_4$, filtered and concentrated to give Compound 5 (9 g, 82.6%).
$^1$HNMR ($CDCl_3$, 300 MHz) δ: 1.2-1.3 (d, 3H), 3.4-3.6 (m, 1H), 3.6-3.9 (m, 2H), 7.1-7.2 (m, 1H), 7.2-7.4 (m, 2H), 7.5-7.6 (m, 1H).
5. To a solution of Compound 5 (9 g, 30.8 mmol) in MeCN (50 mL) was added TMSCN (6.1 g, 61.6 mol) at 0° C. a solution of TBAF (12 g, 46.2 mmol) in dry THF (50 mL) was added dropwise. The reaction mixture was heated to 80° C. overnight. TLC indicated reaction completion. The solvent was removed in vacuum, and the residue was treated with water and extracted with EA. The organic extracts were washed with water, brine, dried over anhydrous $Na_2SO_4$, filtered and concentrated to give a crude oil. The crude product was purified by silica gel chromatography to afford Compound 6 (4 g, 58.8%).
$^1$HNMR ($CDCl_3$, 300 MHz) δ: 1.4-1.5 (d, 3H), 2.5-2.7 (m, 2H), 3.6-3.8 (m, 1H), 7.1-7.2 (m, 1H), 7.2-7.4 (m, 2H), 7.5-7.6 (m, 1H).
6. To a solution of Compound 6 (4 g, 17.9 mmol) in EtOH (40 mL) was added 10% NaOH solution (40 mL). The reaction mixture was stirred at 90° C. overnight. TLC indicated reaction was completed. The solvent was removed in vacuum, and the residue was treated with water and extracted with DCM. The organic extracts were washed with water, brine, dried over anhydrous $Na_2SO_4$, filtered and concentrated to give Compound 7 (3.5 g, 81.4%).
$^1$HNMR ($CDCl_3$, 300 MHz) δ: 1.3-1.4 (d, 3H), 2.4-2.8 (m, 2H), 3.6-3.8 (m, 1H), 7.1-7.2 (m, 1H), 7.2-7.4 (m, 2H), 7.5-7.6 (m, 1H).
7. To a solution of Compound 7 (1 g, 46 mmol) in MeOH (100 mL) was added $SOCl_2$ (10 mL) dropwise at 0° C. The resulting solution was stirred at reflux overnight. TLC indicated reaction was completed. The solvent was removed in vacuum, and the residue was treated with water and extracted with EA. The organic extracts were washed with saturated $NaHCO_3$ solution, brine, dried over anhydrous $Na_2SO_4$, filtered and concentrated to give Compound 8 (1 g, 95.2%).
$^1$HNMR ($CDCl_3$, 300 MHz) δ: 1.3-1.4 (d, 3H), 2.4-2.8 (m, 2H), 3.6-3.7 (s, 3H), 3.7-3.9 (m, 1H), 7.1-7.2 (m, 1H), 7.2-7.4 (m, 2H), 7.5-7.6 (m, 1H).
8. To a solution of Compound 8 (1 g, 3.9 mmol) in THF (20 mL) were added LAH (150 mg, 3.9 mmol) portionwise at 0° C. The reaction mixture was stirred at RT for 2 hours. TLC indicated reaction was completed. After cooling to 0° C., the residue was diluted with water and filtered and the filter cake washed with THF. The filtrate was concentrated to afford Compound 9 (800 mg, 90%).
$^1$HNMR ($CDCl_3$, 300 MHz) δ: 1.2-1.3 (d, 3H), 1.8-2.0 (m, 2H), 3.4-3.5 (m, 1H), 3.6-3.7 (m, 2H), 7.1-7.2 (m, 1H), 7.2-7.4 (m, 2H), 7.5-7.6 (m, 1H).
9. To a solution of Oxalyl chloride (530 mg, 4.2 mmol) in DCM (10 mL) was added dry DMSO (650 mg, 8.3 mmol) dropwise at −78° C. under $N_2$ protection. After 10 min stirring, a solution of Compound 9 (500 mg, 2.8 mmol) in DCM (5 mL) was added dropwise. Then stirred at this temp for 30 min. TEA (1.2 mL, 8.3 mmol) was added dropwise. The resulting solution was allowed to slowly warm to RT. The residue was treated with water and extracted with DCM. The organic extracts were concentrated and purified by silica gel chromatography to afford Compound 10 (300 mg, 60.6%).
$^1$HNMR ($CDCl_3$, 300 MHz) δ: 1.2-1.3 (d, 3H), 2.6-2.9 (m, 2H), 3.8-3.9 (m, 1H), 7.1-7.2 (m, 1H), 7.2-7.4 (m, 2H), 7.5-7.6 (m, 1H), 9.7-9.8 (s, 1H).
10. To a solution of Compound 10 (150 mg, 0.66 mmol) in MeOH (2 mL) were added 8-aminoquinoline (96 mg, 0.66 mmol), $NaCNBH_3$ (42 mg, 0.66 mmol) and AcOH (80 mg, 1.3 mmol). The resulting solution was stirred at RT overnight. The residue was purified by silica gel chromatography to afford Example 50 (120 mg, 51%).
$^1$HNMR ($CDCl_3$, 300 MHz) δ: 1.3-1.4 (d, 3H), 2.0-2.2 (m, 2H), 3.2-3.4 (m, 2H), 3.4-3.5 (m, 1H), 6.1-6.2 (m, 1H), 6.6-6.7 (m, 1H), 7.0-7.2 (m, 2H), 7.2-7.4 (m, 5H), 7.5-7.6 (d, 1H). 8.0-8.1 (d, 1H), 8.7-8.8 (d, 1H).

LC-MS: m/z=355.1 (M+1)+.

Synthesis of Example 51

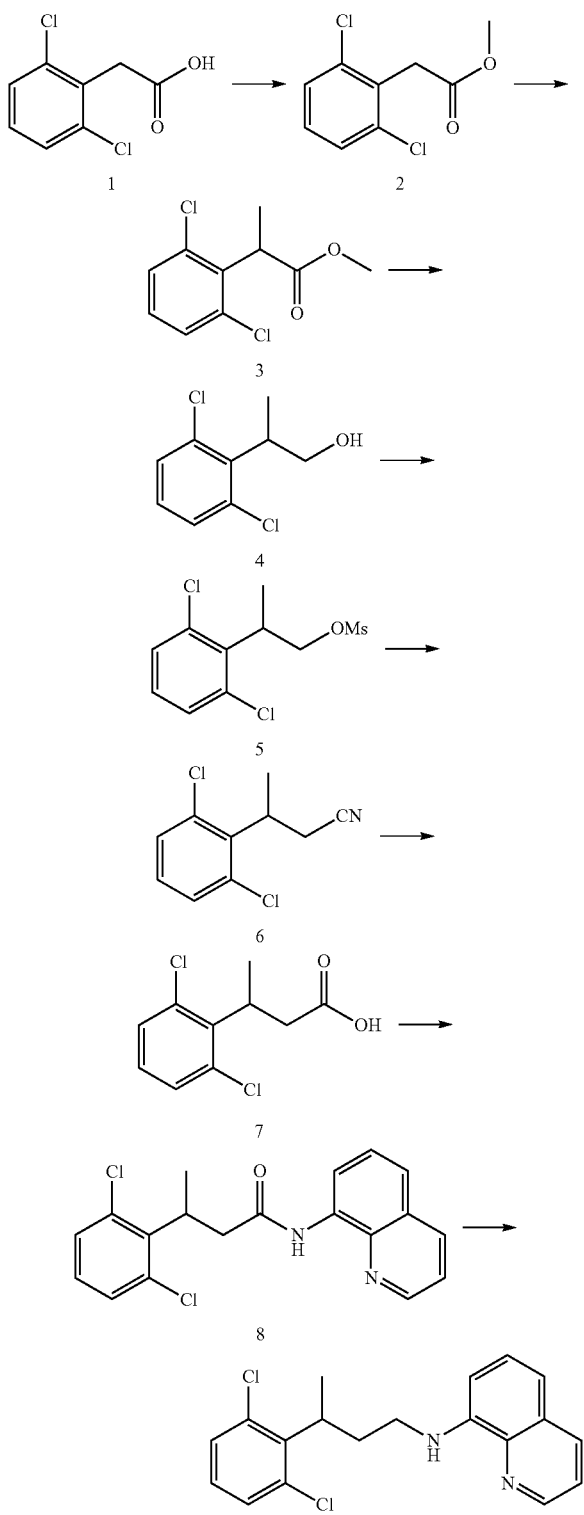

Procedure:

1. To a solution of Compound 1 (10 g, 48.8 mmol) in MeOH (100 mL) was added SOCl$_2$ (10 mL) dropwise at 0° C. The resulting solution was stirred at reflux overnight. TLC indicated reaction was completed. The solvent was removed in vacuum, and the residue was treated with water and extracted with EA. The organic extracts were washed with saturated NaHCO$_3$ solution, brine, dried over anhydrous Na$_2$SO$_4$, filtered and concentrated to give Compound 2 (10 g).

2. To a solution of i-Pr$_2$NH (8.8 mL, 68.3 mmol) in dry THF (100 mL) was added n-BuLi (27.1 mL, 68.3 mmol) dropwise at −78° C. under N$_2$ and stirred for 30 min. Then a solution of Compound 2 (10 g, 45.7 mmol) in dry THF (100 mL) was added dropwise and stirred at this temp for 1 hour. CH$_3$I (9.7 g, 68.3 mmol) was added. The resulting solution was stirred at RT overnight. The residue was treated with water and extracted with EA. The organic extracts were washed with saturated water, brine, dried over anhydrous Na$_2$SO$_4$, filtered and concentrated to give Compound 3 (10 g).

3. To a suspension mixture of LAH (1.6 g, 43 mmol) in dry THF (40 mL) was added a solution of Compound 3 (10 g, 43 mmol) in dry THF (20 mL) dropwise at 0° C. under N$_2$. The reaction mixture was heated to reflux for 3 hours. TLC indicated reaction was completed. The residue was diluted with water and filtered and the filter cake washed with THF. The filtrate was concentrated to afford Compound 4 (8 g).

4. To a solution of Compound 4 (8 g, 39 mmol) in DCM (100 mL) was added TEA (8.1 mL, 58.4 mmol), then MsCl (5.3 g, 46.8 mmol) was added dropwise at 0° C. The reaction mixture was stirred at RT for 2 hours. TLC indicated reaction completion. The residue was treated with water and extracted with DCM. The organic extracts were washed with brine, dried over anhydrous Na$_2$SO$_4$, filtered and concentrated to give Compound 5 (8.7 g).

5. To a solution of Compound 5 (8.7 g, 30.8 mmol) in MeCN (50 mL) was added TMSCN (6.1 g, 61.6 mol) at 0° C., a solution of TBAF (12 g, 46.2 mmol) in dry THF (50 mL) was added dropwise. The reaction mixture was heated to 80° C. overnight. TLC indicated reaction completion. The solvent was removed in vacuum, and the residue was treated with water and extracted with EA. The organic extracts were washed with water, brine, dried over anhydrous Na$_2$SO$_4$, filtered and concentrated to give a crude oil. The crude product was purified by silica gel chromatography to afford Compound 6 (4.5 g).

6. To a solution of Compound 6 (4.5 g, 21 mmol) in EtOH (40 mL) was added 10% NaOH solution (40 mL). The reaction mixture was stirred at 90° C. overnight. TLC indicated reaction was completed. The solvent was removed in vacuum, and the residue was treated with water and extracted with DCM. The organic extracts were washed with water, brine, dried over anhydrous Na$_2$SO$_4$, filtered and concentrated to give Compound 7 (3.7 g).

7. To a solution of Compound 7 (1 g, 4.3 mmol) in DCM (40 mL) was added 8-aminoquinoline (0.62 g, 4.3 mmol). EDCI (1.65 g, 8.6 mmol) and DMAP (260 mg, 2.2 mmol) was added and the mixture was stirred at RT for overnight. Washed by water and extracted by DCM. Dried and concentrated, purified by silica gel to give Compound 8 (600 mg).

8. To a solution of Compound 8 (400 mg, 1.11 mmol) in THF (10 mL) were added LAH (190 mg, 5 mmol) portionwise at 0° C. The reaction mixture was stirred at 70° C. for 2 hours. TLC indicated reaction was completed. After cooling to 0° C., the residue was diluted with water and filtered and the filter cake washed with THF. The filtrate was concentrated to afford Example 51 (150 mg).

$^1$HNMR (CDCl$_3$, 300 MHz) δ: 1.4-1.5 (d, 3H), 2.2 (m, 1H), 2.5 (m, 1H), 3.2 (m, 2H), 4.0 (m, 1H), 6.6 (d, 1H), 7.0 (m, 2H), 7.2-7.4 (m, 5H), 8.0 (d, 2H).

LC-MS: m/z=345.1 (M+1)+

Synthesis of Example 52

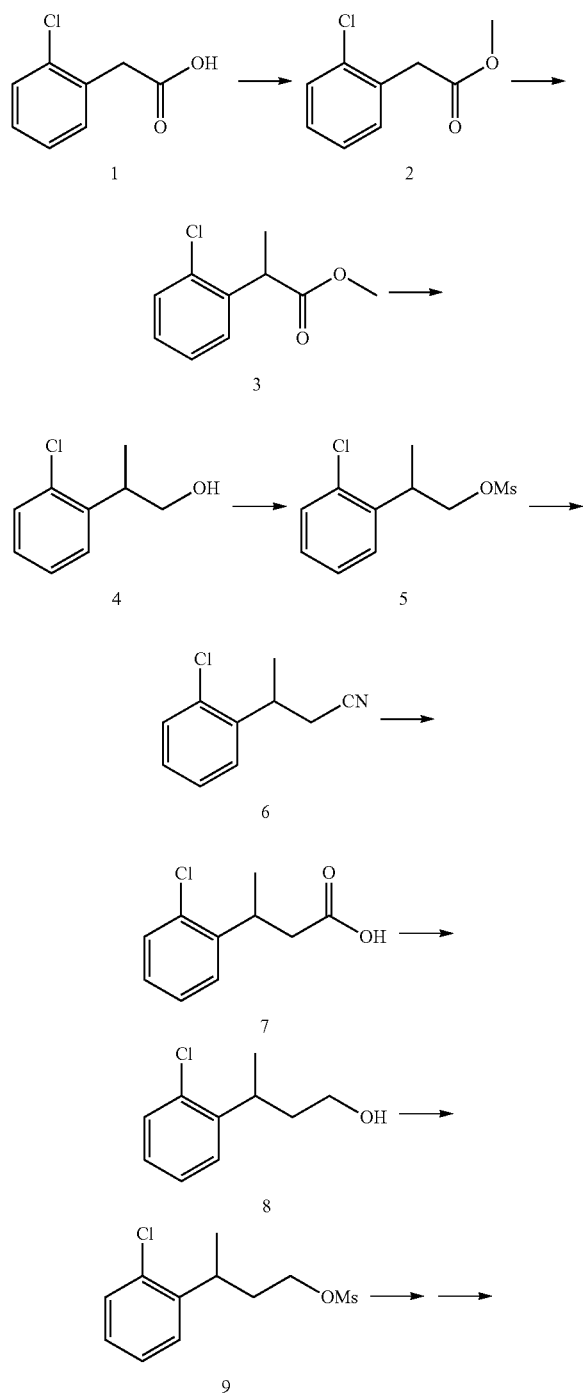

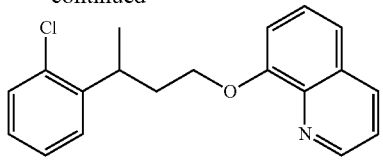

Example 52

Procedure:
1. To a solution of Compound 1 (10 g, 58.8 mmol) in MeOH (100 mL) was added SOCl$_2$ (13 mL) dropwise at 0° C. The resulting solution was stirred at reflux overnight. TLC indicated reaction was completed. The solvent was removed in vacuum, and the residue was treated with water and extracted with EA. The organic extracts were washed with saturated NaHCO$_3$ solution, brine, dried over anhydrous Na$_2$SO$_4$, filtered and concentrated to give Compound 2 (10 g).
2. To a solution of i-Pr$_2$NH (10.5 mL, 81.4 mmol) in dry THF (100 mL) was added n-BuLi (32.2 mL, 81.4 mmol) dropwise at −78° C. under N$_2$ and stirred for 30 min. Then a solution of Compound 2 (10 g, 54.34 mmol) in dry THF (100 mL) was added dropwise and stirred at this temp for 1 hour. CH$_3$I (11.5 g, 81.4 mmol) was added. The resulting solution was stirred at RT overnight. The residue was treated with water and extracted with EA. The organic extracts were washed with saturated water, brine, dried over anhydrous Na$_2$SO$_4$, filtered and concentrated to give Compound 3 (10 g).
3. To a suspension mixture of LAH (2.2 g, 50.5 mmol) in dry THF (40 mL) was added a solution of Compound 3 (10 g, 50.5 mmol) in dry THF (20 mL) dropwise at 0° C. under N$_2$. The reaction mixture was heated to reflux for 3 hours. TLC indicated reaction was completed. The residue was diluted with water and filtered and the filter cake washed with THF. The filtrate was concentrated to afford Compound 4 (8.2 g).
4. To a solution of Compound 4 (8.2 g, 48.2 mmol) in DCM (100 mL) was added TEA (10 mL, 72.3 mmol), then MsCl (6.6 g, 57.8 mmol) was added dropwise at 0° C. The reaction mixture was stirred at RT for 2 hours. TLC indicated reaction completion. The residue was treated with water and extracted with DCM. The organic extracts were washed with brine, dried over anhydrous Na$_2$SO$_4$, filtered and concentrated to give Compound 5 (9 g).
5. To a solution of Compound 5 (9 g, 36.3 mmol) in MeCN (50 mL) was added TMSCN (7.1 g, 72.6 mol) at 0° C., a solution of TBAF (14.1 g, 54.4 mmol) in dry THF (50 mL) was added dropwise. The reaction mixture was heated to 80° C. overnight. TLC indicated reaction completion. The solvent was removed in vacuum, and the residue was treated with water and extracted with EA. The organic extracts were washed with water, brine, dried over anhydrous Na$_2$SO$_4$, filtered and concentrated to give a crude oil. The crude product was purified by silica gel chromatography to afford Compound 6 (3.9 g).
6. To a solution of Compound 6 (3.9 g, 21.7 mmol) in EtOH (40 mL) was added 10% NaOH solution (40 mL). The reaction mixture was stirred at 90° C. overnight. TLC indicated reaction was completed. The solvent was removed in vacuum, and the residue was treated with water and extracted with DCM. The organic extracts were washed with water, brine, dried over anhydrous Na$_2$SO$_4$, filtered and concentrated to give Compound 7 (3.4 g).

7. To a solution of Compound 7 (500 mg, 2.52 mmol) and TEA (510 mg, 5.04 mmol) in THF (20 mL) were added isobutyl carbonochloridate (420 mg, 3.28 mmol) dropwise at 0 SC The reaction mixture was stirred at RT for 1 hour. NaBH4 (190 mg, 5.04 mmol) was added and the mixture was stirred at RT for 2 hours. The residue was diluted with water and filtered and the filter cake washed with THF. The filtrate was concentrated to afford Compound 8 (200 mg).
8. To a solution of Compound 8 (200 mg, 1.09 mmol) in DCM (10 mL) was added TEA (166 mg, 1.64 mmol). MsCl (150 mg, 1.31 mmol) was added slowly with ice-bath. The resulting solution was allowed to slowly warm to RT and stirred for 30 mins. The residue was treated with water and extracted with DCM. The organic extracts were concentrated and purified by silica gel chromatography to afford Compound 9 (250 mg).
9. To a solution of 8-hydroxyquinoline (140 mg, 0.94 mmol) in DMF (5 mL) were added NaH (75 mg, 1.88 mmol, 60%), Compound 9 (250 mg, 0.94 mmol) was added and he resulting solution was stirred at 60° C. for 3 hours. The residue was treated with water and extracted with EA. The residue was purified by silica gel chromatography to afford Example 52 (80 mg).

$^1$HNMR (CDCl$_3$, 300 MHz) δ: 1.3-1.4 (d, 3H), 2.3-2.4 (m, 2H), 3.2-3.4 (m, 2H), 3.6 (m, 1H), 4.0-4.3 (m, 2H), 6.9 (m, 1H), 7.0-7.5 (m, 7H), 8.1 (d, 1H), 8.9 (s, 1H).

LC-MS: m/z=312.1 (M+1)+.

Synthesis of Example 53

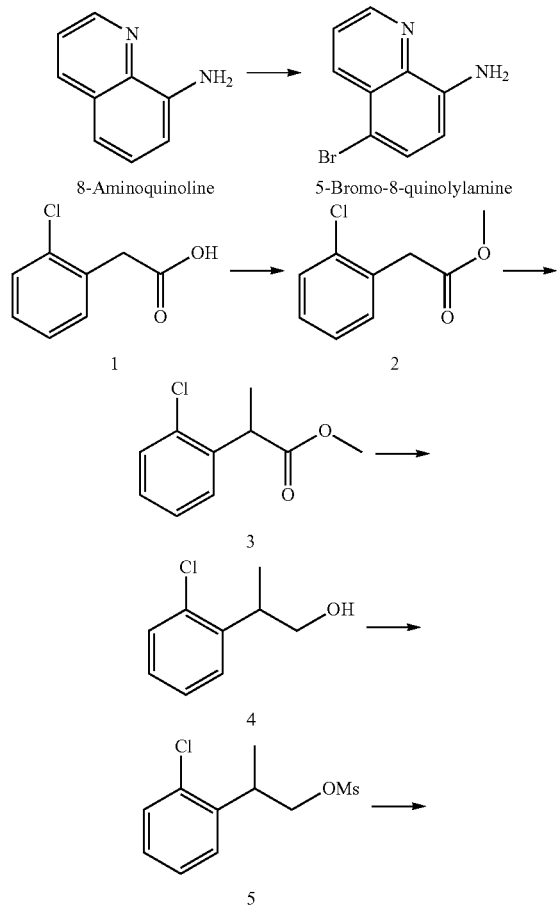

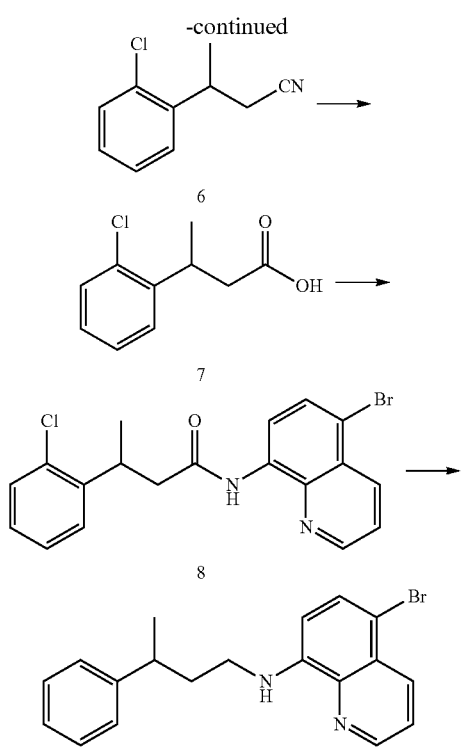

Example 53

Procedure:

Synthesis of 5-bromo-8-quinolylamine

To a solution of 8-aminoquinoline (1 g, 4.8 mmol) in CH3CN (30 mL) were added NBS (1.28 g, 7.2 mmol). The reaction mixture was stirred at RT for 2 hour. The residue was treated with water and extracted with EA. The extracts were concentrated and the residue purified by silica gel chromatography to afford 5-bromo-8-quinolylamine (760 mg).

1. To a solution of Compound 1 (10 g, 58.8 mmol) in MeOH (100 mL) was added SOCl$_2$ (13 mL) dropwise at 0° C. The resulting solution was stirred at reflux overnight. TLC indicated reaction was completed. The solvent was removed in vacuum, and the residue was treated with water and extracted with EA. The organic extracts were washed with saturated NaHCO$_3$ solution, brine, dried over anhydrous Na$_2$SO$_4$, filtered and concentrated to give Compound 2 (10 g).
2. To a solution of i-Pr$_2$NH (10.5 mL, 81.4 mmol) in dry THF (100 mL) was added n-BuLi (32.2 mL, 81.4 mmol) dropwise at −78° C. under N$_2$ and stirred for 30 min. Then a solution of Compound 2 (10 g, 54.34 mmol) in dry THF (100 mL) was added dropwise and stirred at this temp for 1 hour. CH$_3$I (11.5 g, 81.4 mmol) was added. The resulting solution was stirred at RT overnight. The residue was treated with water and extracted with EA. The organic extracts were washed with saturated water, brine, dried over anhydrous Na$_2$SO$_4$, filtered and concentrated to give Compound 3 (10 g).
3. To a suspension mixture of LAH (2.2 g, 50.5 mmol) in dry THF (40 mL) was added a solution of Compound 3 (10 g, 50.5 mmol) in dry THF (20 mL) dropwise at 0° C. under N$_2$. The reaction mixture was heated to reflux for 3 hours. TLC indicated reaction was completed. The residue was diluted with water and filtered and the filter cake washed with THF. The filtrate was concentrated to afford Compound 4 (8.2 g).
4. To a solution of Compound 4 (8.2 g, 48.2 mmol) in DCM (100 mL) was added TEA (10 mL, 72.3 mmol), then MsCl (6.6 g, 57.8 mmol) was added dropwise at 0° C. The reaction mixture was stirred at RT for 2 hours. TLC indicated reaction completion. The residue was treated with water and extracted with DCM. The organic extracts were washed with brine, dried over anhydrous Na$_2$SO$_4$, filtered and concentrated to give Compound 5 (9 g).
5. To a solution of Compound 5 (9 g, 36.3 mmol) in MeCN (50 mL) was added TMSCN (7.1 g, 72.6 mol) at 0° C., a solution of TBAF (14.1 g, 54.4 mmol) in dry THF (50 mL) was added dropwise. The reaction mixture was heated to 80° C. overnight. TLC indicated reaction completion. The solvent was removed in vacuum, and the residue was treated with water and extracted with EA. The organic extracts were washed with water, brine, dried over anhydrous Na$_2$SO$_4$, filtered and concentrated to give a crude oil. The crude product was purified by silica gel chromatography to afford Compound 6 (3.9 g).
6. To a solution of Compound 6 (3.9 g, 21.7 mmol) in EtOH (40 mL) was added 10% NaOH solution (40 mL). The reaction mixture was stirred at 90° C. overnight. TLC indicated reaction was completed. The solvent was removed in vacuum, and the residue was treated with water and extracted with DCM. The organic extracts were washed with water, brine, dried over anhydrous Na$_2$SO$_4$, filtered and concentrated to give Compound 7 (3.4 g).
7. To a solution of Compound 7 (300 mg, 1.51 mmol) in DCM (20 mL) was added 5-bromo-8-quinolylamine (350 mg, 1.51 mmol). EDCI (570 mg, 3 mmol) and DMAP (90 mg, 0.75 mmol) was added. The mixture was stirred at RT for overnight. The residue was treated with water and extracted with DCM. The organic extracts were concentrated and purified by silica gel chromatography to afford Compound 8 (300 mg).
8. To a solution of Compound 8 (200 mg, 0.5 mmol) in THF (10 mL) were added LAH (95 mg, 2.5 mmol) The mixture was stirred at 60° C. for 3 hours. The residue was treated with water. Filtered out and concentrated to afford Example 53 (80 mg).

$^1$HNMR (CDCl$_3$, 300 MHz) δ: 1.3-1.4 (d, 3H), 2.1 (m, 2H), 3.2-3.3 (m, 2H), 3.5 (m, 1H), 6.4 (d, 2H), 7.2-7.6 (m, 6H), 8.4 (d, 1H), 8.7 (s, 1H).
LC-MS: m/z=355.1 (M+1)+.

Synthesis of Example FLS-116

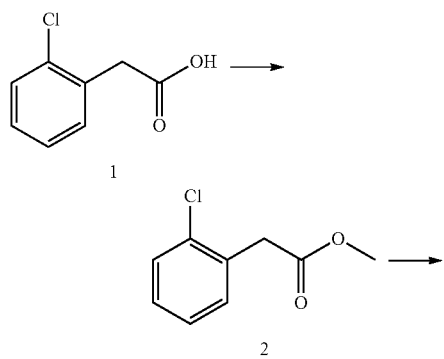

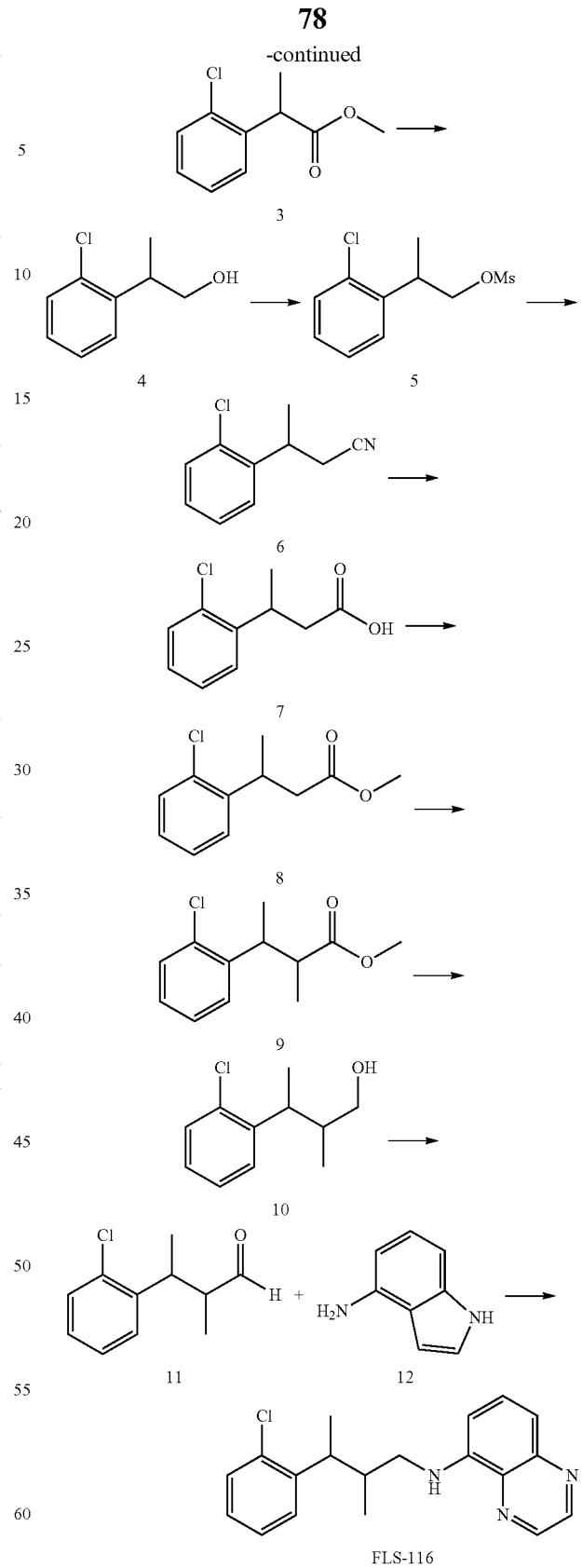

Procedure:
1. To a solution of 2-(2-chlorophenyl)acetic acid Compound 1 (20 g, 117.2 mmol) in MeOH (250 mL) at 0° C. was added SOCl$_2$ (20.9 g, 175.8 mmol) dropwise. The mixture was stirred at 70° C. for 4 hours, concentrated, diluted with H$_2$O and extracted with EtOAc twice. The combined organic extracts were washed with brine, dried and concentrated to give 21.5 g of methyl 2-(2-chlorophenyl) acetate Compound 2.

2. To a solution of methyl 2-(2-chlorophenyl)acetate Compound 2 (21.5 g, 116.8 mmol) in THF (100 mL) at −78° C. was added LDA (175.3 mmol, 200 mL) dropwise. The mixture was stirred at −40° C. for 2 hours, cooled to −78° C. and MeI (24.9 g, 175.3 mmol) in THF (30 mL) was added dropwise. The mixture was stirred at room temp overnight. The reaction was diluted with water and extracted with EtOAc. The combined organic extracts were dried and concentrated to give 23 g of crude methyl 2-(2-chlorophenyl)propanoate Compound 3.

3. To a solution of methyl 2-(2-chlorophenyl)propanoate Compound 3 (15 g, 75.75 mmol) in dry THF (150 mL) at 0° C. was added LiAlH$_4$ (3.42 g, 90.9 mmol) slowly and the mixture stirred for 1 hour. The reaction was diluted with water, filtered and the filtrate extracted with EtOAc. The combined extracts were concentrated to give 11 g of 2-(2-chlorophenyl)propan-1-ol Compound 4.

4. To a solution of 2-(2-chlorophenyl)propan-1-ol Compound 4 (10 g, 58.8 mmol) and TEA (8.9 g, 88 mmol) in DCM (100 mL) at 0° C. MsCl (8 g, 70.5 mmol) was added dropwise. The mixture was stirred at RT for 1 hour, diluted with water and extracted with DCM. The combined organic extracts were dried and concentrated to give 14 g of 2-(2-chlorophenyl)propyl methanesulfonate Compound 5.

5. To a solution of 2-(2-chlorophenyl)propyl methanesulfonate Compound 5 (14 g, 56.4 mmol) in dry CH$_3$CN (80 mL) at 0° C. was added TMSCN (11.2 g, 112.8 mmol). TBAF (22.2 g, 85 mmol) in THF (80 mL) was added dropwise. The reaction was stirred at 80° C. overnight, the mixture was concentrated, diluted with water and extracted with EtOAc. The combined extracts were concentrated to give 7 g of 3-(2-chlorophenyl)butanenitrile Compound 6.

6. To a solution of 3-(2-chlorophenyl)butanenitrile Compound 6 (7 g, 39.1 mmol) in EtOH (70 mL) was added NaOH solution (10%, 70 mL) and the mixture was stirred at 80° C. overnight. The EtOH was removed and the mixture was acidified to pH=3 with HCl (3 M) and extracted with DCM. The combined extracts were dried and concentrated to give 8 g of 3-(2-chlorophenyl)butanoic acid Compound 7.

7. To a solution of 3-(2-chlorophenyl)butanoic acid Compound 7 (8 g, 40.4 mmol) in MeOH (80 mL) at 0° C. was added SOCl$_2$ (7.1 g, 60.0 mmol) dropwise. The mixture was stirred at 70° C. for 2 hours and concentrated. Water was added and the mixture was extracted with EtOAc twice, the combined extracts washed by brine, dried and concentrated to give 7 g of methyl 3-(2-chlorophenyl) butanoate Compound 8.

8. To a solution of methyl 3-(2-chlorophenyl)butanoate Compound 8 (7 g, 33 mmol) in THF (30 mL) at −78° C. LDA (49.5 mmol, 70 mL) was added dropwise. The reaction mixture was stirred at −40° C. for 2 hours, cooled to −78° C. and MeI (9.3 g, 33 mmol) in THF (10 mL) was added dropwise. The mixture was stirred at room temp overnight, diluted with water and extracted with EtOAc. The combined extracts were dried and concentrated to give 6 g of methyl 3-(2-chlorophenyl)-2-methyl-butanoate Compound 9.

9. To solution of methyl 3-(2-chlorophenyl)-2-methyl-butanoate Compound 9 (6 g, 26.5 mmol) in dry THF (100 mL) at 0° C. was added LiAlH$_4$ (1.1 g, 29 mmol) slowly. After 1 hour the mixture was diluted with water, filtered and the filtrate extracted withed EtOAc. The combined extracts were concentrated to give 4 g of 3-(2-chlorophenyl)-2-methyl-butan-1-ol Compound 10.

10. To a solution of DMSO (3.1 g, 40.4 mmol) in DCM (80 mL) at −78° C. was added (COCl)$_2$ (5.2 g, 40.4 mmol). After 15 min., 3-(2-chlorophenyl)-2-methyl-butan-1-ol Compound 10 (4 g, 20.2 mmol) in DCM (10 mL) was added dropwise to the mixture at −78° C. The mixture was stirred at −78° C. for 1 hour and Et$_3$N (8.1 g, 80.8 mmol) was added. The reaction was warmed to RT and diluted with water and extracted with DCM. The combined extracts were dried and concentrated to give 3 g of 3-(2-chlorophenyl)-2-methyl-butanal Compound 11.

11. To a solution of 3-(2-chlorophenyl)-2-methylbutanal, Compound 11, (500 mg, 2.55 mmol) and Compound 12 (0.336 g, 2.55 mmol) in MeOH (5 mL) were added NaCNBH$_3$ (160 mg, 2.55 mmol). HOAc (290 mg, 2.55 mmol) was added and the mixture was stirred at RT for overnight. The reaction mixture was concentrated and the residue purified by silica gel column and Prep-HPLC to give 24.6 mg of FLS-116.

$^1$HNMR (CDCl$_3$, 300 MHz) δ: 1.0-1.2 (m, 3H), 1.3-1.5 (m, 3H), 2.2 (m, 1H), 3.0-3.5 (m, 3H), 6.2 (m, 1H), 6.4 (s, 1H), 6.9 (t, 1H), 7.0-7.5 (m, 6H). LC-MS: m/z=313.2 (M+1)$^+$.

Synthesis of Example FLS-114

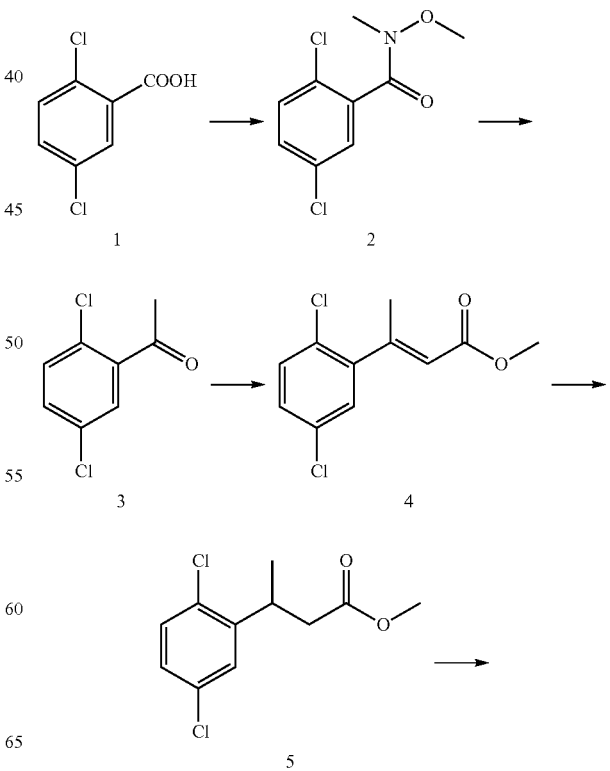

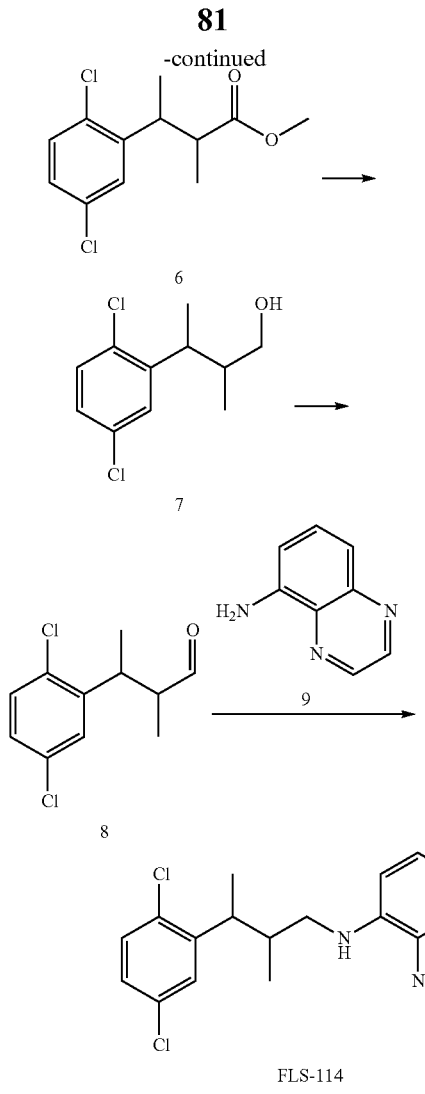

FLS-114 filtered and concentrated to give an oil which was purified by silica gel chromatography to give 7 g of Compound 4.

4. To a solution of Compound 4 (7 g, 28.7 mmol) in THF (80 mL) was added Pd/C (500 mg). The reaction mixture was stirred under H$_2$ (balloon) RT overnight. The mixture was filtered, the filter cake washed with THF and the filtrate concentrated to give 6 g of Compound 5.

5. To a solution of Compound 5 (6 g, 24.3 mmol) in THF (20 mL) at −78° C. was added LDA (36.5 mmol, 50 mL) dropwise. The mixture was stirred at −40° C. for 2 hours, cooled to −78° C. and MeI (5.2 g, 36.5 mmol) in THF (10 mL) was added dropwise. The mixture was stirred at room temp overnight, diluted with water and extracted with EtOAc. The combined organic extracts were dried and concentrated to give 5.4 g of crude Compound 6.

6. To a solution of Compound 6 (5.4 g, 20.8 mmol) in dry THF (100 mL) at 0° C. was added LiAlH$_4$ (0.79 g, 20.8 mmol) slowly, the mixture stirred for 1 hour, diluted with water, filtered and the filter cake washed withed EtOAc. The filtrate was concentrated to give 4.1 g of Compound 7.

7. To a solution of oxalyl chloride (4.47 g, 35.2 mmol) in DCM (50 mL) at −78° C. was added dry DMSO (2.75 g, 35.2 mmol) dropwise. After 10 min, a solution of Compound 7 (4.1 g, 17.6 mmol) in DCM (10 mL) was added dropwise and the mixture stirred for 30 min. TEA (7.1 g, 70.4 mmol) was added dropwise and the mixture was warmed to RT, diluted with water and extracted with DCM. The combined organic extracts were concentrated and purified by silica gel chromatography to give 3 g of Compound 8.

8. Following the procedure described for FLS-116, Compound 8 (500 mg, 2.17 mmol) in MeOH (5 mL) and Compound 9 (314 mg, 2.17 mmol) were treated with NaCNBH$_3$ (408 mg, 6.51 mmol) and AcOH (651 mg, 10.85 mmol) to afford 17 mg of FLS-114.

$^1$HNMR (CDCl$_3$, 300 MHz) δ: 1.1 (m, 3H), 1.3 (m, 3H), 2.2 (m, 1H), 3.1-3.4 (m, 3H), 6.5 (d, 1H), 7.1 (m, 1H), 7.2-7.4 (m, 3H), 7.6 (t, 1H), 8.6 (s, 1H), 8.8 (s, 2H). LC-MS: m/z=360.2 (M+1)$^+$.

Synthesis of Example FLS-117

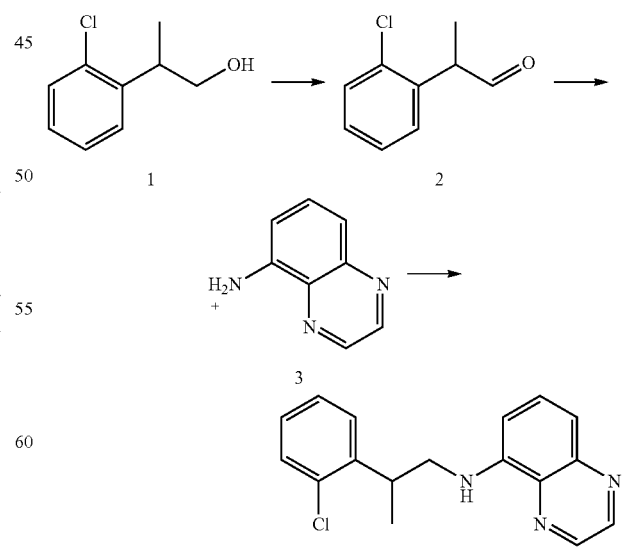

FLS117

Procedure:

1. To a mixture of Compound 1 (20 g, 104.7 mmol) and N,O-dimethylhydroxylamine hydrochloride (12.2 g, 125.6 mmol) in DCM (400 mL) at 0° C. was added DIEA (16.2 g, 125.6 mmol) and HOBT (17 g, 125.6 mmol). EDCI (24 g, 125.6 mmol) was added positionwise and the mixture was stirred at RT for overnight. The mixture was diluted with water and extracted with DCM twice. The combined organic extracts were washed with brine, dried and concentrated to give 21 g of Compound 2.

2. To a solution of Compound 2 (21 g, 89.7 mmol) in dry ether (300 mL) at 0° C. was added MeMgBr (45 mL, 134.5 mmol) dropwise. The mixture was stirred at RT for 2 hours, diluted with saturated NH$_4$Cl solution and extracted with EA twice. The combined organic extracts were concentrated to give 13 g of crude Compound 3.

3. To a solution of trimethyl phosphonoacetate (11.6 g, 63.5 mmol) in dry THF (300 mL) at 0° C. was added 60% NaH (2.55 g, 63.5 mmol) portionwise. After 2 hours stirring at RT, a solution of Compound 3 (10 g, 52.9 mmol) in dry THF (20 mL) was added dropwise. The resulting mixture was stirred at RT for 1 hour and reflux for 2 hours. The mixture was diluted with saturated NH$_4$Cl solution and extracted with EA. The combined organic extracts were washed with water, brine, dried over anhydrous Na$_2$SO$_4$, Procedure:
1. To a solution of DMSO (0.91 g, 11.72 mmol) in DCM (50 mL) at −78° C. was added (COCl)$_2$ (1.5 g, 11.72 mmol). After 15 min. 2-(2-chlorophenyl)propan-1-ol Compound 1, prepared as described in Example FLS-116, (1 g, 5.86 mmol) in DCM (5 mL) was added dropwise. The mixture was stirred at −78° C. for 1 hour and Et$_3$N (2.4 g, 23.44 mmol) was added. The reaction was warmed to RT and washed with water, dried and concentrated to give 0.9 g of Compound 2.
2. To a solution of Compound 2 (250 mg, 1.48 mmol) and Compound 3 (215 mg, 1.48 mmol) in MeOH (5 mL) were added NaCNBH$_3$ (93 mg, 1.48 mmol). HOAc (180 mg, 2.96 mmol) was added and the mixture was stirred at RT for overnight. The reaction mixture was concentrated and purified by silica gel column and Prep-HPLC to give 6.6 mg of FLS-117.

$^1$HNMR (CDCl$_3$, 300 MHz) δ: 1.4 (d, 3H), 3.4 (m, 1H), 3.6 (m, 1H), 3.8 (m, 1H), 6.7-6.8 (d, 1H), 7.1-7.2 (d, 1H), 7.2-7.5 (m, 4H), 7.6 (t, 1H), 8.5 (s, 1H), 8.8 (s, 1H). LC-MS: m/z=298.2 (M+1)$^+$.

Synthesis of Example FLS-118

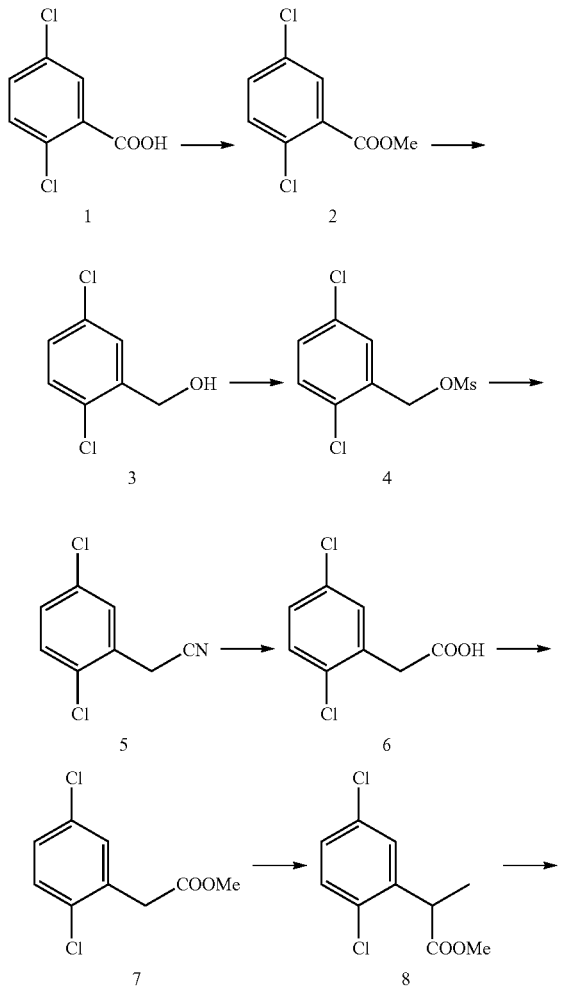

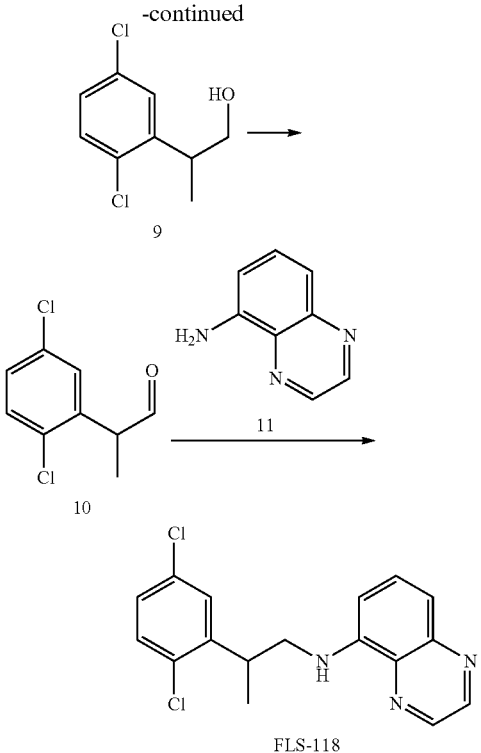

Procedure:
1. Following the procedure described for FLS-116 Step 1, Compound 1 (10 g, 52.3 mmol) in MeOH (150 mL) was treated with SOCl$_2$ (9.3 g, 78.4 mmol) and converted to 10.5 g of Compound 2.
2. Following the procedure described for FLS-116 Step 3, Compound 2 (10.5 g, 48.7 mmol) in dry THF (150 mL) was treated with LiAlH$_4$ (2.2 g, 58.5 mmol) to afford 8.9 g of crude Compound 3.
3. Following the procedure described for FLS-116 Step 4, Compound 3 (8.9 g, 50 mmol) in DCM (100 mL) was treated with TEA (7.6 g, 75 mmol) and MsCl (6.8 g, 60 mmol) to afford 12.7 g of Compound 4.
4. Following the procedure described for FLS-116 Step 5, Compound 4 (12.7 g, 49.8 mmol) was treated with TMSCN (9.9 g, 99.6 mmol) in dry CH$_3$CN (80 mL) and TBAF (19.6 g, 74.9 mmol) in THF (80 mL) to afford 7 g of Compound 5.
5. Following the procedure described for FLS-116 Step 6, Compound 5 (7 g, 37.6 mmol) in EtOH (70 mL) was treated with NaOH solution (10%, 70 mL) to afford 3 g of Compound 6.
6. Following the procedure described for FLS-116 Step 7, Compound 6 (3 g, 14.6 mmol) in MeOH (50 mL) was treated with SOCl$_2$ (2.6 g, 21.9 mmol) to afford 3.1 g of Compound 7.
7. Following the procedure described for FLS-116 Step 2, Compound 7 (3.1 g, 14.2 mmol) in THF (20 mL) was treated with LDA (21.3 mmol, 30 mL) followed by MeI (4 g, 14 mmol) in THF (10 mL) to afford 3 g of crude Compound 8.
8. To a solution of Compound 8 (3 g, 12.8 mmol) in dry THF (50 mL) at 0° C. was added LiAlH$_4$ (0.53 g, 14 mmol) slowly and the mixture stirred for 1 hour, diluted with water, filtered and extracted withed EtOAc. The combined extracts were concentrated to give 2.4 g of Compound 9.

9. To a solution of DMSO (1.82 g, 23.4 mmol) in DCM (50 mL) at −78° C. was added (COCl)$_2$ (3.0 g, 23.4 mmol). After 15 min. Compound 9 (2.4 g, 11.7 mmol) in DCM (5 mL) was added dropwise. The mixture was stirred at −78° C. for 1 hour and Et$_3$N (4.1 g, 46.8 mmol) was added. The reaction was warmed to RT and washed with water, dried and concentrated to give 1.8 g of Compound 10.
10. Following the procedure described for FLS-116 Step 11, Compound 10 (1.8 g, 8.8 mmol) and Compound 11 (1.2 g, 8.8 mmol) in MeOH (20 mL) were treated with NaCNBH$_3$ (550 mg, 8.8 mmol) and HOAc (1 g, 17.6 mmol) to afford 10.4 mg of FLS-118.

$^1$HNMR (CDCl$_3$, 300 MHz) δ: 1.4 (d, 3H), 3.4-3.5 (m, 1H), 3.6 (m, 1H), 3.8 (m, 1H), 6.8 (m, 1H), 7.2 (m, 1H), 7.2-7.4 (m, 3H), 7.6 (t, 1H), 8.8 (s, 1H), 8.6 (s, 2H). LC-MS: m/z=332.2 (M+1)$^+$.

Synthesis of Example FLS-119

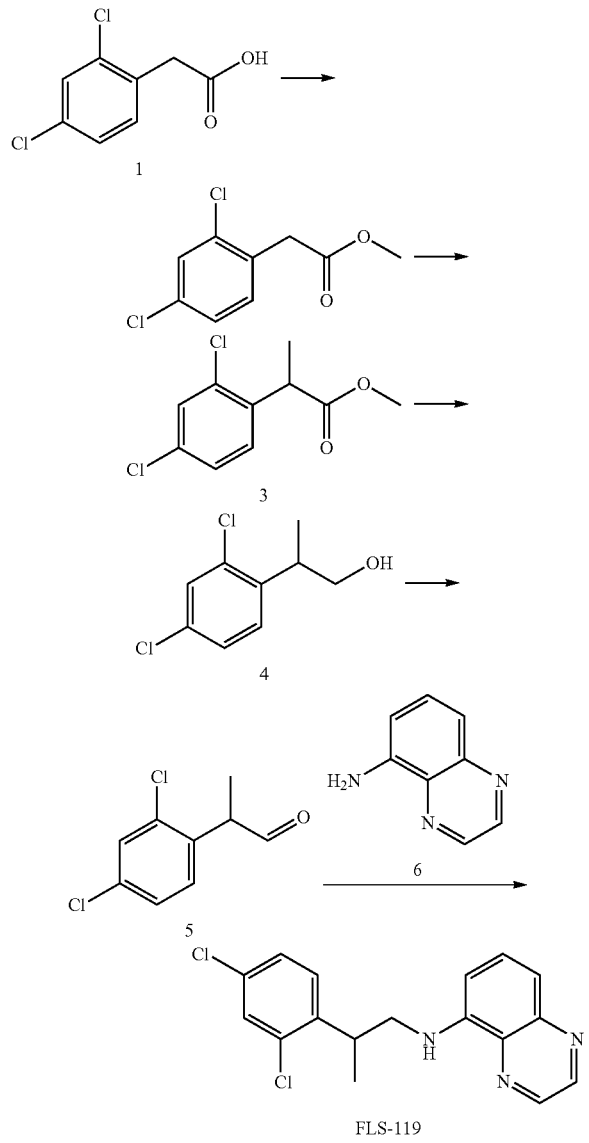

Procedure:
1. Following the procedure described for FLS-116 Step 1, Compound 1 (20 g, 97.5 mmol) in MeOH (250 mL) was treated with SOCl$_2$ (17.4 g, 146.2 mmol) and converted to 21 g of Compound 2.
2. Following the procedure described for FLS-116 Step 2, Compound 2 (21 g, 95.9 mmol) in THF (100 mL) at −78° C. was treated with LDA (143.8 mmol, 180 mL) followed by MeI (20.4 g, 143.8 mmol) to afford 22 g of crude Compound 3.
3. To a solution of Compound 3 (20 g, 85.8 mmol) in dry THF (150 mL) at 0° C. was added LiAlH$_4$ (3.9 g, 103 mmol) slowly and the mixture stirred for 1 hour, diluted with water, filtered and extracted withed EtOAc. The combined extracts were concentrated to give 16 g of 2-(2,4-dichlorophenyl)propan-1-ol Compound 4.
4. To a solution of DMSO (1.5 g, 19.7 mmol) in DCM (50 mL) at −78° C. was added (COCl)$_2$ (2.5 g, 19.7 mmol). After 15 min. 2-(2,4-dichlorophenyl)propan-1-ol Compound 4 (2 g, 9.85 mmol) in DCM (5 mL) was added dropwise. The mixture was stirred at −78° C. for 1 hour and Et$_3$N (3.98 g, 39.3 mmol) was added. The reaction was warmed to RT, diluted water, and the organic layer dried and concentrated to give 1.5 g of Compound 5.
5. Following the procedure described for FLS-116 Step 11, Compound 5 (200 mg, 0.985 mmol) and Compound 6 (143 mg, 0.985 mmol) in MeOH (5 mL) were treated with NaCNBH$_3$ (62 mg, 0.985 mmol) and HOAc (120 mg, 1.97 mmol) to afford 11 mg of FLS-119.

$^1$HNMR (CDCl$_3$, 300 MHz) δ: 1.4 (d, 3H), 3.4 (m, 1H), 3.5-3.6 (m, 1H), 3.7-3.8 (m, 1H), 6.7-6.8 (d, 1H), 7.2-7.4 (m, 3H), 7.4 (s, 1H), 7.6 (t, 1H), 8.6 (s, 1H), 8.8 (s, 1H). LC-MS: m/z=332.1 (M+1)$^+$.

Synthesis of Example FLS-120

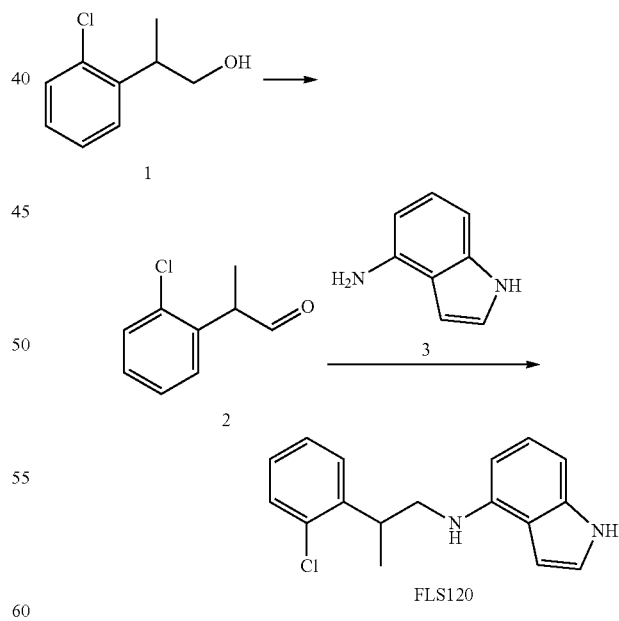

Procedure:
1. To a solution of DMSO (0.91 g, 11.72 mmol) in DCM (50 mL) at −78° C. was added (COCl)$_2$ (1.5 g, 11.72 mmol). After 15 min. Compound 1, prepared as described in Example FLS-116, (1 g, 5.86 mmol) in DCM (5 mL) was added dropwise. The mixture was stirred at −78° C. for 1 hour and Et₃N (2.4 g, 23.44 mmol) was added. The reaction was warmed to RT and washed by water, dried and concentrated to give 0.9 g of Compound 2.

2. Following the procedure described for FLS-116 Step 11, Compound 2 (250 mg, 1.48 mmol) and Compound 3 (195 mg, 1.48 mmol) in MeOH (5 mL) were treated with NaCNBH₃ (93 mg, 1.48 mmol) and HOAc (180 mg, 2.96 mmol) to afford 33 mg of FLS-120.

¹HNMR (CDCl₃, 300 MHz) δ: 1.4 (d, 3H), 3.4-3.6 (m, 2H), 3.7-3.8 (m, 1H), 6.3-6.4 (m, 2H), 6.8 (d, 1H), 7.0-7.1 (m, 2H), 7.1-7.2 (t, 1H), 7.2-7.3 (t, 1H), 7.4-7.6 (m, 2H). LC-MS: m/z=285.2 (M+1)⁺.

Synthesis of Example FH000006-K-6

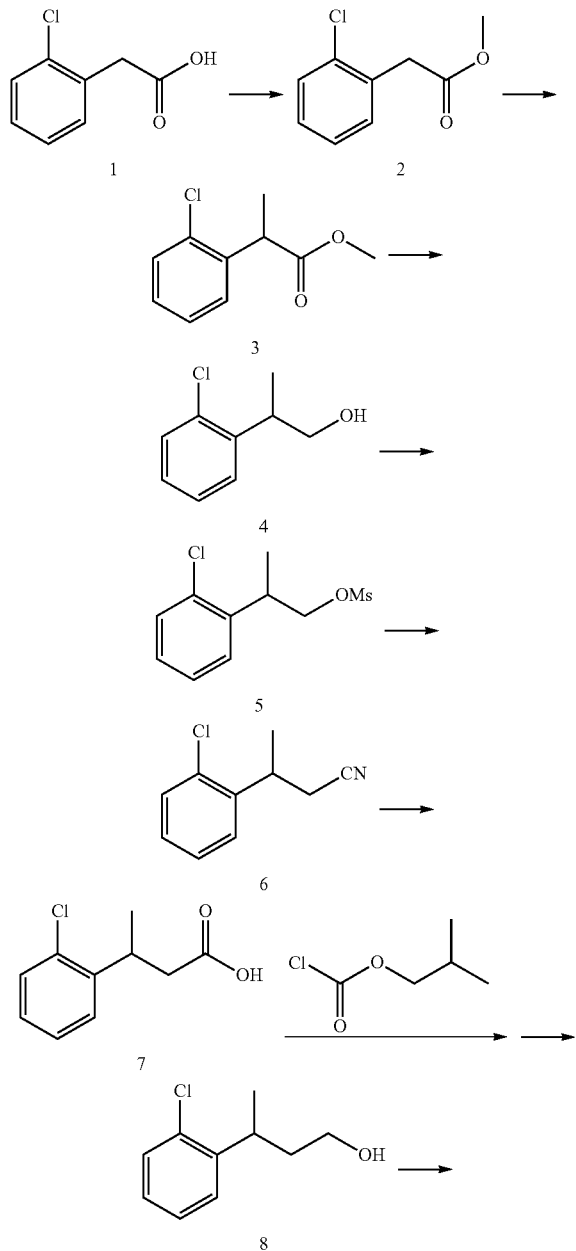

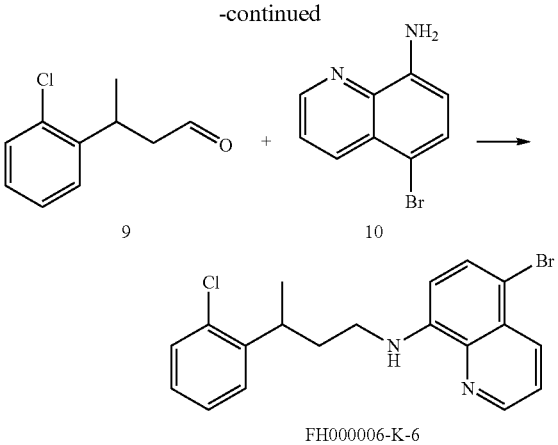

Procedure:

1. To a solution of Compound 1 (10 g, 58.8 mmol) in MeOH (100 mL) at 0° C. was added SOCl₂ (13 mL) dropwise. The resulting solution was stirred at reflux overnight. The solvent was removed in vacuum and the residue was treated with water and extracted with EA. The combined organic extracts were washed with saturated NaHCO₃ solution, brine, dried over anhydrous Na₂SO₄, filtered and concentrated to give Compound 2 (10 g).

2. To a solution of i-Pr₂NH (10.5 mL, 81.4 mmol) in dry THF (100 mL) at −78° C. was added n-BuLi (32.2 mL, 81.4 mmol) dropwise under N₂. After 30 min. a solution of Compound 2 (10 g, 54.34 mmol) in dry THF (100 mL) was added dropwise and after 1 hour CH₃I (11.5 g, 81.4 mmol) was added. The solution was stirred at RT overnight. The mixture was diluted with water and extracted with EA. The combined organic extracts were washed with water, brine, dried over anhydrous Na₂SO₄, filtered and concentrated to give Compound 3 (10 g).

3. To a suspension of LAH (2.2 g, 50.5 mmol) in dry THF (40 mL) at 0° C. was added a solution of Compound 3 (10 g, 50.5 mmol) in dry THF (20 mL) dropwise under N₂. The mixture was heated to reflux for 2 hours. The mixture was diluted with water, filtered and the filter cake washed with THF. The filtrate was concentrated to afford Compound 4 (8.2 g).

4. To a mixture of Compound 4 (8.2 g, 48.2 mmol) in DCM (100 mL) and TEA (10 mL, 72.3 mmol) at 0° C. MsCl (6.6 g, 57.8 mmol) was added dropwise and the mixture stirred at RT for 2 hours. The mixture was diluted with water and extracted with DCM. The combined organic extracts were washed with brine, dried over anhydrous Na₂SO₄, filtered and concentrated to give Compound 5 (9 g).

5. To a solution of Compound 5 (9 g, 36.3 mmol) and TMSCN (7.1 g, 72.6 mol), in MeCN (50 mL) at 0° C. was added a solution of TBAF (14.1 g, 54.4 mmol) in dry THF (50 mL) dropwise. The mixture was heated to 80° C. overnight. The solvent was removed in vacuum and the residue was diluted with water and extracted with EA. The o combined organic extracts were washed with water, brine, dried over anhydrous Na₂SO₄, filtered and concentrated and the residue was purified by silica gel chromatography to afford Compound 6 (3.9 g).

6. A mixture of Compound 6 (3.9 g, 21.7 mmol) and 10% NaOH solution (40 mL) in EtOH (40 mL) was stirred at 90° C. overnight. The solvent was removed in vacuum, the residue was diluted with water and extracted with DCM. The combined organic extracts were washed with water, brine, dried over anhydrous Na$_2$SO$_4$, filtered and concentrated to give Compound 7 (3.4 g).

7. To a solution of Compound 7 (500 mg, 2.53 mmol) in THF (10 mL) and TEA (256 mg, 2.53 mmol) at 0° C. was added isobutyl chloroformate (344 mg, 2.53 mmol). The resulting solution was stirred at RT for 2 hours. NaBH$_4$ (144 mg, 3.8 mmol) was added and the mixture was stirred at RT overnight. The solvent was removed in vacuum and the residue was diluted with water and extracted with EA. The combined organic extracts were washed with brine, dried over anhydrous Na$_2$SO$_4$, filtered and concentrated to give 200 mg of Compound 8.

8. To a solution of oxalyl chloride (275 mg, 2.16 mmol) in DCM (10 mL) at −78° C. under N$_2$ was added dry DMSO (170 mg, 2.16 mmol) dropwise. After 10 min. a solution of Compound 8 (200 mg, 1.08 mmol) in DCM (5 mL) was added dropwise. After 30 min. TEA (437 mg, 4.32 mmol) was added dropwise. The resulting solution was warmed to RT. The mixture was diluted with water and extracted with DCM. The combined organic extracts were concentrated and the residue purified by silica gel chromatography to give 210 mg of crude Compound 9.

9. Preparation of 5-Bromo-8-quinolinamine, Compound 10: To a solution of 8-quinolinamine (1 g, 4.8 mmol) in CH3CN (30 mL) was added NBS (1.28 g, 7.2 mmol). After 2 h the mixture was diluted with water and extracted with EA. The combined organic extracts were concentrated and the residue purified by silica gel to afford 5-bromo-8-quinolinamine Compound 10 (760 mg).

10. To a solution of Compound 9 (210 mg, 1.15 mmol) in MeOH (2 mL) were added Compound 10 (167 mg, 1.15 mmol), NaCNBH$_3$ (73 mg, 1.15 mmol) and AcOH (140 mg, 2.3 mmol) and the mixture stirred at RT overnight. The mixture was concentrated and the residue was purified by silica gel chromatography to give 150 mg of Compound FH000006-K-6.

$^1$HNMR (CDCl$_3$, 300 MHz) δ: 1.3 (d, 3H), 2.1 (m, 2H), 3.2-3.3 (m, 2H), 3.5 (m, 1H), 6.4 (d, 1H), 7.2-7.6 (m, 6H), 8.4 (d, 1H), 8.7 (s, 1H). LC-MS: m/z=391.1 (M+1)$^+$.

Synthesis of Examples FH000006-K-8-A and FH000006-K-8

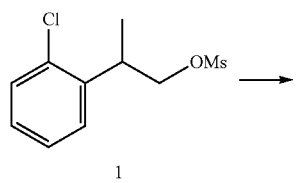

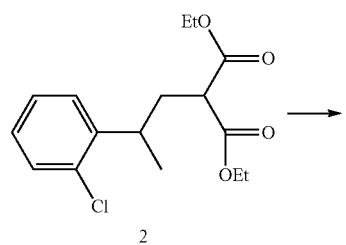

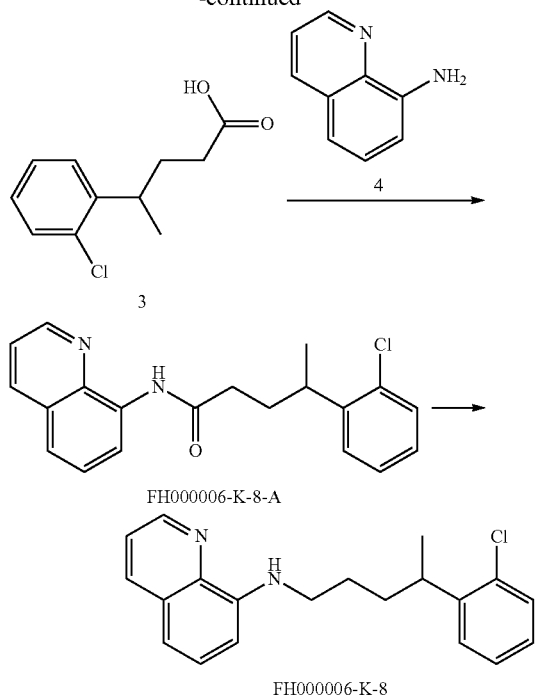

Procedure:

1. To a solution of diethyl malonate (3.36 g, 21 mmol) in DMF (20 mL) was added 60% NaH (0.92 g, 23.1 mmol) and mixture was stirred at RT for 30 min. 2-(2-chlorophenyl)propyl methanesulfonate Compound 1, prepared as described in Example FLS-116, (2.6 g, 10.5 mmol) in DMF (10 mL) was added dropwise and the mixture was heated to 60° C. overnight. The solvent was removed in vacuum, and the residue was diluted with water and extracted with EtOAc. The combined organic extracts were washed with water, brine, dried over anhydrous Na$_2$SO$_4$, filtered and concentrated to give Compound 2 (3.7 g).

2. To a solution of Compound 2 (3.7 g) in EtOH (15 mL) was added HCl (15 mL, 6 M) and the mixture was stirred at 90° C. overnight. The solvent was removed in vacuum and the residue was treated with water and extracted with EtOAc. The combined organic extracts were washed with water, brine, dried over anhydrous Na$_2$SO$_4$, filtered and concentrated to give Compound 3 (800 mg).

3. A mixture of Compound 3 (400 mg, 1.887 mmol), Compound 4 (270 mg, 1.887 mmol), EDCI (720 mg, 3.774 mmol) and DMAP (110 mg, 0.944 mmol) in DCM (30 mL) was stirred at RT overnight. The mixture was diluted with water and extracted with DCM. The combined organic extracts were concentrated and purified by silica gel chromatography to afford FH000006-K-8-A (120 mg).

$^1$HNMR (CDCl$_3$, 300 MHz) δ: 1.3-1.4 (d, 3H), 2.2 (m, 2H), 2.4-2.6 (m, 2H), 3.4-3.5 (m, 1H), 7.1 (m, 1H), 7.2-7.6 (m, 6H), 8.2 (d, 1H), 8.7-8.8 (m, 2H).

LC-MS: m/z=339.2 (M+1)$^+$.

4. To a solution of FH000006-K-8-A (200 mg, 0.5 mmol) in THF (10 mL) were added LAH (95 mg, 2.5 mmol) and the mixture was stirred at 60° C. for 3 hours. The mixture was diluted with water, filtered, the filter cake was washed with THF and the filtrate concentrated. The residue was purified by chromatography to afford FH000006-K-8 (80 mg).

¹HNMR (CDCl₃, 300 MHz) δ: 1.3 (d, 3H), 1.6-1.9 (m, 4H), 3.2-3.5 (m, 3H), 6.6 (d, 1H), 7.0-7.4 (m, 7H), 8.0-8.1 (d, 1H), 8.7 (d, 1H). LC-MS: m/z=325.1 (M+1)+.

Synthesis of Example DV7016

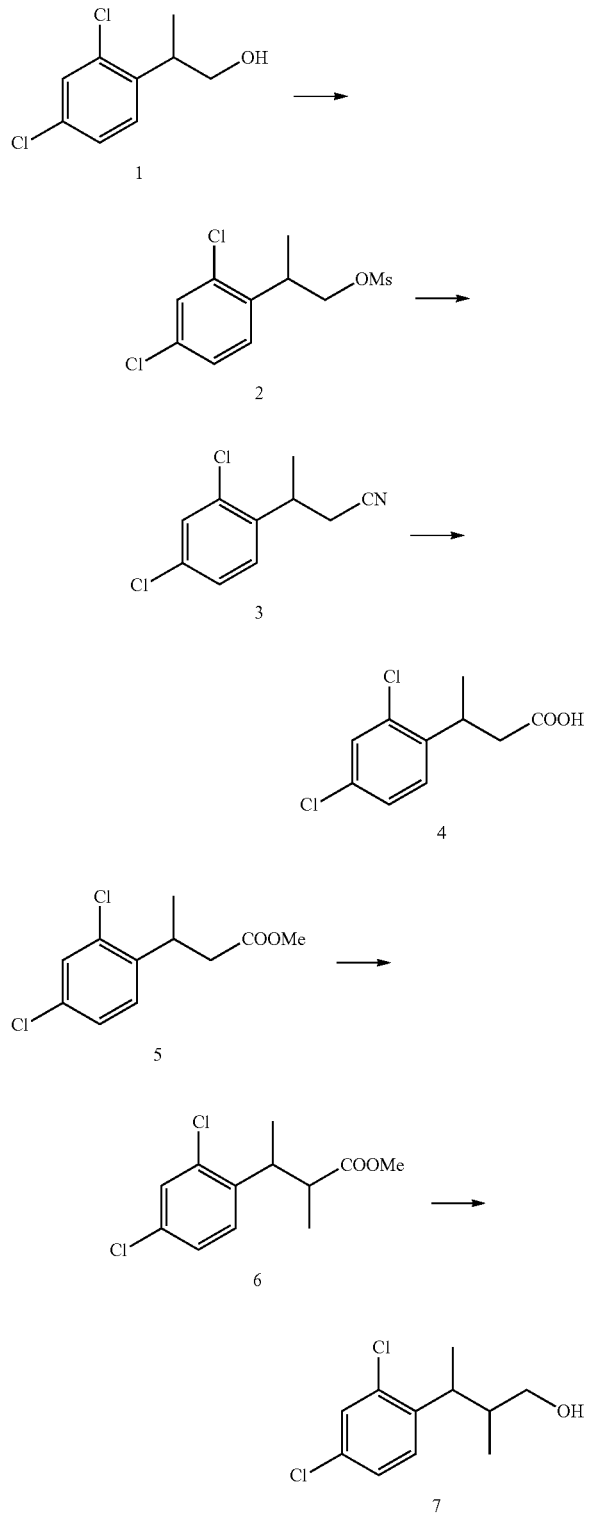

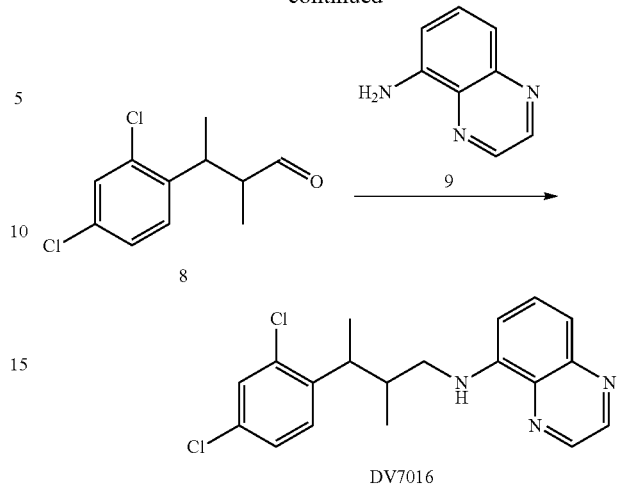

Procedure:

1. Following the procedure described for FLS-116 Step 4, 2-(2,4-dichlorophenyl)propan-1-ol Compound 1 (16 g, 78.0 mmol), prepared as described in Example FLS-119, in DCM (150 mL) was treated with TEA (11.84 g, 117 mmol) and MsCl (10.7 g, 93.6 mmol) to afford 21 g of crude Compound 2.

2. Following the procedure described for FLS-116 Step 5, Compound 2 (21 g, 75 mmol) was treated with TMSCN (14.9 g, 150 mmol) in dry CH₃CN (150 mL) and TBAF (29.4 g, 112.5 mmol) in THF (150 mL) to afford 10 g of Compound 3.

3. Following the procedure described for FLS-116 Step 6, Compound 3 (10 g, 46.9 mmol) in EtOH (70 mL) was treated with NaOH solution (10%, 75 mL) to afford 7.5 g of Compound 4.

4. Following the procedure described for FLS-116 Step 7, Compound 4 (7 g, 32.2 mmol) in MeOH (80 mL) was treated with thionyl chloride (5.74 g, 48.3 mmol) to afford 8.1 g of Compound 5.

5. Following the procedure described for FLS-116 Step 8, Compound 5 (8.1 g, 32.79 mmol) in THF (50 mL) was treated with LDA (39.35 mmol, 70 mL) and MeI (5.6 g, 39.35 mmol) in THF (10 mL) to afford 8 g of Compound 6.

6. Following the procedure described for FLS-116 Step 9, Compound 6 (8 g, 30.7 mmol) in dry THF (100 mL) was treated with LiAlH₄ (1.16 g, 30.7 mmol) to give 5.3 g of Compound 7.

7. Following the procedure described for FLS-116 Step 10, DMSO (3.5 g, 45.4 mmol) in DCM (80 mL), (COCl)₂ (5.8 g, 45.4 mmol) were reacted with Compound 7 (5.3 g, 22.7 mmol) in DCM (10 mL) and Et₃N (9.2 g, 90.8 mmol) to give 4.1 g of Compound 8.

8. Following the procedure described for FLS-116 Step 11, Compound 8 (400 mg, 1.74 mmol) and Compound 9 (250 mg, 1.74 mmol) in MeOH (5 mL) were treated with NaCNBH₃ (320 mg, 5.22 mmol) and AcOH (520 mg, 8.7 mmol) to give 15 mg of DV7016.

¹HNMR (CDCl₃, 300 MHz) δ: 1.1 (m, 3H), 1.3 (m, 3H), 2.2 (m, 1H), 3.0-3.5 (m, 3H), 6.5 (m, 1H), 7.2-7.5 (m, 4H), 7.6 (m, 1H), 8.6 (s, 1H), 8.8 (s, 2H). LC-MS: m/z=332.1 (M+1)⁺.

Assessing Antiviral Activity Against Human Cytomegalovirus (HCMV)

To assess their antiviral activity, some compounds were tested against human cytomegalovirus (HCMV) in vitro. Human MRC5 cells were grown in Dulbecco's Modified Eagle Medium (DMEM) supplemented with 10% fetal bovine serum (FBS) and infected with an HCMV variant expressing GFP tagged pUL99 (the product of late viral UL99 gene) at a multiplicity of 1 infectious unit (IU) per cell. One hour later, medium of the cells was replaced with fresh medium containing the indicated compounds at 50, 25, 12.5, 6.25, 3.13, 1.56, 0.78, 0.39 µM or the carrier in which the compounds are dissolved (DMSO). Final concentration of DMSO was 0.5% in each treatment. Virus yield in the culture supernatant was determined at 96 hours after infection by infecting fresh MRC5 cells and assaying viral IE1 protein expression. Results were plotted using either Prism Software or CDD Vault (CDD Vault was developed by Collaborative Drug Discovery, Inc., 1633 Bayshore Hwy, Suite 342, Burlingame, Calif. 94010) in order to calculate IC50s.

Alternatively, antiviral efficacy of some compounds was assessed by inhibition of HCMV replication during in vitro replication assays. Briefly, confluent monolayers of MRC5 fibroblasts in a 96 well plate format (~1.0×10^4 cells/well) were infected with an AD169 strain of HCMV for one hour. After the initial incubation hour, virus containing media was removed and 100 ul of media with sequential dilutions of FORGE compounds added to each well. The concentrations of the FORGE compounds were 50 µM, 25 µM, 12.5 M, 6.25 µM, 3.125 µM, 1.56 µM, and 0.78125 µM as well as a vehicle control (0.5% DMSO). The concentration of DMSO was constant between all conditions. Assays were performed in duplicate. Infected plates were returned to the incubator and the viral infection was allowed to progress for four days. On the fourth day, 50 µL of cell free supernatant was collected from each well and used to infect a new 96 well plate seeded with a confluent monolayer of MRC5 fibroblasts along with 50 µL of media to bring the total volume to 100 µL. The next day the media was removed and the infected monolayer was fixed with cold methanol, and Immediate Early proteins were detected by immunofluorescence assays to quantify the number of cells that were infected with HCMV. IE gene expression was quantified within five random fields within each well and corresponding numbers were utilized to determine viral replication. Results from each well were normalized to the vehicle control well so as to allow a percent reduction from no drug treatment to be calculated. Results were plotted using either Prism Software or CDD Vault in order to calculate IC50s.

TABLE 1

| Example | Structure | HCMV IC$_{50}$ |
|---|---|---|
| Example 1 | [quinoline-NH-CH$_2$CH$_2$-CH(CH$_3$)-C$_6$H$_4$-OMe (para)] | 25 µM < IC50 < 50 µM |
| Example 2 | [quinoline-NH-C(=O)-CH$_2$-CH(CH$_3$)-C$_6$H$_4$-OMe (para)] | >50 µM |
| Example 3 | [quinoline-NH-CH$_2$CH$_2$-CH(CH$_3$)-C$_6$H$_4$-OMe (meta)] | 25 µM < IC50 < 50 µM |
| Example 4 | [quinoline-NH-C(=O)-CH$_2$-CH(CH$_3$)-C$_6$H$_4$-OMe (meta)] | 21.2 ± 14.5 µM |
| Example 5 | [quinoline-NH-CH$_2$CH$_2$-CH(CH$_3$)-C$_6$H$_4$-Cl (ortho)] | 18.6 ± 4.62 µM |

TABLE 1-continued

| Example | Structure | HCMV IC$_{50}$ |
| --- | --- | --- |
| Example 6 | quinolin-3-yl-NH-C(O)-CH$_2$-CH(CH$_3$)-(2-Cl-phenyl) | 21.1 ± 14.5 μM |
| Example 7 | quinolin-3-yl-NH-CH$_2$-CH$_2$-CH(CH$_3$)-phenyl | >50 μM |
| Example 8 | quinolin-3-yl-NH-C(O)-CH$_2$-CH(CH$_3$)-phenyl | 3.03 ± 0.69 μM |
| Example 9 | quinolin-6-yl-NH-CH$_2$-CH$_2$-CH(CH$_3$)-(4-OMe-phenyl) | 2.41 ± 0.04 μM |
| Example 10 | quinolin-6-yl-NH-C(O)-CH$_2$-CH(CH$_3$)-(4-OMe-phenyl) | 5.82 ± 1.98 μM |
| Example 11 | quinolin-6-yl-NH-CH$_2$-CH$_2$-CH(CH$_3$)-(3-OMe-phenyl) | 5.75 ± 2.47 μM |
| Example 12 | quinolin-6-yl-NH-C(O)-CH$_2$-CH(CH$_3$)-(3-OMe-phenyl) | 3.34 ± 1.45 μM |
| Example 13 | quinolin-6-yl-NH-CH$_2$-CH$_2$-CH(CH$_3$)-(2-OMe-phenyl) | 23.4 ± 0.60 μM |

TABLE 1-continued

| Example | Structure | HCMV IC$_{50}$ |
|---|---|---|
| Example 14 | 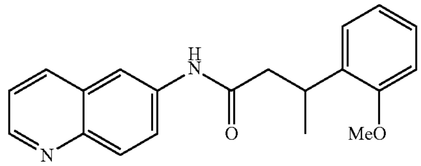 [SMILES: COc1ccccc1C(C)CC(=O)Nc1ccc2ncccc2c1] | 2.20 ± 1.32 μM |
| Example 15 | 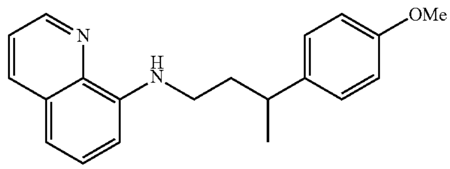 [SMILES: COc1ccc(C(C)CCNc2cccc3cccnc23)cc1] | 3.27 ± 0.41 μM |
| Example 16 | 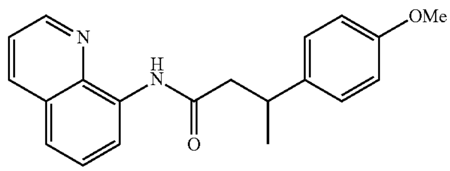 [SMILES: COc1ccc(C(C)CC(=O)Nc2cccc3cccnc23)cc1] | 26.9 ± 11.5 μM |
| Example 17 | 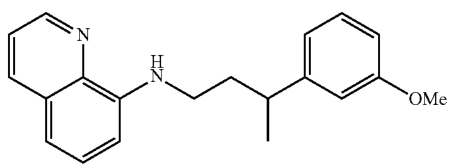 [SMILES: COc1cccc(C(C)CCNc2cccc3cccnc23)c1] | 2.69 ± 0.94 μM |
| Example 18 | 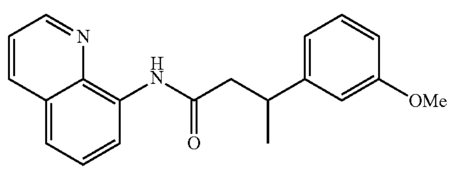 [SMILES: COc1cccc(C(C)CC(=O)Nc2cccc3cccnc23)c1] | >50 μM |
| Example 19 | 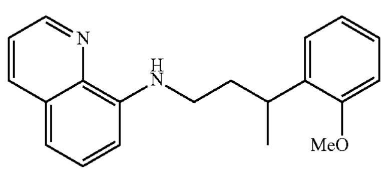 [SMILES: COc1ccccc1C(C)CCNc1cccc2cccnc12] | 1.28 ± 0.16 μM |
| Example 20 | 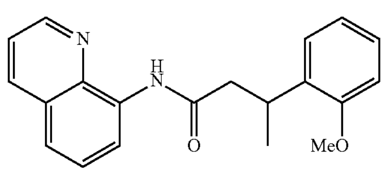 [SMILES: COc1ccccc1C(C)CC(=O)Nc1cccc2cccnc12] | 19.7 ± 14.7 μM |
| Example 21 | 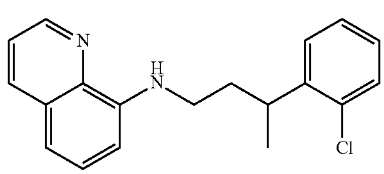 [SMILES: CC(CCNc1cccc2cccnc12)c1ccccc1Cl] | 1.20 ± 0.52 μM |
| Example 22 | 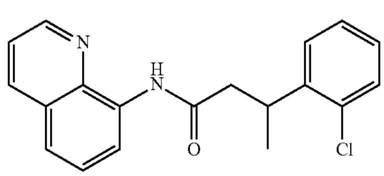 [SMILES: CC(CC(=O)Nc1cccc2cccnc12)c1ccccc1Cl] | 1.28 ± 1.82 μM |

TABLE 1-continued

| Example | Structure | HCMV IC$_{50}$ |
| --- | --- | --- |
| Example 23 | 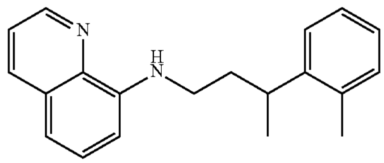 [SMILES: Cc1ccccc1C(C)CCNc1cccc2cccnc12] | 2.01 ± 0.71 μM |
| Example 24 | 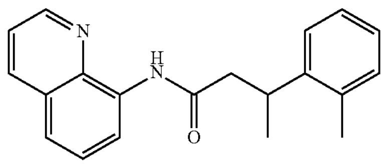 [SMILES: Cc1ccccc1C(C)CC(=O)Nc1cccc2cccnc12] | >50 μM |
| Example 25 | 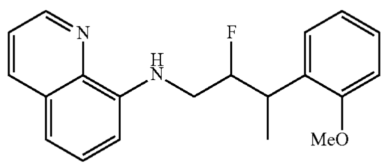 [SMILES: COc1ccccc1C(C)C(F)CNc1cccc2cccnc12] | 3.73 ± 0.46 μM |
| Example 26 | 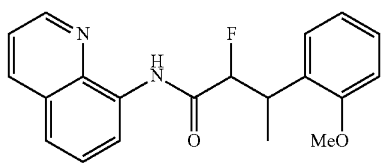 [SMILES: COc1ccccc1C(C)C(F)C(=O)Nc1cccc2cccnc12] | 5.38 ± 3.93 μM |
| Example 27 | 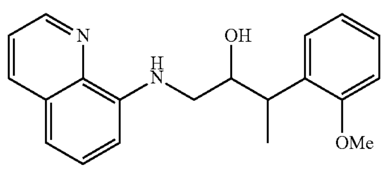 [SMILES: COc1ccccc1C(C)C(O)CNc1cccc2cccnc12] | 28.5 ± 2.68 μM |
| Example 28 | 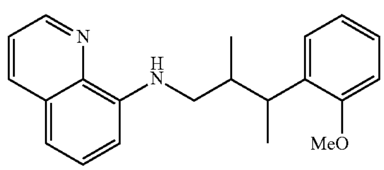 [SMILES: COc1ccccc1C(C)C(C)CNc1cccc2cccnc12] | 2.89 ± 0.95 μM |
| Example 29 | 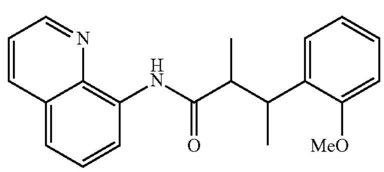 [SMILES: COc1ccccc1C(C)C(C)C(=O)Nc1cccc2cccnc12] | 11.5 ± 7.71 μM |
| Example 30 | 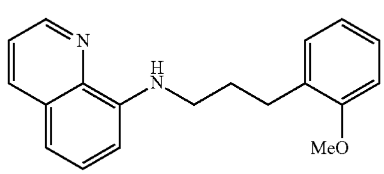 [SMILES: COc1ccccc1CCCNc1cccc2cccnc12] | 12.1 ± 8.44 μM |
| Example 31 | 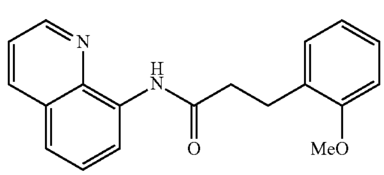 [SMILES: COc1ccccc1CCC(=O)Nc1cccc2cccnc12] | >50 μM |

TABLE 1-continued

| Example | Structure | HCMV IC$_{50}$ |
|---|---|---|
| Example 32 | 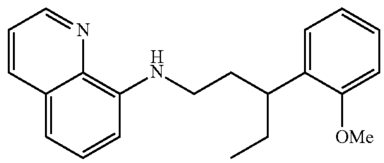 [SMILES: CCC(CCNc1cccc2cccnc12)c1ccccc1OC] | 2.25 ± 0.33 μM |
| Example 33 | 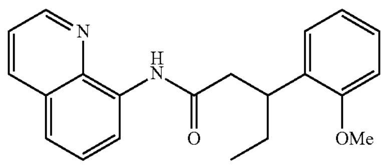 [SMILES: CCC(CC(=O)Nc1cccc2cccnc12)c1ccccc1OC] | 5.30 ± 0.31 μM |
| Example 34 | 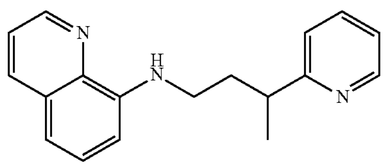 [SMILES: CC(CCNc1cccc2cccnc12)c1ccccn1] | >50 μM |
| Example 35 | 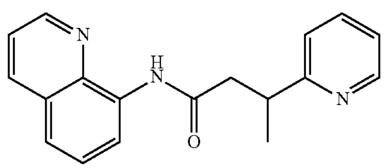 [SMILES: CC(CC(=O)Nc1cccc2cccnc12)c1ccccn1] | >50 μM |
| Example 36 | 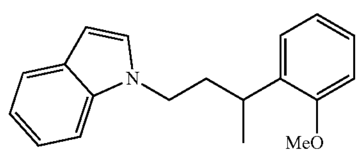 [SMILES: COc1ccccc1C(C)CCn1ccc2ccccc21] | >50 μM |
| Example 37 | 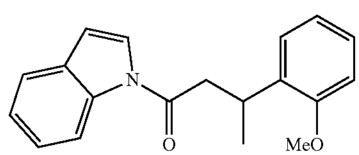 [SMILES: COc1ccccc1C(C)CC(=O)n1ccc2ccccc21] | >50 μM |
| Example 38 | 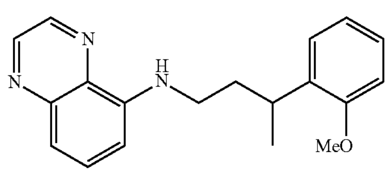 [SMILES: COc1ccccc1C(C)CCNc1cccc2nccnc12] | 3.61 ± 0.54 μM |
| Example 39 | 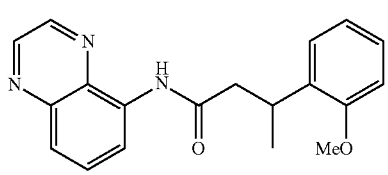 [SMILES: COc1ccccc1C(C)CC(=O)Nc1cccc2nccnc12] | >50 μM |
| Example 40 | 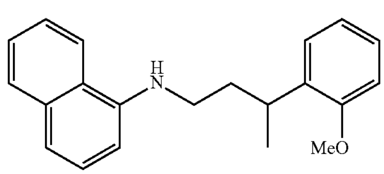 [SMILES: COc1ccccc1C(C)CCNc1cccc2ccccc12] | 2.83 ± 0.28 μM |

TABLE 1-continued
| Example | Structure | HCMV IC$_{50}$ |
|---|---|---|
| Example 41 | 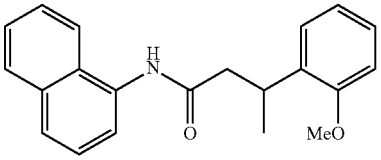 [SMILES: COc1ccccc1C(C)CC(=O)Nc1cccc2ccccc12] | 29.2 ± 17.8 μM |
| Example 42 | 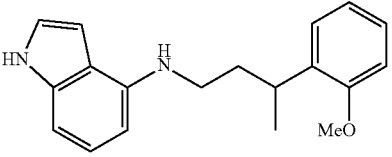 [SMILES: COc1ccccc1C(C)CCNc1cccc2[nH]ccc12] | 1.32 ± 0.84 μM |
| Example 43 | 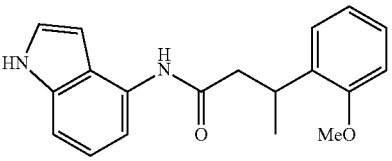 [SMILES: COc1ccccc1C(C)CC(=O)Nc1cccc2[nH]ccc12] | 12.5 ± 4.14 μM |
| Example 44 | 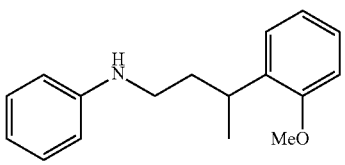 [SMILES: COc1ccccc1C(C)CCNc1ccccc1] | >50 μM |
| Example 45 | 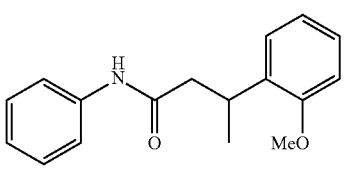 [SMILES: COc1ccccc1C(C)CC(=O)Nc1ccccc1] | >50 μM |
| Example 46 | 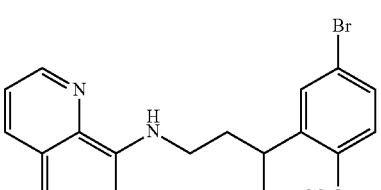 | 21.7 ± 2.48 μM |
| Example 47 | 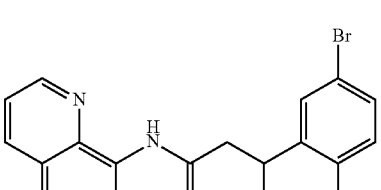 | 5.88 ± 1.93 μM |
| Example 48 | 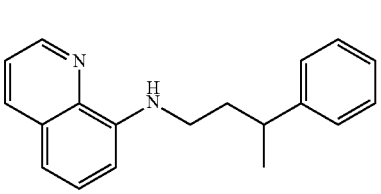 [SMILES: CC(CCNc1cccc2cccnc12)c1ccccc1] | >50 μM |

TABLE 1-continued

| Example | Structure | HCMV IC$_{50}$ |
|---|---|---|
| Example 49 | 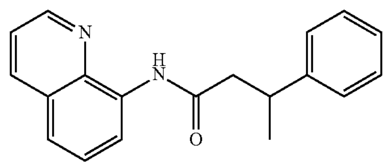 [SMILES: CC(CC(=O)Nc1cccc2cccnc12)c1ccccc1] | >50 μM |
| Example 50 | 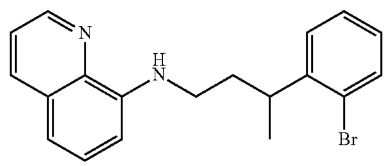 [SMILES: CC(CCNc1cccc2cccnc12)c1ccccc1Br] | 2.92 ± 1.26 μM |
| Example 51 | 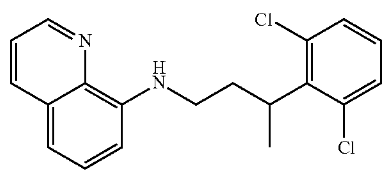 [SMILES: CC(CCNc1cccc2cccnc12)c1c(Cl)cccc1Cl] | 1.94 ± 0.51 μM |
| Example 52 | 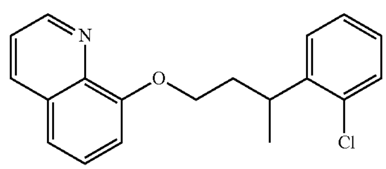 [SMILES: CC(CCOc1cccc2cccnc12)c1ccccc1Cl] | 1.98 ± 0.68 μM |
| Example 53 | 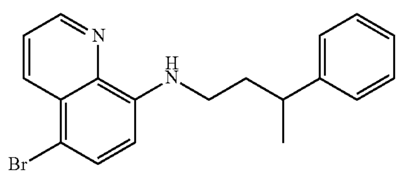 [SMILES: CC(CCNc1ccc(Br)c2cccnc12)c1ccccc1] | 11.6 ± 0.36 μM |
| Example FLS-114 | 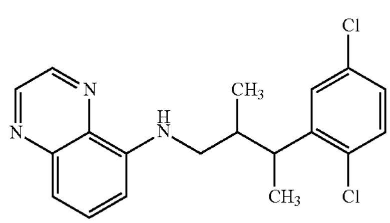 [SMILES: CC(CNc1cccc2nccnc12)C(C)c1cc(Cl)ccc1Cl] | 6.4 μM |
| Example FLS-116 | 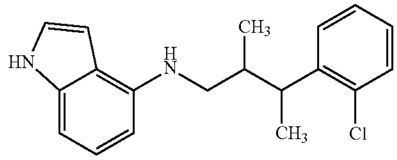 [SMILES: CC(CNc1cccc2[nH]ccc12)C(C)c1ccccc1Cl] | 3.5 μM |
| Example FLS-117 | 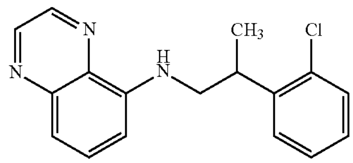 [SMILES: CC(CNc1cccc2nccnc12)c1ccccc1Cl] | 3.2 μM |

TABLE 1-continued

| Example | Structure | HCMV IC$_{50}$ |
|---|---|---|
| Example FLS-118 | 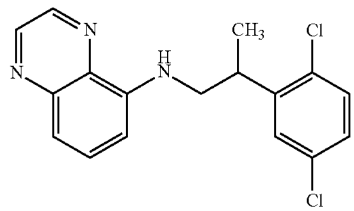 [SMILES: CC(CNc1cccc2nccnc12)c1cc(Cl)ccc1Cl] | 3.2 μM |
| Example FLS-119 | 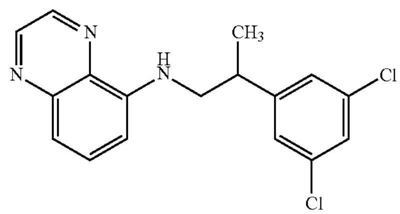 [SMILES: CC(CNc1cccc2nccnc12)c1cc(Cl)cc(Cl)c1] | 2.7 μM |
| Example FLS-120 | 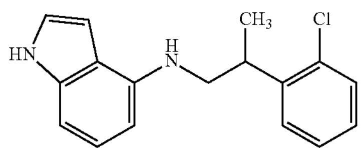 [SMILES: CC(CNc1cccc2[nH]ccc12)c1ccccc1Cl] | 5.0 μM |
| Example FH000006-K-6 | 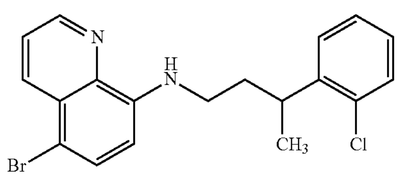 [SMILES: CC(CCNc1ccc(Br)c2cccnc12)c1ccccc1Cl] | 7.9 μM |
| Example FH000006-K-8 | 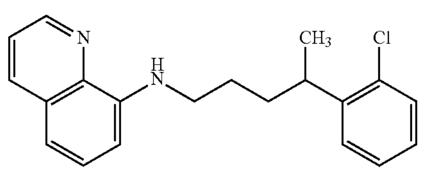 [SMILES: CC(CCCNc1cccc2cccnc12)c1ccccc1Cl] | 6.3 μM |
| Example FH000006-K-8-A | 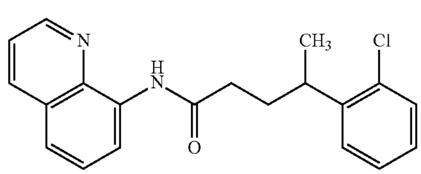 [SMILES: CC(CCC(=O)Nc1cccc2cccnc12)c1ccccc1Cl] | 4.5 μM |
| Example DV7016 | 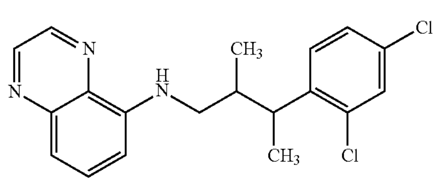 [SMILES: CC(CNc1cccc2nccnc12)C(C)c1ccc(Cl)cc1Cl] | 23.1 μM |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising a compound of formula wherein:

X is NH or O;

$R_1$ and $R_7$ are independently selected from H, halo, lower straight chain or branched alkyl, and $OR_6$;

$R_3$, $R_4$, and $R_5$ are independently selected from H, halo, —CN, lower straight chain or branched alkyl, and $OR_6$;

each $R_6$ is independently selected from H, lower straight chain or branched alkyl;

n is 1, 2 or 3;

the group is substituted with 0, 1 or 2 groups independently selected from halo, —CN, lower straight chain or branched alkyl; and at least one of $R_3$, $R_4$, or $R_5$ is in the ortho position and selected from the group consisting of halo, —CN, a straight chain or branched alkyl of 1 to 4 carbon atoms, and a straight or branched alkoxy of 1 to 4 carbon atoms;

or a pharmaceutically acceptable salt thereof.

2. The composition of claim 1, wherein the group is:

wherein:

$R_8$ is selected from H, halo and —CN.

3. The composition of claim 2, wherein at least two of $R_3$, $R_4$, or $R_5$ is in the ortho position and selected from the group consisting of halo, —CN, a straight chain or branched alkyl of 1 to 4 carbon atoms, and a straight or branched alkoxy of 1 to 4 carbon atoms.

4. The composition of claim 2, wherein $R_2$ is selected from halo, lower straight chain or branched alkyl, and $OR_6$.

5. The composition of claim 2, wherein the compound is selected from the group consisting of:

-continued

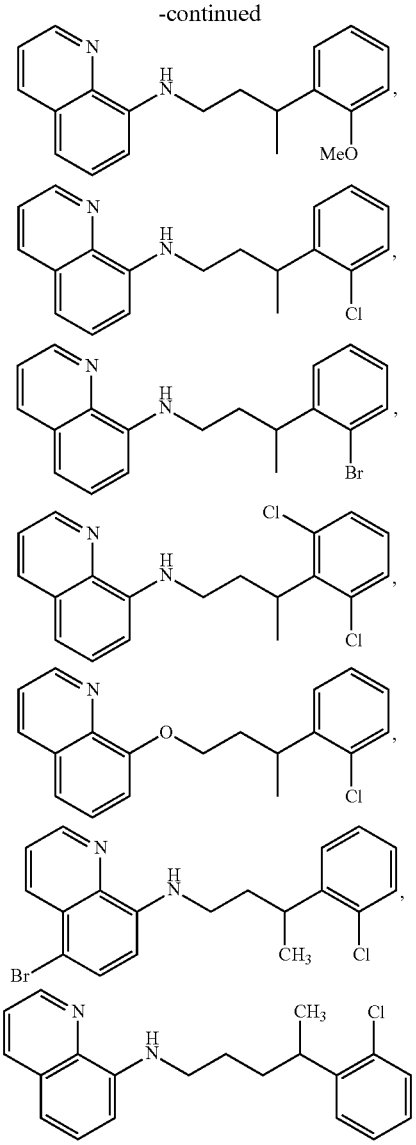

and pharmaceutically acceptable salts thereof.

6. A pharmaceutical composition comprising a compound of formula

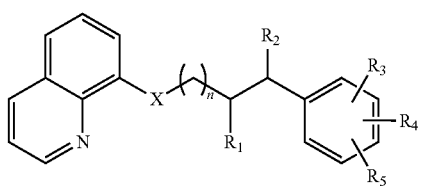

wherein:
X is NH or O;
$R_1$ and $R_2$ are independently selected from H, halo, lower straight chain or branched alkyl, and $OR_6$;
$R_3$, $R_4$, and $R_5$ are independently selected from H, halo, —CN, lower straight chain or branched alkyl, and $OR_6$;
each $R_6$ is independently selected from H, lower straight chain or branched alkyl;
n is 1, 2 or 3;

the

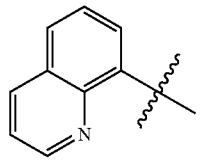 [SMILES: *c1cccc2cccnc12]

group is substituted with 0, 1 or 2 groups independently selected from halo, —CN, lower straight chain or branched alkyl; and
at least one of $R_3$, $R_4$, or $R_5$ is in the ortho position and selected from the group consisting of halo, —CN, a straight chain or branched alkyl of 1 to 4 carbon atoms, and a straight or branched alkoxy of 1 to 4 carbon atoms;
or a pharmaceutically acceptable salt thereof;
and a pharmaceutically acceptable carrier.

7. The pharmaceutical composition of claim 6, wherein the

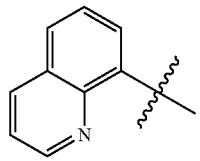 [SMILES: *c1cccc2cccnc12]

group is

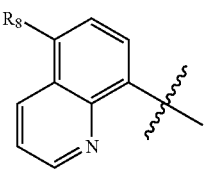

wherein:
$R_8$ is selected from H, halo and —CN.

8. The pharmaceutical composition of claim 7, wherein at least two of $R_3$, $R_4$, or $R_5$ is in the ortho position and selected from the group consisting of halo, —CN, a straight chain or branched alkyl of 1 to 4 carbon atoms, and a straight or branched alkoxy of 1 to 4 carbon atom.

9. The pharmaceutical composition of claim 7, wherein $R_2$ is selected from halo, lower straight chain or branched alkyl, and $OR_6$.

10. The pharmaceutical composition of claim 7, wherein the compound is selected from the group consisting of:

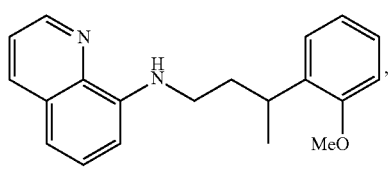

-continued

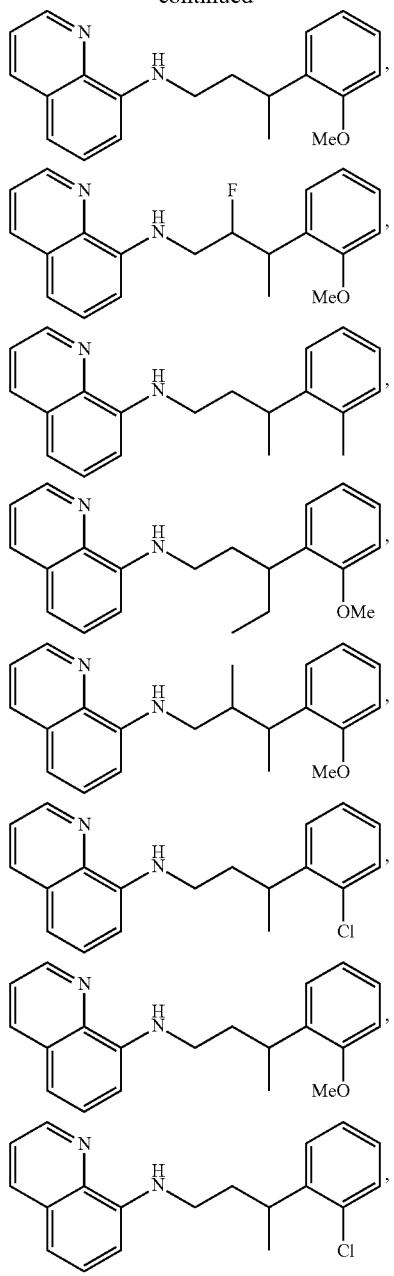

-continued

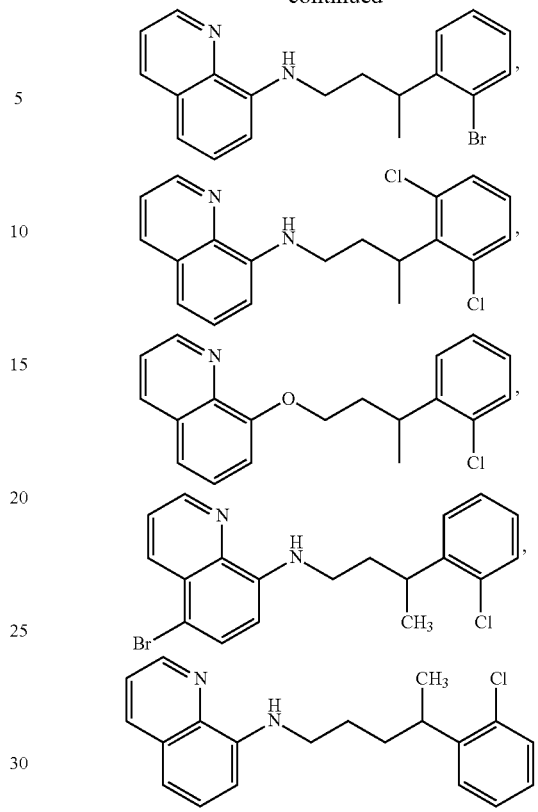

and pharmaceutically acceptable salts thereof.

11. The composition of claim 1, wherein at least two of $R_3$, $R_4$, or $R_5$ is in the ortho position and selected from the group consisting of halo, —CN, a straight chain or branched alkyl of 1 to 4 carbon atoms, and a straight or branched alkoxy of 1 to 4 carbon atoms.

12. The composition of claim 1, wherein $R_2$ is selected from halo, lower straight chain or branched alkyl, and $OR_6$.

13. The pharmaceutical composition of claim 6, wherein at least two of $R_3$, $R_4$, or $R_5$ is in the ortho position and selected from the group consisting of halo, —CN, a straight chain or branched alkyl of 1 to 4 carbon atoms, and a straight or branched alkoxy of 1 to 4 carbon atoms.

14. The pharmaceutical composition of claim 6, wherein $R_2$ is selected from halo, lower straight chain or branched alkyl, and $OR_6$.

* * * * *